(12) United States Patent
Iwasaka

(10) Patent No.: US 10,470,646 B2
(45) Date of Patent: Nov. 12, 2019

(54) MEDICAL INSTRUMENT GUIDING DEVICE

(71) Applicant: FUJIFILM Corporation, Tokyo (JP)

(72) Inventor: Masayuki Iwasaka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 356 days.

(21) Appl. No.: 14/868,407

(22) Filed: Sep. 29, 2015

(65) Prior Publication Data

US 2016/0015256 A1 Jan. 21, 2016

Related U.S. Application Data

(63) Continuation of application No. PCT/JP2014/058779, filed on Mar. 27, 2014.

(30) Foreign Application Priority Data

Mar. 29, 2013 (JP) ................................. 2013-074015

(51) Int. Cl.
*A61B 1/00* (2006.01)
*A61B 1/012* (2006.01)
(Continued)

(52) U.S. Cl.
CPC ...... *A61B 1/00154* (2013.01); *A61B 1/00087* (2013.01); *A61B 1/00131* (2013.01);
(Continued)

(58) Field of Classification Search
CPC ............ A61B 1/00131; A61B 1/00133; A61B 1/00135; A61B 1/0014; A61B 1/00154; A61B 1/0016; A61B 1/01; A61B 1/313; A61B 1/3132; A61B 17/34; A61B 2017/3445; A61B 2017/3447
(Continued)

(56) References Cited

U.S. PATENT DOCUMENTS 5,836,869 A 11/1998 Kudo et al.
6,036,637 A 3/2000 Kudo
(Continued)

FOREIGN PATENT DOCUMENTS

JP H08164148 6/1996
JP H10118076 5/1998
(Continued)

OTHER PUBLICATIONS

"Written Opinion of the International Searching Authority of PCT/JP2014/058779", dated May 13, 2014, with English translation thereof, pp. 1-7.

*Primary Examiner* — Ryan N Henderson
(74) *Attorney, Agent, or Firm* — JCIPRNET

(57) ABSTRACT

A medical instrument guiding device (outer tube) to be tapped into a body wall includes: an endoscope insertion hole for inserting the endoscope; a treatment tool insertion hole for inserting the treatment tool; and an interlocking mechanism for moving the endoscope back and forth in interlock with the back-and-forth movement of the treatment tool. The interlocking mechanism includes an endoscope-side roller contacts with an endoscope insertion part and moves in interlock with the endoscope insertion part, and a treatment tool-side roller which contacts with a treatment tool insertion part and moves in interlock with the treatment tool insertion part, and those rollers rotates in interlock with each other. In response to the movement of the treatment tool insertion part, the treatment tool-side roller and the endoscope-side roller rotate in an opposite direction to move the endoscope insertion part.

14 Claims, 34 Drawing Sheets

(51) Int. Cl.
 *A61B 17/34* (2006.01)
 *A61B 1/313* (2006.01)
 *A61B 17/00* (2006.01)
(52) U.S. Cl.
 CPC ...... *A61B 1/00133* (2013.01); *A61B 1/00135* (2013.01); *A61B 1/012* (2013.01); *A61B 1/3132* (2013.01); *A61B 17/3421* (2013.01); *A61B 17/3423* (2013.01); *A61B 2017/3445* (2013.01); *A61B 2017/3447* (2013.01)
(58) Field of Classification Search
 USPC ............. 600/104, 106, 114, 115, 154; 604/164.09–164.11, 167.01–167.06
 See application file for complete search history.

(56) References Cited

U.S. PATENT DOCUMENTS

2004/0167559 A1* 8/2004 Taylor ............... A61B 17/3423
 606/185
2007/0232863 A1 10/2007 Miyake et al.
2007/0265502 A1 11/2007 Minosawa et al.
2012/0253132 A1* 10/2012 Davis ................ A61B 17/3423
 600/201
2014/0207070 A1* 7/2014 Tegg ................. A61M 39/0606
 604/167.05
2015/0080650 A1 3/2015 Dejima et al.

FOREIGN PATENT DOCUMENTS

| | | |
|---|---|---|
| JP | H10179512 | 7/1998 |
| JP | 2002017752 | 1/2002 |
| JP | 2002209835 | 7/2002 |
| JP | 2004141486 | 5/2004 |
| JP | 2004180858 | 7/2004 |
| JP | 2005095634 | 4/2005 |
| JP | 2007222239 | 9/2007 |
| JP | 2007301378 | 11/2007 |
| WO | 2013176167 | 11/2013 |

* cited by examiner

MEDICAL INSTRUMENT GUIDING DEVICE

CROSS-REFERENCE TO RELATED APPLICATIONS

This application is a Continuation of PCT International Application No. PCT/JP2014/058779 filed on Mar. 27, 2014, which claims priority under 35 U.S.C. § 119(a) to Japanese Patent Application No. 2013-074015 filed on Mar. 29, 2013. Each of the above application(s) is hereby expressly incorporated by reference, in its entirety, into the present application.

BACKGROUND OF THE INVENTION

Field of the Invention

The present invention relates to a medical instrument guiding device, and particularly relates to a medical instrument guiding device which guides an endoscope and a treatment tool into a body cavity so as to freely move back and forth and which moves the endoscope back and forth in interlock with the back-and-forth movement of the treatment tool.

Description of the Related Art

A laparoscope has been known as an endoscopic instrument that is inserted from the skin on a body surface into an abdominal cavity. A surgery (laparoscopic surgery) using this laparoscope only requires a smaller surgical wound than laparotomy and thoracotomy do, and can reduce the post-operation bed rest period. Consequently, such a surgery has recently been widespread in many operations.

Typically, in a laparoscopic surgery (e.g., laparoscopic cholecystectomy etc.), an operator who performs treatment and a laparoscopist who operates a laparoscope are present. The treatment and the operation of the laparoscope are separately performed. Consequently, during the operation, the operator performs treatment while successively instructing the laparoscopist in order to obtain an optimal image for treatment.

However, according to the scheme where the operator instructs the laparoscopist, it is difficult to obtain an image which the operator actually wishes, thereby causing a problem in that stress is applied to the operator. Furthermore, the laparoscopist performs an operation after the operator issues an instruction, thereby causing another problem in that the operation requires time. Moreover, a hand of the operator and a hand of the laparoscopist sometimes interfere with each other above the abdominal wall of a patient, thereby causing yet another problem in that the operation becomes complicated.

Japanese Patent Application Laid-Open No. 2007-301378 (PTL 1) describes a technique as a configuration that allows a treatment tool and an endoscope to move in interlock with each other. The technique detects the amount of insertion and inclination of the treatment tool, controls optical zooming and electronic zooming of the endoscope to cause the imaging range of the endoscope to follow the movement of the treatment tool.

Furthermore, Japanese Patent Application Laid-Open No. 10-118076 (PTL 2) and Japanese Patent Application Laid-Open No. 2007-222239 (PTL 3) describe a technique that provides a marker at a distal end part of a treatment tool, detects the position of the marker to thereby detect the position of the treatment tool, and causes the imaging range of the endoscope to follow the movement of the treatment tool.

Moreover, Japanese Patent Application Laid-Open No. 8-164148 (PTL 4) describes a technique that causes a magnetic sensor provided for a treatment tool to detect the position of the treatment tool, and allows the imaging range of an endoscope to follow the movement of the treatment tool.

SUMMARY OF THE INVENTION

However, the method that detects the position or the like of the treatment tool and causes the imaging range of the endoscope to follow the movement of the treatment tool as with the conventional case has a problem in that the scale of the system becomes large.

The present invention is made in view of such circumstances, and aims to provide a medical instrument guiding device which can obtain an image desired by a surgeon in a simple configuration.

To achieve the above-mentioned object, a medical instrument guiding device according to an aspect of the present invention includes: a guide member configured to penetrate a body wall and to be inserted in a body cavity; an endoscope insertion hole which is provided in the guide member and into which an endoscope that performs observation in the body cavity can be inserted so as to be freely movable back and forth; a treatment tool insertion hole which is provided in the guide member and into which a treatment tool that inspects or treats a diseased site in the body cavity can be inserted so as to be freely movable back and forth; and a back-and-forth movement transmission mechanism which is configured to transmit back-and-forth movement of the treatment tool to the endoscope, is provided in the inside of the guide member, and includes a rotation member which has a rotation axis that three-dimensionally intersects with a longitudinal axis of the treatment tool insertion hole and rotates according to the back-and-forth movement of the treatment tool.

According to the aspect of the present invention, since the endoscope and the treatment tool can be inserted into the body cavity through one guide member, it is not necessary to tap guide members, each of which individually guides the endoscope and the treatment tool into the body cavity, into patient's body wall, and thus it is possible to reduce invasion applied to patient's body wall.

Moreover, the endoscope mechanically moves back and forth in interlock with the back-and-forth movement of the treatment tool through the rotation member of the back-and-forth movement transmission mechanism. Therefore, it becomes unnecessary to operate the endoscope to move back and forth so as to cause a treatment part of the treatment tool to appear in the visual field range of an image taken by the endoscope, separately from operation of the treatment tool. Therefore, it becomes possible to perform treatment operation even by one surgeon. Moreover, since the back-and-forth movement transmission mechanism has a configuration that mechanically interlocks the treatment tool and the endoscope, it is possible to form a system that makes the endoscope follow the treatment tool in a simple configuration at low cost.

In a medical instrument guiding device according to another aspect of the present invention, a mode can be configured such that the back-and-forth movement transmission mechanism includes: a treatment tool-side rotation member which is provided as the rotation member, and is configured to rotate in interlock with the back-and-forth movement of the treatment tool; and an endoscope-side rotation member which is configured to rotate in interlock with rotation of the treatment tool-side rotation member and to move the endoscope back and forth.

According to this aspect, the treatment tool-side rotation member rotates when the treatment tool moves back and forth, and the endoscope-side rotation member rotates in interlock with the rotation. When the endoscope-side rotation member rotates, the endoscope moves back and forth in interlock with the rotation. Therefore, the endoscope moves back and forth in interlock with the back-and-forth movement of the treatment tool.

In a medical instrument guiding device according to another aspect of the present invention, a mode can be configured such that the endoscope-side rotation member is directly in contact and coupled with the treatment tool-side rotation member and rotates in interlock with the rotation of the treatment tool-side rotation member.

According to this aspect, the interlocking between the treatment tool-side rotation member and the endoscope-side rotation member can be performed through an arbitrary interlocking mechanism. However, like this aspect, it is possible to achieve downsizing of the medical instrument guiding device by making the treatment tool-side rotation member and the endoscope-side rotation member contact with each other so as to interlock them without a special interlocking mechanism. Thus, it is possible to achieve diameter reduction of a part of the medical instrument guiding device which is tapped into the body wall.

In a medical instrument guiding device according to further another aspect of the present invention, a mode can be configured such that a rotation axis of the treatment tool-side rotation member and a rotation axis of the endoscope-side rotation member are disposed in a direction orthogonal to a plane parallel to an axis of the treatment tool insertion hole and an axis of the endoscope insertion hole.

According to this aspect, irrespective of a case where the axis of the endoscope insertion hole and the axis of the treatment tool insertion hole are parallel or nonparallel (three-dimensionally intersect) with each other, it is possible to dispose the treatment tool-side rotation member and the endoscope-side rotation member, setting a direction orthogonal to a plane parallel to those axes as the direction of the rotation axis of the treatment tool-side rotation member and the rotation axis of the endoscope-side rotation member.

In a medical instrument guiding device according to yet further another aspect of the present invention, a mode can be configured such that a rotation axis of the treatment tool-side rotation member and a rotation axis of the endoscope-side rotation member three-dimensionally intersect (a twisted positional relationship is provided).

Like this aspect, the directions of the rotation axis of the treatment tool-side rotation member and the rotation axis of the endoscope-side rotation member are not necessarily parallel and can be directions that three-dimensionally intersect.

In a medical instrument guiding device according to yet further another aspect of the present invention can be configured such that a rotation axis of the rotation member is disposed in parallel to a plane which contacts with an outer peripheral surface of the treatment tool and an outer peripheral surface of the endoscope from one identical direction.

According to this aspect, since the endoscope and the treatment tool can be interlocked with each other even by one rotation member, it is possible to reduce the number of parts and achieve the downsizing and diameter reduction of the medical instrument guiding device.

In a medical instrument guiding device according to yet further another aspect of the present invention, a mode can be configured such that an axis of the treatment tool insertion hole and an axis of the endoscope insertion hole are disposed in nonparallel with each other; and a rotation axis of the rotation member is disposed in a direction orthogonal to a plane which is parallel to the axis of the treatment tool insertion hole and the axis of the endoscope insertion hole.

Like this aspect, in a case where the axis of the treatment tool insertion hole and the axis of the endoscope insertion hole are nonparallel, for example, in the case of a medical instrument guiding device that guides a side-viewing type endoscope into a body cavity, it is possible to dispose a rotation member, setting a direction orthogonal to a plane parallel to those treatment tool insertion hole axis and endoscope insertion hole axis as the direction of the rotation axis.

In a medical instrument guiding device according to yet further another aspect of the present invention, a mode can be configured such that the treatment tool includes an operation part, an insertion part and a treatment part; the insertion part includes a large diameter part having a first outer diameter and a small diameter part having a second outer diameter which is smaller than the first outer diameter; and the rotation member contacts with the large diameter part and rotates according to the back-and-forth movement of the treatment tool, and does not contact with the small diameter part nor rotate according to the back-and-forth movement of the treatment tool.

According to this aspect, it is possible to provide an allowance in which the rotation member does not move in interlock with the back-and-forth movement of the treatment tool. Therefore, when a surgeon performs treatment using the treatment tool or the like, it is possible to prevent the endoscope from moving back and forth in response to slight back-and-forth movement of the treatment tool in an extent that the treatment tool does not go out of the visual field of the endoscope. Therefore, it is possible to prevent an imaging range of the endoscope from varying according to the slight movement of the treatment tool, thereby avoiding disadvantage that makes the image difficult to perform treatment for a surgeon.

In a medical instrument guiding device according to yet further another aspect of the present invention, a mode can be configured such that the treatment tool insertion hole further includes an allowance generation member, and the rotation member transmits the back-and-forth movement of the treatment tool to the endoscope through the allowance generation member.

Also in this aspect, it is possible to provide an allowance in which the rotation member is not interlocked with the back-and-forth movement of the treatment tool. That is, it is possible to provide an allowance of the back-and-forth movement transmission mechanism in which the endoscope is not interlocked with the back-and-forth movement of the treatment tool.

In a medical instrument guiding device according to yet further another aspect of the present invention, a mode can be configured such that the endoscope insertion hole further includes an allowance generation member, and the rotation member transmits the back-and-forth movement of the treatment tool to the endoscope through the allowance generation member.

Also in this aspect, it is possible to provide an allowance in which the rotation member is not interlocked with the back-and-forth movement of the treatment tool. That is, it is possible to provide an allowance of the back-and-forth movement transmission mechanism in which the endoscope is not interlocked with the back-and-forth movement of the treatment tool.

In a medical instrument guiding device according to yet further another aspect of the present invention, a mode can be configured such that an allowance generation member is provided between the treatment tool-side rotation member and the endoscope-side rotation member.

Also in this aspect, it is possible to provide an allowance in which the rotation member is not interlocked with the back-and-forth movement of the treatment tool. That is, it is possible to provide an allowance of the back-and-forth movement transmission mechanism in which the endoscope is not interlocked with the back-and-forth movement of the treatment tool.

According to the present invention, it is possible to obtain an image desired by a surgeon in a simple configuration.

DETAILED DESCRIPTION OF THE EMBODIMENTS

In the following, preferred embodiments of the present invention are described in detail according to the accompanying drawings.

<<Configuration of Endoscopic Surgical Device>>

Figure 1:
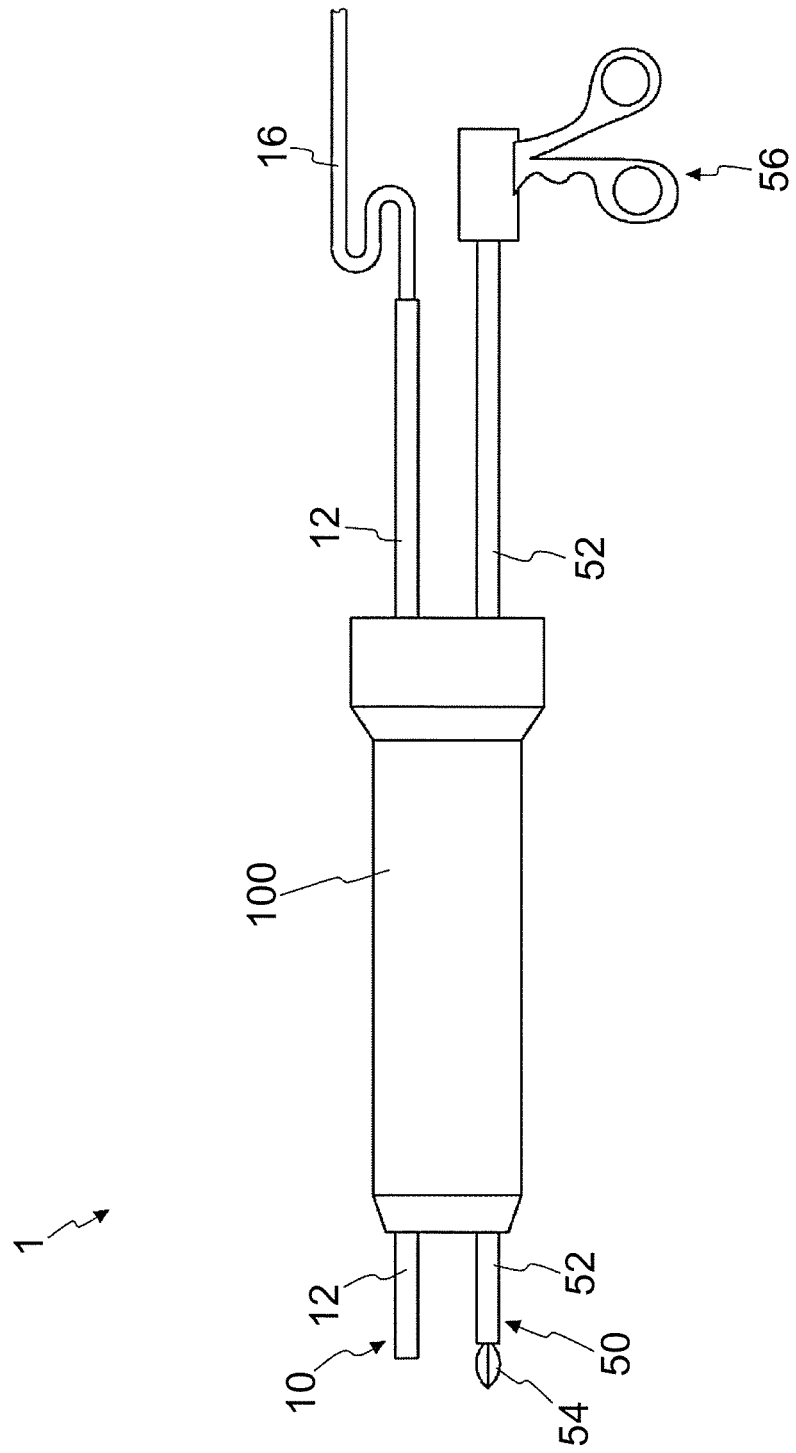
FIG. 1 is a schematic configuration diagram of an endoscopic surgical device.

FIG. 1 is a schematic configuration diagram of an endoscopic surgical device.

An endoscopic surgical device 1 is formed including an endoscope 10 which is to be inserted into patient's body cavity to observe the inside of the body cavity, a treatment tool 50 which is to be inserted into patient's body cavity to perform necessary treatment, and an outer tube 100 (medical instrument guiding device) which guides the endoscope 10 and the treatment tool 50 into patient's body cavity.

<Endoscope>

Figure 2:
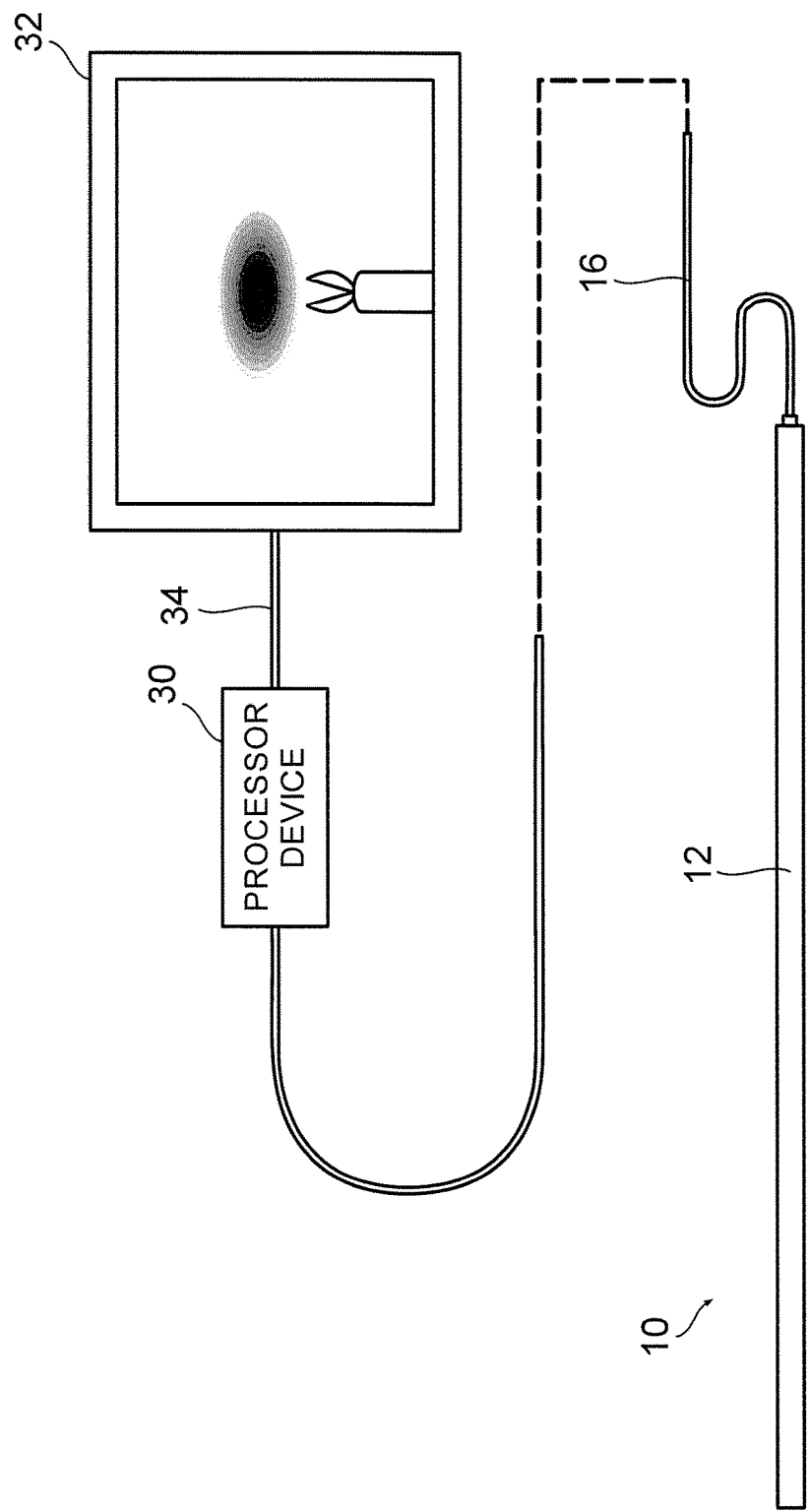
FIG. 2 is a schematic configuration diagram of an endoscope system.

FIG. 2 is a schematic configuration diagram of an endoscope system.

The endoscope 10 is an electronic endoscope, and forms an endoscope system together with a processor device 30 and a monitor 32.

The endoscope 10 used in the endoscopic surgical device 1 of the present embodiment is a rigid endoscope such as a laparoscope. The endoscope 10 has a hollow round rod-shaped insertion part 12 (endoscope insertion part 12).

Figure 3:
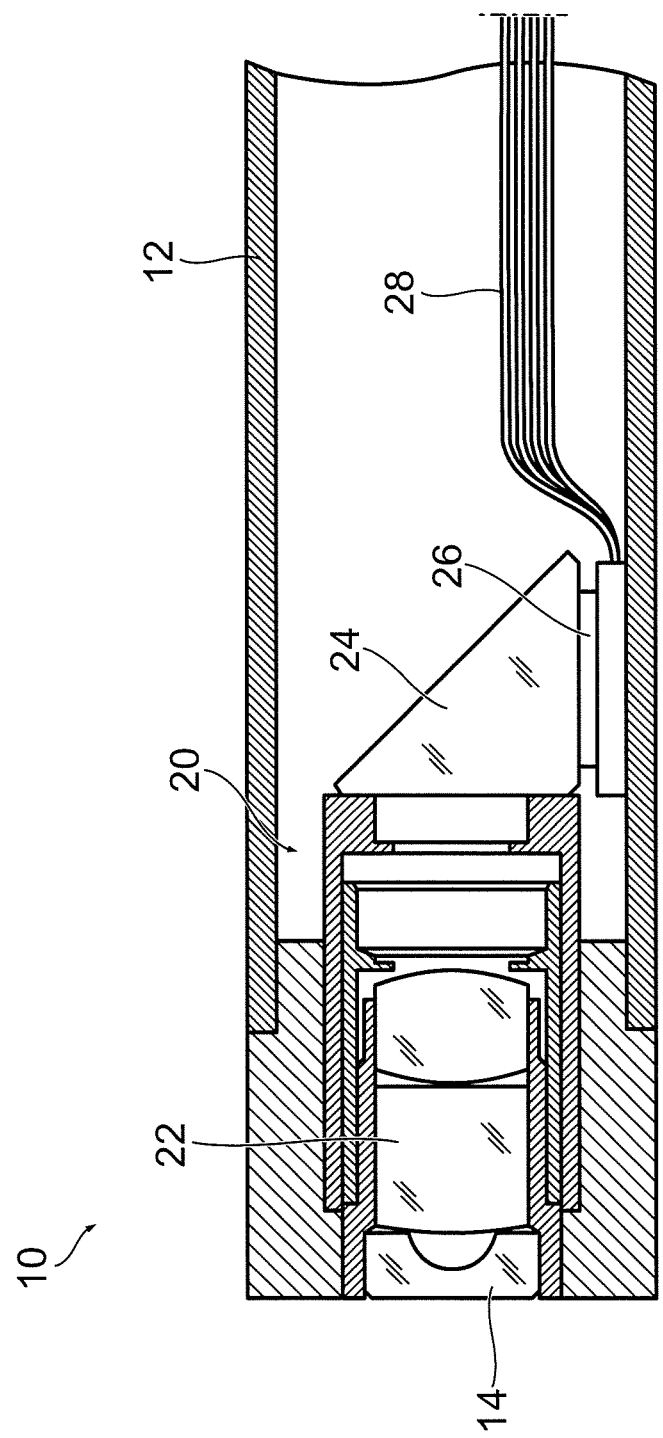
FIG. 3 is a cross-sectional view illustrating a schematic configuration in the distal end part of an endoscope insertion part.

The endoscope insertion part 12 has an observation window 14 in the distal end (see FIG. 3). The endoscope 10 observes the inside of the body cavity from the observation window 14 in the distal end of this insertion part 12.

FIG. 3 is a cross-sectional view illustrating a schematic configuration of the inside of the distal end part of the endoscope insertion part.

As illustrated in FIG. 3, an imaging device 20 is built in the distal end part of the endoscope insertion part 12. An image observed from the observation window 14 is taken by this imaging device 20.

The imaging device 20 is formed including a lens group 22, a prism 24, an imaging element 26 (a CCD (Charge Coupled Device) and a CMOS (Complementary Metal Oxide Semiconductor), and so on), and so on.

Object light that enters from the observation window 14 is reflected by the prism 24 at a substantially right angle after passing through the lens group 22, and enters into the light receiving surface of the imaging element 26. By this means, an image observed from the observation window 14 is taken by the imaging element 26.

Various signal lines 28 connected with the imaging device 20 are arranged inside the endoscope insertion part 12 and drawn out from the proximal end part of the endoscope insertion part 12.

The processor device 30 in FIG. 2 is a device that controls the whole of the endoscope system in an integral manner. The processor device 30 is connected with the endoscope 10 through an endoscope cable 16 that extends from the proximal end of the endoscope insertion part 12. Moreover, it is connected with the monitor 32 through a monitor cable 34.

Electric power and control signals for operating the imaging device 20 are transmitted from the processor device 30 to the endoscope 10. On the other hand, an image signal output from the imaging device 20 is transmitted from the endoscope 10 to the processor device 30.

The processor device 30 processes the image signal obtained from the endoscope 10 and outputs the processed signal to the monitor 32. Consequently, the image of the inside of the body cavity observed through the observation window 14 of the endoscope 10, is displayed on the monitor 32.

Note that illumination means is not included in the endoscope 10 of this example. Illumination is performed by another means, for example, needle light. The diameter of the endoscope insertion part can be made a small by omitting the illumination means to be built in the endoscope. Consequently, the diameter of the outer tube 100 can be also made small, and it is possible to reduce invasion applied to patient's body wall. However, what includes the illumination means as the endoscope 10 may be used.

Here, the endoscope 10 of this example has a configuration including the imaging device 20 in the distal end part of the endoscope insertion part 12. Alternatively, the endoscope may have a configuration including the imaging device 20 in the proximal end part of the endoscope insertion part 12. That is, the endoscope may have a configuration in which an image observed through the observation window 14 is transmitted by a relay lens or the like and taken by an imaging device arranged in the proximal end part of the endoscope insertion part 12.

<Needle Light>

Figure 4:
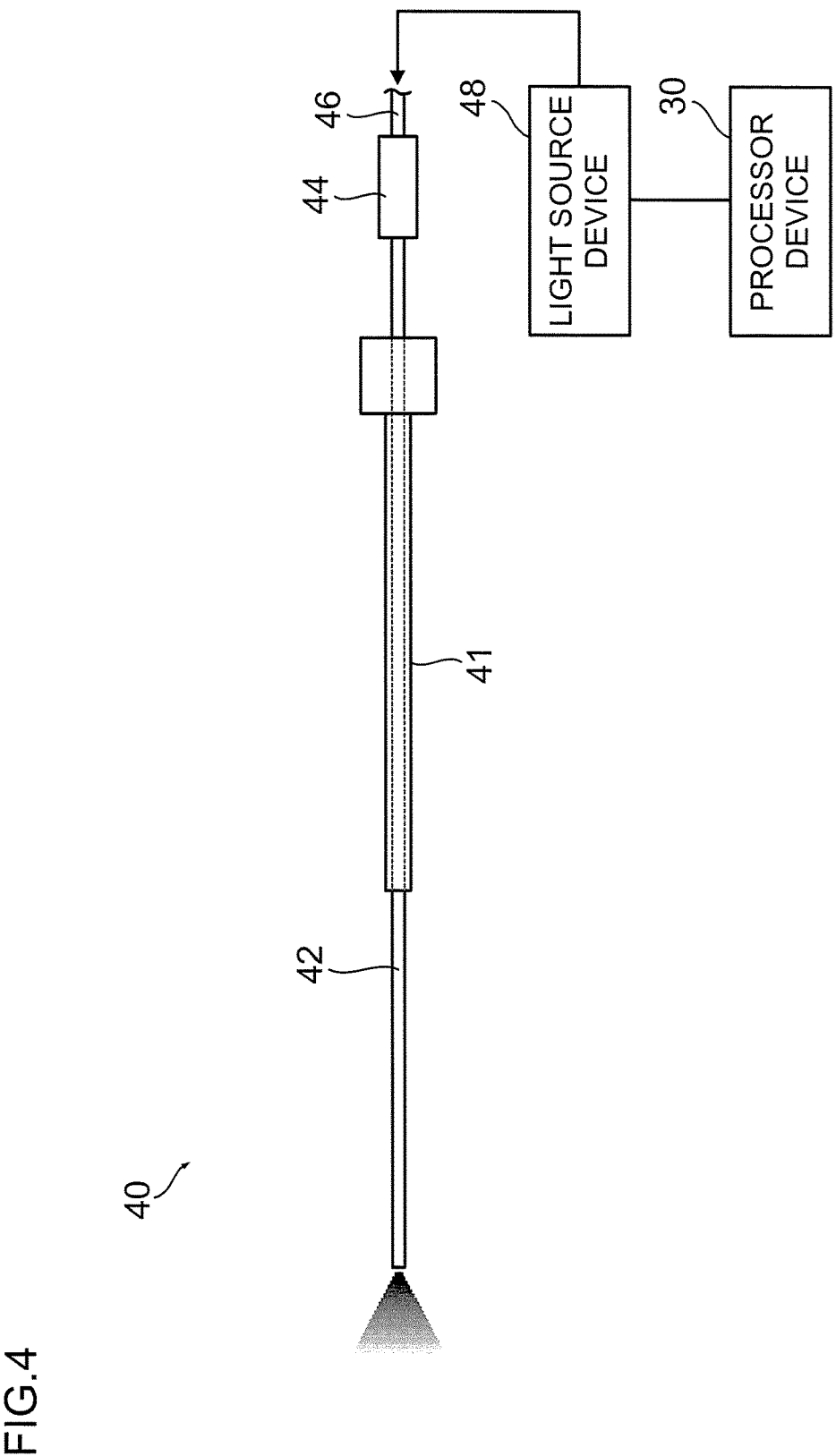
FIG. 4 is a schematic configuration diagram illustrating one example of needle light.

FIG. 4 is a schematic configuration diagram illustrating one example of needle light.

Needle light 40 is inserted in patient's body cavity and irradiates the inside of the body cavity with an illumination light.

The needle light 40 has a round rod-shaped insertion part 42. An illumination window (not illustrated) is included in the distal end of the insertion part 42, and the illumination light is irradiated from this illumination window in the axial direction. An optical fiber bundle that transmits the illumination light irradiated from the illumination window is housed in the insertion part 42.

A connection unit 44 is included in the proximal end of the needle light 40. A needle light cable 46 having flexibility is connected with the connection unit 44, and a light source device 48 is connected through this needle light cable 46. The illumination light to be emitted from the illumination window is supplied from this light source device 48. Here, the light source device 48 is connected with the processor device 30 through a cable, and the light intensity and the like are controlled.

As one example, the needle light 40 is inserted in a body cavity through a needle light outer tube 41.

<Treatment Tool>

Figure 5:
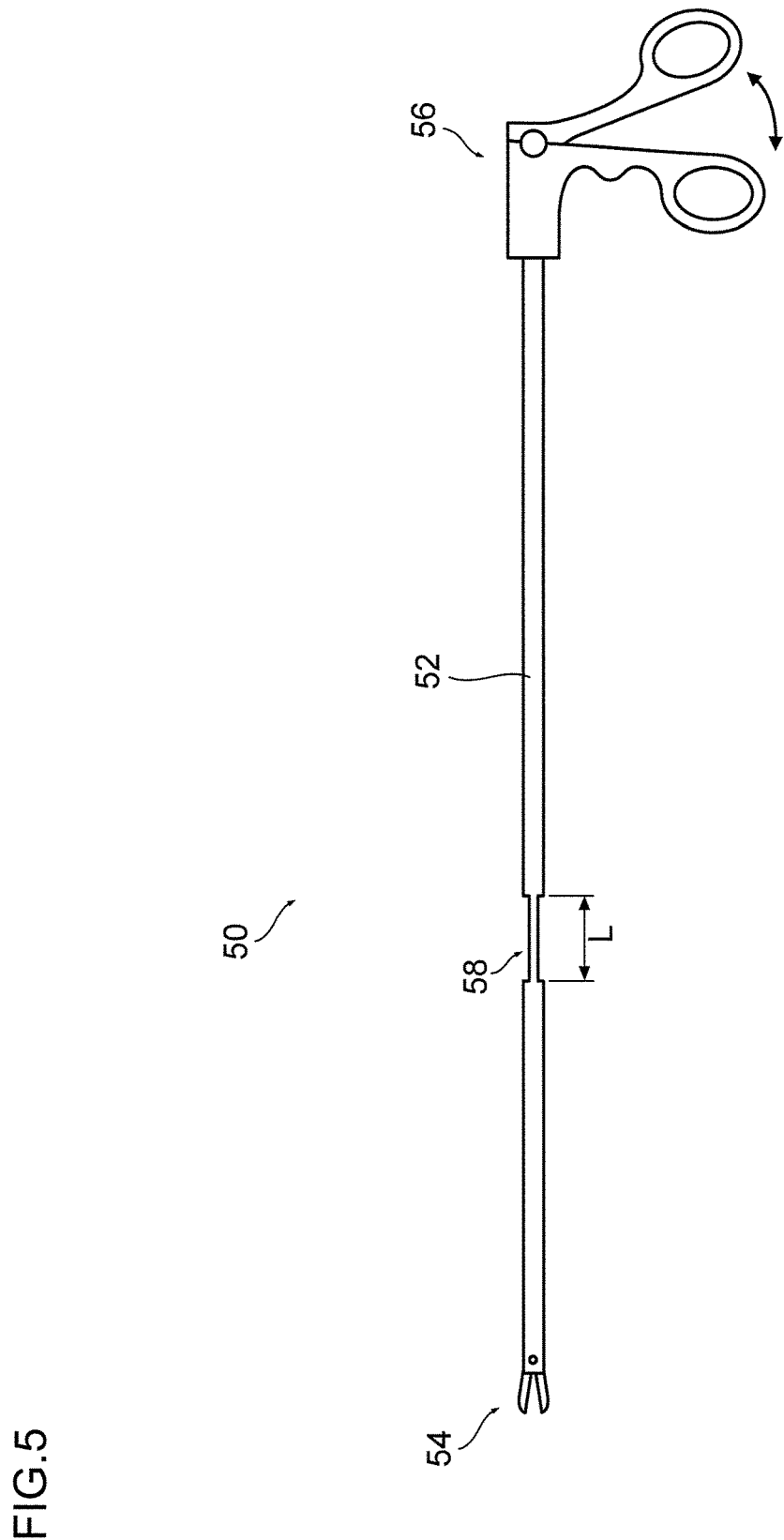
FIG. 5 is a schematic configuration diagram illustrating one example of a treatment tool.

FIG. 5 is a schematic configuration diagram illustrating one example of a treatment tool.

The treatment tool 50 includes a straight rod-shaped insertion part 52 (treatment tool insertion part 52) to be inserted in a body cavity, a treatment part 54 arranged in the distal end of the treatment tool insertion part 52, and a handle part (operation part) 56 arranged in the proximal end of the treatment tool insertion part 52. The treatment part 54 illustrated in FIG. 5 is assumed to have a scissors structure, and the treatment part 54 is operated to open and close by the opening and closing operation of the handle part 56.

Moreover, the treatment tool insertion part 52 has a reduced diameter part (small diameter part) 58 in a partial range in a direction along the central axis. The reduced diameter has an outer diameter which is made smaller than the back and forth of that partial range. The operation of the reduced diameter part 58 is described later.

Here, the treatment tool 50 is not limited to this, and a forceps, a laser probe, a suture instrument, a radio knife, a needle holder and an ultrasonic aspirator, and so on, can be used as a treatment tool.

<Outer Tube>

The outer tube 100 illustrated in FIG. 1 is tapped into patient's body cavity wall. The endoscope 10 and the treatment tool 50 are inserted into the outer tube so that the endoscope 10 and the treatment tool 50 are guided into patient's body cavity.

Figure 6:
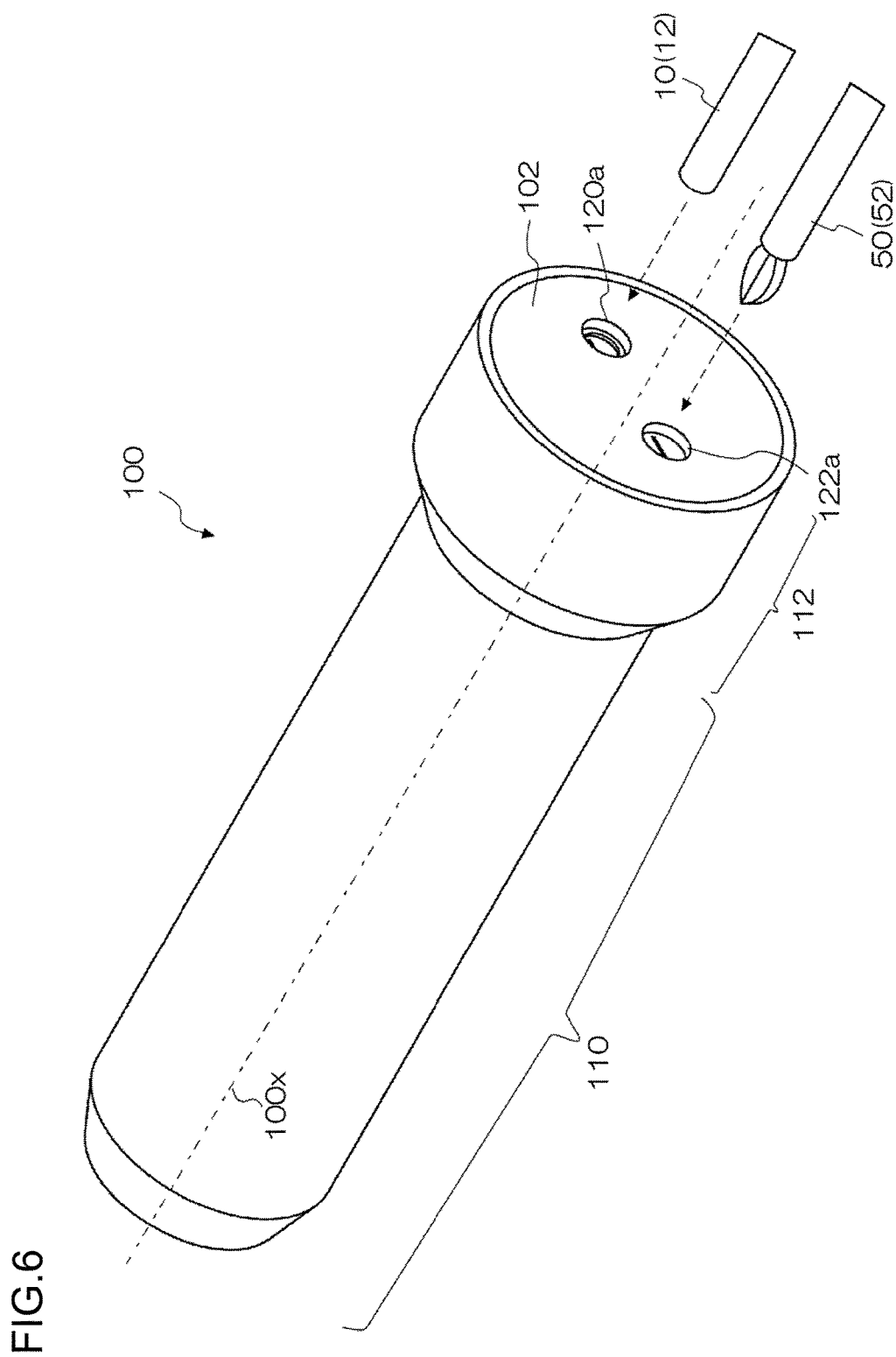
FIG. 6 is a rear perspective view of an outer tube.
Figure 7:
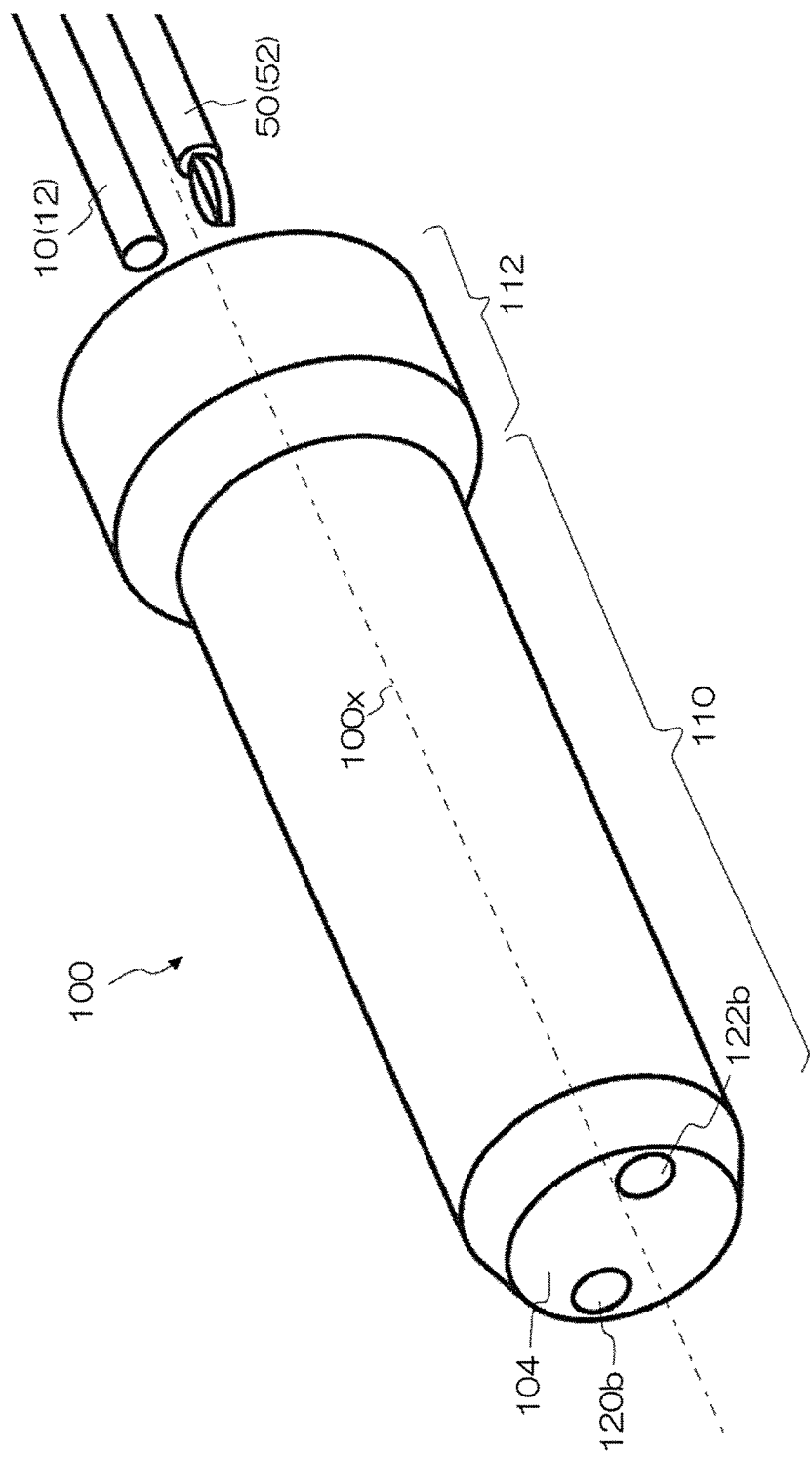
FIG. 7 is a front perspective view of the outer tube.

FIG. 6 is a rear perspective view illustrating the proximal side of the outer tube 100, and FIG. 7 is a perspective view illustrating the distal side of the outer tube 100. As illustrated in these figures and FIG. 1, the outer tube 100 is formed into a columnar shape having longitudinal axis 100x that is to be an insertion direction (front and rear direction) into a body cavity as the central axis. The outer tube 100 includes an insertion part 110 on a distal side which can be inserted into a body cavity wall (body wall) and a body cavity, and a head part 112 on a proximal side whose diameter is made larger than the insertion part 110 and which is to be disposed outside the body.

Moreover, a circular proximal end surface 102 orthogonal to the longitudinal axis 100x is formed in the proximal end of the head part 112. The proximal end surface 102 is provided with: an endoscope entry port 120a through which the insertion part 12 (endoscope insertion part 12) of the endoscope 10 is inserted into the outer tube 100; and a treatment tool entry port 122a through which the insertion part 52 (treatment tool insertion part 52) of the treatment tool 50 is inserted into the outer tube 100.

On the other hand, a circular distal end surface 104 orthogonal to the longitudinal axis 100x is formed in the distal end of the insertion part 110. The distal end surface 104 is provided with: an endoscope exit port 120b through which the endoscope insertion part 12 inserted from the endoscope entry port 120a is delivered to the outside of the outer tube 100; and a treatment tool exit port 122b through which the treatment tool insertion part 52 inserted from the treatment tool entry port 122a is delivered to the outside of the outer tube 100.

Figure 8:
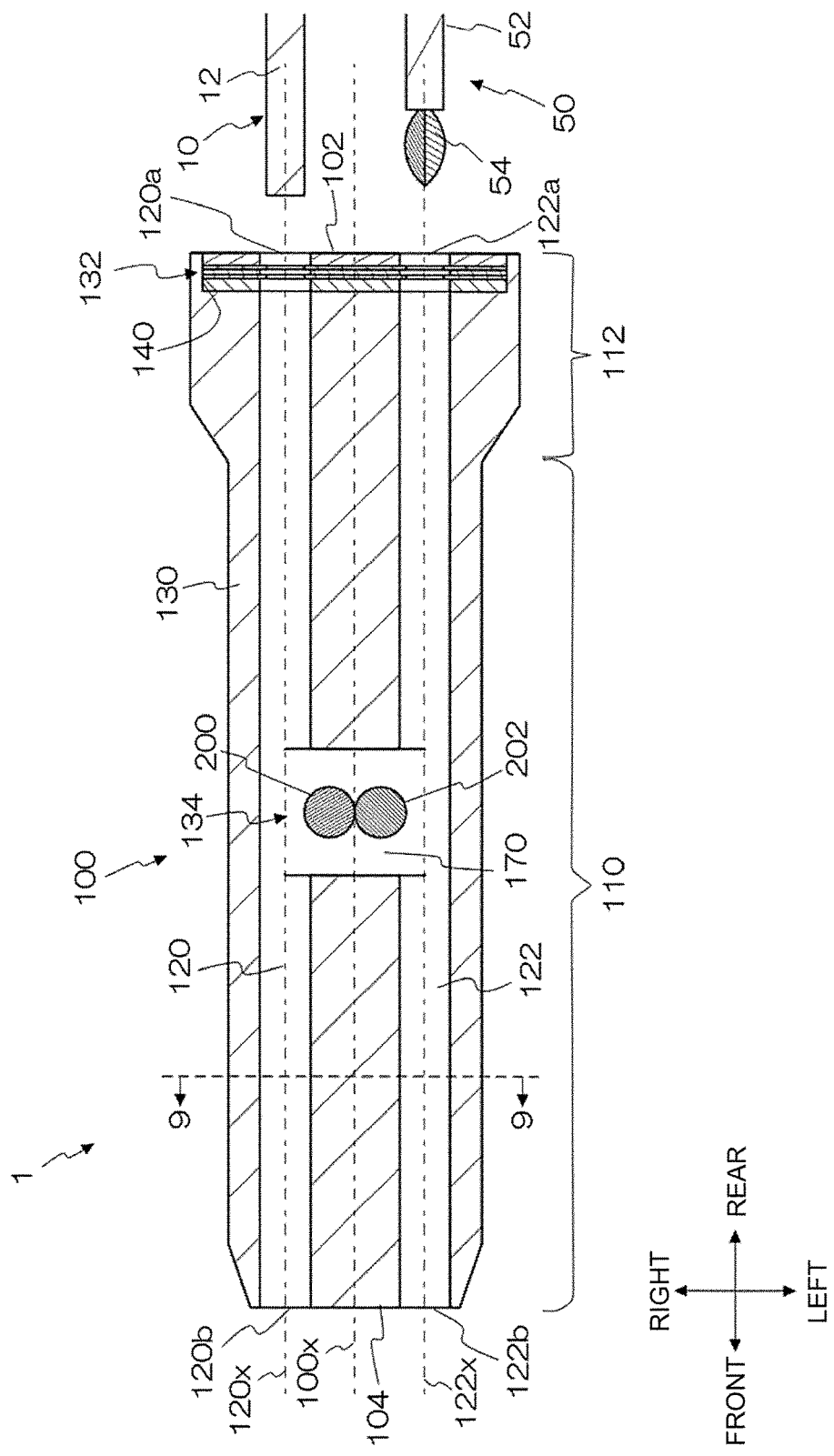
FIG. 8 is a side cross-sectional view of the outer tube.

FIG. 8 is a side cross-sectional view of the outer tube 100. As illustrated in the figure, the outer tube 100 is formed including an outer tube body 130, as a guide member, which forms the substantially whole of the outer tube 100, a valve member 132 installed on the proximal end side of the outer tube 100 (the proximal end of the head part 112) and an interlocking mechanism 134 installed inside the outer tube 100 (inside the insertion part 110).

The outer tube body 130 is a main member of the outer tube 100 to form and hold a necessary space inside the outer tube 100, and, for example, forms a non-space part inside the outer tube 100 with metal such as stainless steel and aluminum or a material having rigidity such as rigid plastic. Here, the outer tube body 130 may not be formed in an integral manner, and it may be formed by connecting multiple members.

A columnar concave portion 140 is formed in the proximal end of the outer tube body 130, and the columnar valve member 132 is fitted and fixed to the concave portion 140. By this means, the valve member 132 is disposed on the proximal end side of the outer tube 100. The proximal end surface 102 of the outer tube 100 is formed by the valve member 132 and the end surface of the outer tube body 130 that covers the surroundings of the valve member 132.

Figure 9:
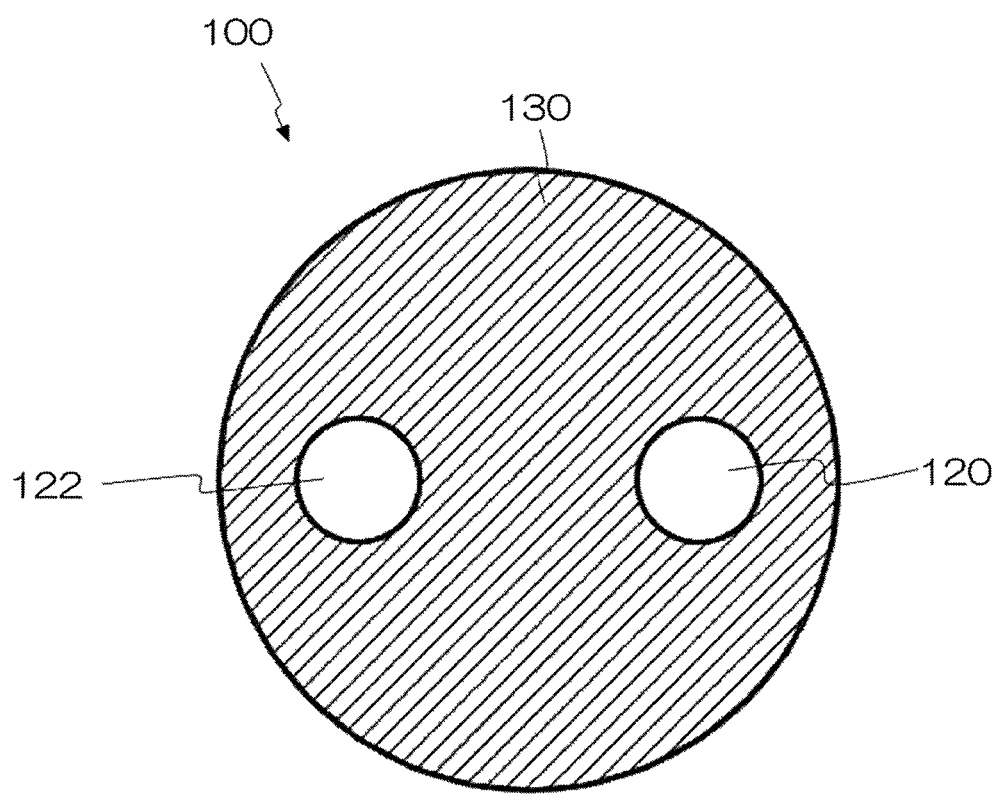
FIG. 9 is a cross-sectional view of arrow 9-9 in FIG. 8.

As illustrated in FIG. 9 which illustrates the cross-section of arrow 9-9 in FIG. 8, an endoscope insertion hole 120 having an endoscope insertion axis 120x parallel to the longitudinal axis 100x as a central axis and a treatment tool insertion hole 122 having a treatment tool insertion axis 122x parallel to the longitudinal axis 100x and the endoscope insertion axis 120x as a central axis are formed inside the outer tube body 130.

The endoscope insertion hole 120 forms a lumen (conduit line) having cross-sectional circular shape whose diameter is slightly larger than the outer diameter (diameter) of the endoscope insertion part 12 which is to be guided into a body cavity by the outer tube 100. The distal end side of the endoscope insertion hole 120 extends up to the distal end surface 104 of the outer tube 100 and forms the above-mentioned endoscope exit port 120b on the distal end surface 104.

On the other hand, the proximal end side of the endoscope insertion hole 120 is formed up to the proximal end surface of the outer tube body 130 (the bottom surface of the concave portion 140). Further, the endoscope insertion hole 120 communicates from the outer tube body 130 and extends to the valve member 132 to form the above-mentioned endoscope entry port 120a on the proximal end surface 102 of the outer tube 100.

Thus, the endoscope insertion hole 120 into which the endoscope 10 (endoscope insertion part 12) can be inserted so as to be freely movable back and forth is provided in the outer tube 100. When the endoscope insertion part 12 is inserted from the endoscope entry port 120a of the proximal end surface 102 of the outer tube 100, the endoscope insertion part 12 is guided to the endoscope insertion hole 120 while passing through a position in which the central axis of the endoscope insertion part 12 substantially overlaps with the endoscope insertion axis 120x that is the central axis of the endoscope insertion hole 120, and the endoscope insertion part 12 is delivered from the endoscope exit port 120b of the distal end surface 104 of the outer tube 100.

Similarly, the treatment tool insertion hole 122 forms a lumen having a cross-sectional circular shape whose diameter is slightly larger than the outer diameter (diameter) of the treatment tool insertion part 52 which is to be guided into a body cavity by the outer tube 100. The distal end side of the treatment tool insertion hole 122 extends up to the distal end surface 104 of the outer tube 100 and forms the above-mentioned treatment tool exit port 122b on the distal end surface 104.

On the other hand, the proximal end side of the treatment tool insertion hole 122 is formed up to the proximal end side of the outer tube body 130 (the bottom surface of the concave portion 140). Further, the treatment tool insertion hole 122 communicates from the outer tube body 130, extends to the valve member 132 and forms the above-mentioned treatment tool entry port 122a on the proximal end surface 102 of the outer tube 100.

Thus, the treatment tool insertion hole 122 into which the treatment tool 50 (treatment tool insertion part 52) can be inserted so as to be freely movable back and forth is provided in the outer tube 100. When the treatment tool insertion part 52 is inserted from the treatment tool entry port 122a of the proximal end surface 102 of the outer tube 100, the treatment tool insertion part 52 is guided to the treatment tool insertion hole while passing through a position in which the central axis of the treatment tool insertion part 52 substantially overlaps with the treatment tool insertion axis 122x of the treatment tool insertion hole 122, and the treatment tool insertion part 52 is delivered from the treatment tool exit port 122b of the distal end surface 104 of the outer tube 100.

Here, FIGS. 8 and 9 assume that the endoscope insertion hole 120 and the treatment tool insertion hole 122 have substantially the same diameter, and the endoscope insertion axis 120x and the treatment tool insertion axis 122x are disposed in positions where substantially the same distance apart from the longitudinal axis 100x. However, the configuration is not necessarily limited to this.

In FIG. 8, the valve member 132 fixed to the concave portion 140 in the proximal end of the outer tube body 130 is provided to prevent insufflation gas (such as carbon dioxide gas) which is fed into a body cavity by, for example, an insufflation device to inflate the inside of the body cavity from leaking to the outside of the body through the endoscope insertion hole 120 and the treatment tool insertion hole 122.

Figure 10:
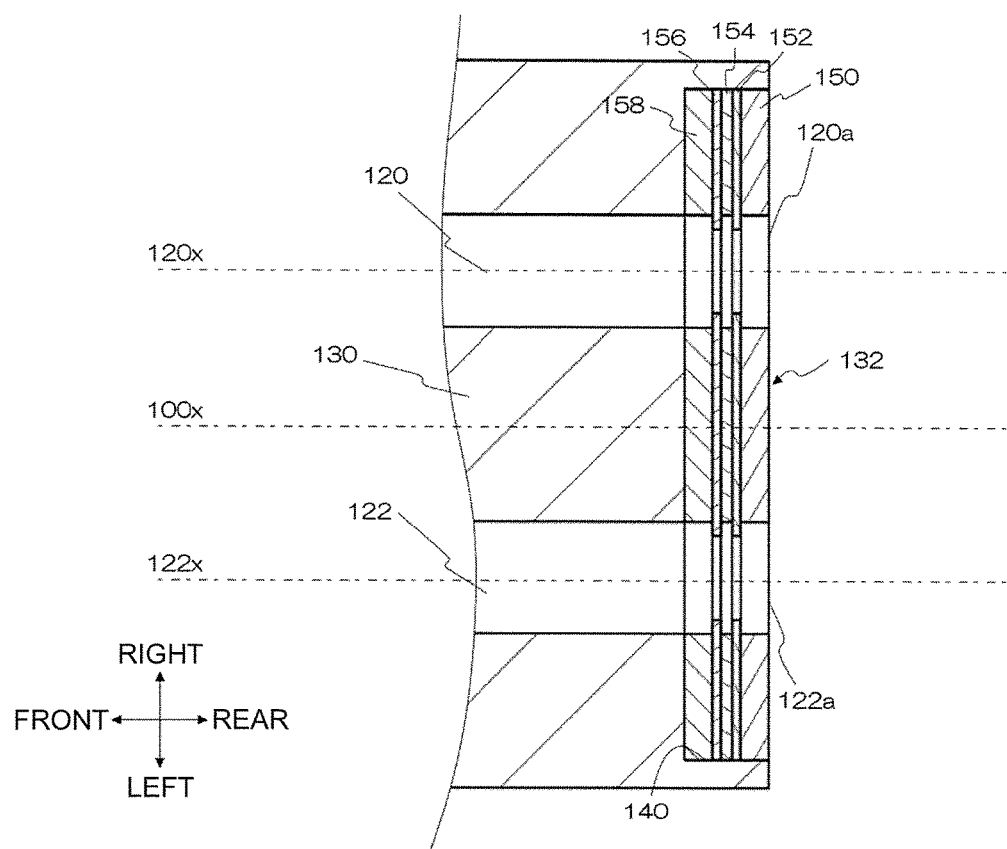
FIG. 10 is an enlarged view that enlarges a peripheral part of a valve member in FIG. 8.
Figure 11:
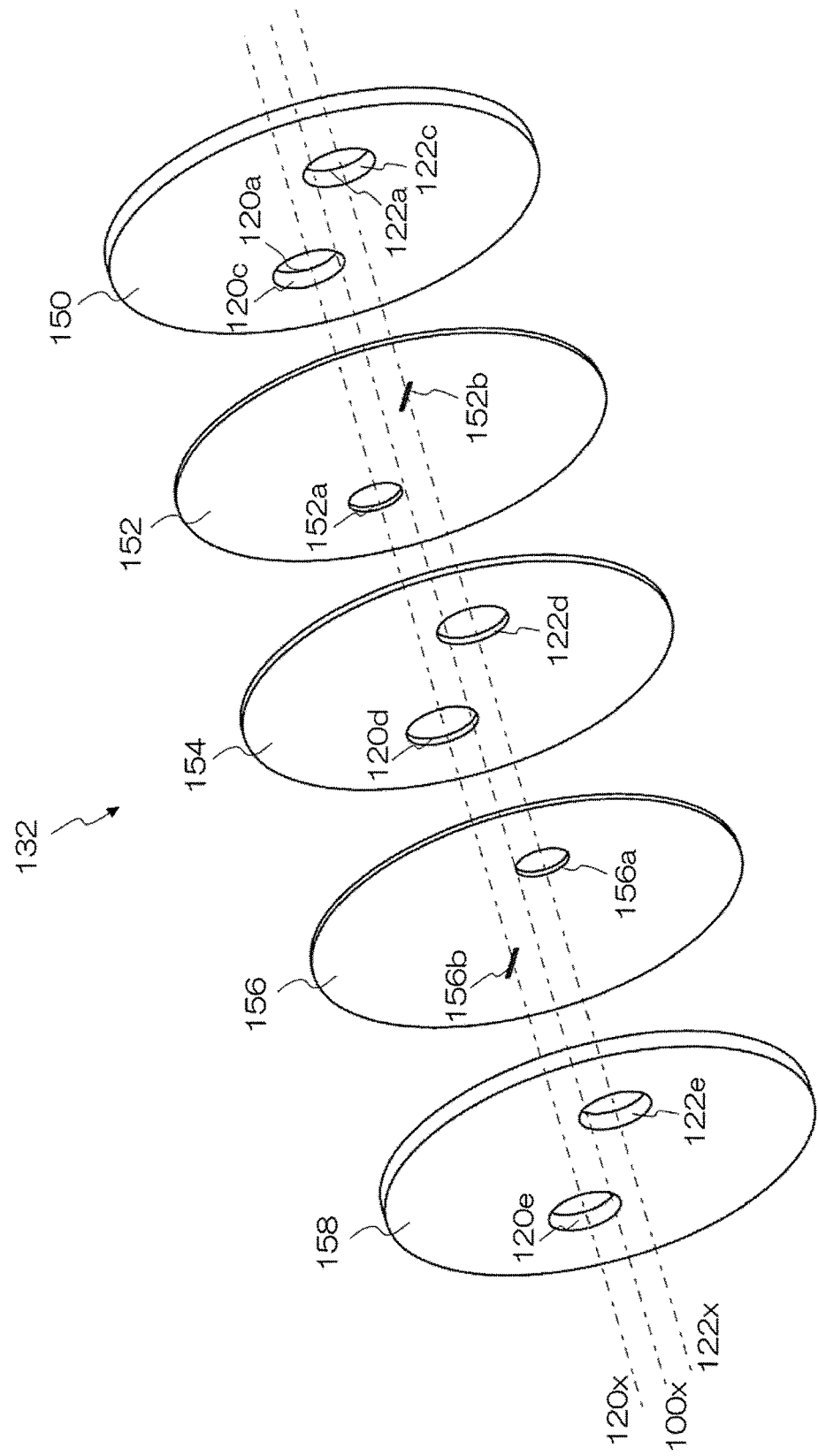
FIG. 11 is an exploded perspective view illustrating a schematic configuration of the valve member.

FIG. 10 is an enlarged view that enlarges the peripheral part of the valve member 132 in FIG. 8, and FIG. 11 is am exploded perspective view illustrating the schematic configuration of the valve member 132.

As illustrated in these figures, the valve member 132 is configured to include a proximal side holding member 150, a first valve body 152, an intermediate member 154, the second valve body 156 and a distal side holding member 158 in this order from the proximal end side to the distal end side along the longitudinal axis 100x.

These members 150 to 158 are circular plate-shaped members having the same outer diameter (disc-shaped members), are disposed integrally overlaid on the same axis to form the valve member 132, and then are attached to the outer tube body 130 such that the axes of the members 150 to 158 overlaps with the longitudinal axis 100x.

The proximal side holding member 150, the intermediate member 154 and the distal side holding member 158 are formed with metal such as stainless steel and aluminum or a material having rigidity such as rigid plastic, and serve a function to reinforce the first valve body 152 and the second valve body 156 which are sandwiched between them.

Moreover, holes 120c to 120e and 122c to 122e (see FIG. 11) forming the above-mentioned endoscope insertion hole 120 and treatment tool insertion hole 122 are formed in the proximal side holding member 150, the intermediate member 154 and the distal side holding member 158. The central axis of the holes 120c to 120e is disposed in a position that overlaps with the endoscope insertion axis 120x, and the central axis of the holes 122c to 122e is disposed in a position that overlaps with the treatment tool insertion axis 122x. Here, the proximal surface of the proximal side holding member 150 forms the proximal end surface 102 of the outer tube 100, and the openings in the proximal ends of the holes 120c and 122c of the proximal side holding member 150 form the above-mentioned endoscope entry port 120a and treatment tool entry port 122a.

Both the first valve body 152 and the second valve body 156 are formed to be elastically deformable by a material having elasticity such as natural rubber, synthetic rubber and silicone rubber.

An endoscope opening type airtight valve portion 152a and a treatment tool slit type airtight valve portion 152b (see FIG. 11) are formed in the first valve body 152.

The endoscope opening type airtight valve portion 152a is a circular opening whose inner diameter is slightly smaller than the outer diameter of the endoscope insertion part 12, and the center of the opening is disposed on the endoscope insertion axis 120x. Therefore, when the endoscope insertion part 12 is stuck in the endoscope opening type airtight valve portion 152a, the fringe of the opening coheres to the outer peripheral surface of the endoscope insertion part 12. By this means, when the endoscope insertion part 12 is inserted in the endoscope insertion hole 120, a gap formed between the endoscope insertion part 12 and the endoscope insertion hole 120 is sealed.

The treatment tool slit type airtight valve portion 152b is formed as one straight slit having a predetermined length, and the center of the slit is disposed on the treatment tool insertion axis 122x. When the treatment tool insertion part 52 is removed from the treatment tool insertion hole 122, this treatment tool slit type airtight valve portion 152b blocks the treatment tool insertion hole 122.

A treatment tool opening type airtight valve portion 156a and an endoscope slit type airtight valve portion 156b (see FIG. 11) are formed in the second valve body 156.

The treatment tool opening type airtight valve portion 156a is a circular opening whose inner diameter is slightly smaller than the outer diameter of the treatment tool insertion part 52, and the center of the opening is disposed on the treatment tool insertion axis 122x. Therefore, when the treatment tool insertion part 52 is stuck in the treatment tool opening type airtight valve portion 156a, the fringe of the opening coheres to the outer peripheral surface of the treatment tool insertion part 52. By this means, when the treatment tool insertion part 52 is inserted in the treatment tool insertion hole 122, the gap formed between the treatment tool insertion part 52 and the treatment tool insertion hole 122 is sealed.

The endoscope slit type airtight valve portion 156b is formed as one straight slit having a predetermined length, and the center of the slit is disposed on the endoscope insertion axis 120x. When the endoscope insertion part 12 is removed from the endoscope insertion hole 120, this endoscope slit type airtight valve portion 156b blocks the endoscope insertion hole 120.

According to the valve member 132 configured as above, when the endoscope 10 (endoscope insertion part 12) and the treatment tool 50 (treatment tool insertion part 52) are inserted in the outer tube 100, the airtightness of the outer tube 100 is secured by the endoscope opening type airtight valve portion 152a and the treatment tool opening type airtight valve portion 156a. Moreover, when the endoscope insertion part 12 and the treatment tool insertion part 52 are not inserted in the outer tube 100, the airtightness of the outer tube 100 is secured by the endoscope slit type airtight valve portion 156b and the treatment tool slit type airtight valve portion 152b.

In FIG. 8, the interlocking mechanism 134 is provided near the center of a range in the back-and-forth direction of the outer tube body 130. The interlocking mechanism 134 is a back-and-forth movement transmission mechanism that, when the treatment tool insertion part 52 inserted in the treatment tool insertion hole 122 is moved to advance or retract (back-and-forth movement) by a surgeon, moves the endoscope insertion part 12 inserted in the endoscope insertion hole 120 to advance or retract (back-and-forth movement) through a rotation member that rotates in interlock with that movement. The configuration is described later. According to this interlocking mechanism 134, the visual field range (a position in the back-and-forth direction of viewpoint) of the endoscope 10 is changed so as to keep the position and size of the treatment part 54 in a taken image of the endoscope 10 constant according to a position in the back-and-forth direction of the treatment part 54 provided in the distal end of the treatment tool 50. Therefore, it is not necessarily needed to perform an operation for adjusting the visual field range of the endoscope 10 while operating the treatment tool 50, and, even if a scopist does not exist, one surgeon can perform surgery only by operating the treatment tool 50 while seeing a taken image of the endoscope 10.

Figure 34:
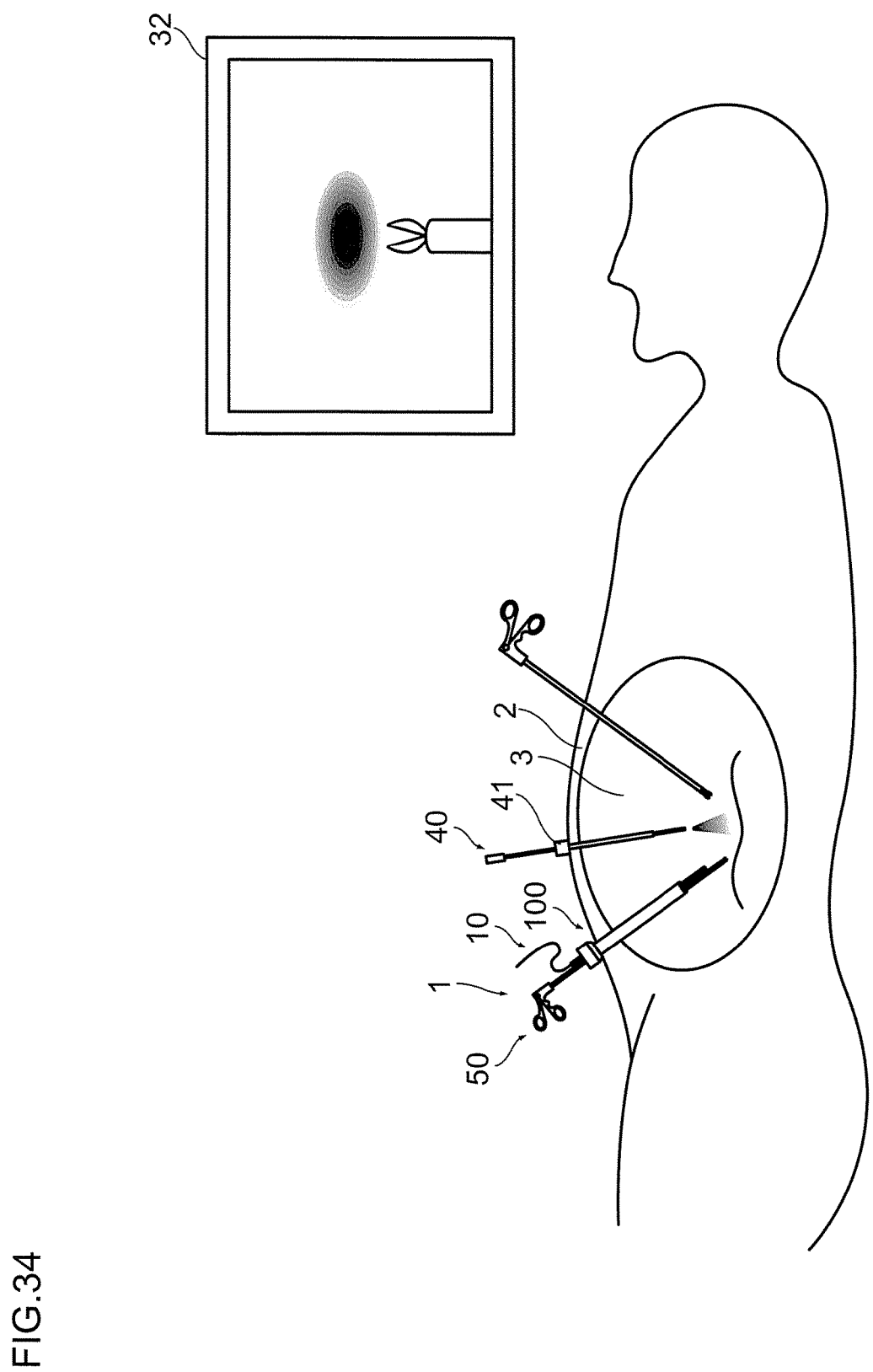
FIG. 34 is a schematic diagram illustrating a use mode of an endoscopic surgical device using an outer tube including an interlocking mechanism.

Here, FIG. 34 is a schematic diagram illustrating a use mode of the endoscopic surgical device 1 using the outer tube 100 including such the interlocking mechanism 134. As illustrated in the figure, the endoscope 10 and the treatment tool 50 are inserted into a body cavity 3 through the outer tube 100 which is tapped into patient's body cavity wall (body wall) 2. The endoscope 10 moves back and forth by the interlocking mechanism 134 when the surgeon moves the treatment tool 50 to advance or retract (back-and-forth movement), and the endoscope 10 tilts together with the outer tube 100 when the treatment tool 50 is tilted. Therefore, it is possible to make the visual field range of the endoscope 10 follow the treatment part 54, and an image of a treatment part (treatment part 54) is always displayed on the monitor 32.

Moreover, since illumination means is not included in the endoscope 10, the needle light 40 is used as illumination means. The needle light 40 is inserted in the body cavity 3 through the outer tube 41 for needle light. The body cavity 3 is illuminated by an illumination light emitted from the distal end of the needle light 40. Here, in this example, a case where one needle light 40 is used has been exemplified, but multiple pieces of the needle light 40 may be used according to the necessity. Moreover, a case where the endoscope 10 includes illumination means and does not use the needle light 40 is also possible.

Thus, according to the endoscopic surgical device 1 of the present embodiment, since the endoscope 10 is operated by the operation of the treatment tool 50, it is possible to perform treatment by one surgeon. That is, the scopist becomes unnecessary. Moreover, since the endoscope 10 and the treatment tool 50 are inserted in the body cavity 3 through the outer tube 100, only one tap place is required in order to insert the endoscope 10 and the treatment tool 50 into the body cavity. By this means, it is possible to perform surgery of low invasion.

Moreover, the interlocking mechanism 134 of the outer tube 100 is configured to have an allowance in which the endoscope insertion part 12 does not move back and forth in response to slight back-and-forth movement of the treatment tool insertion part 52. For example, when the surgeon operates the treatment part 54 of the treatment tool 50 and performs treatment, there is a case where slight back-and-forth movement (variation in a position in the back-and-forth direction) may be intentionally or non-intentionally caused in the treatment tool insertion part 52 (treatment part 54). If the endoscope insertion part 12 synchronously moves by the interlocking mechanism 134 in response to such the slight back-and-forth movement, a taken image (visual field range) of the endoscope 10 moves as a whole and it becomes difficult to perform treatment. For example, if the treatment part 54 moves back and forth to the extent that the treatment part 54 does not move out of the visual field range of the endoscope 10, there is a case where treatment can be easily performed when the endoscope 10 is not synchronously moved and stays still. Therefore, the allowance is provided in the interlocking mechanism 134 to prevent unnecessary following movement of the endoscope insertion part 12.

In the following, the interlocking mechanism 134 that applies the first to third embodiments is sequentially described as a specific mode of the interlocking mechanism 134.

Interlocking Mechanism of First Embodiment

Figure 12:
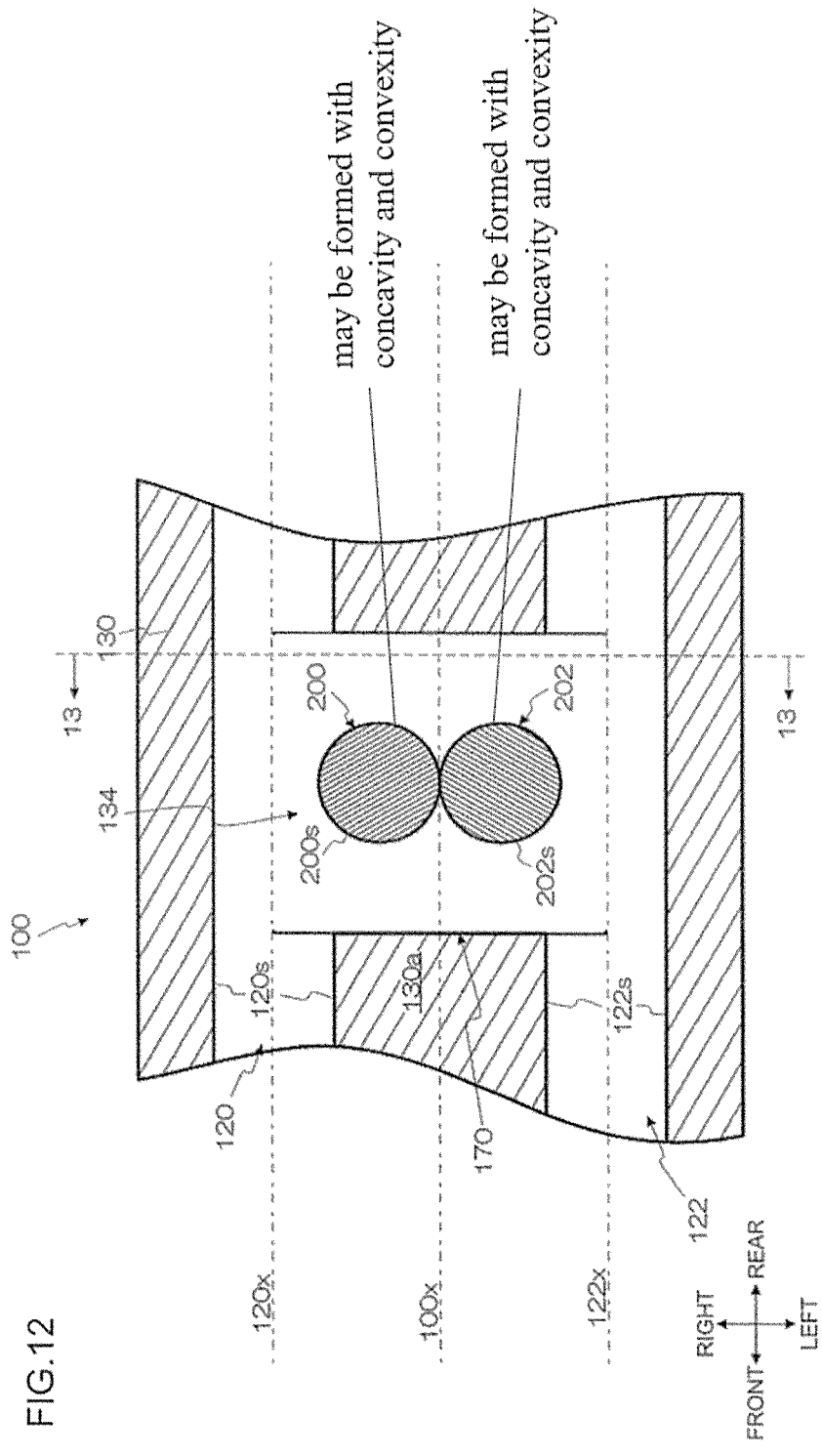
FIG. 12 is an enlarged view that enlarges a peripheral part of an interlocking mechanism in FIG. 8.
Figure 13:
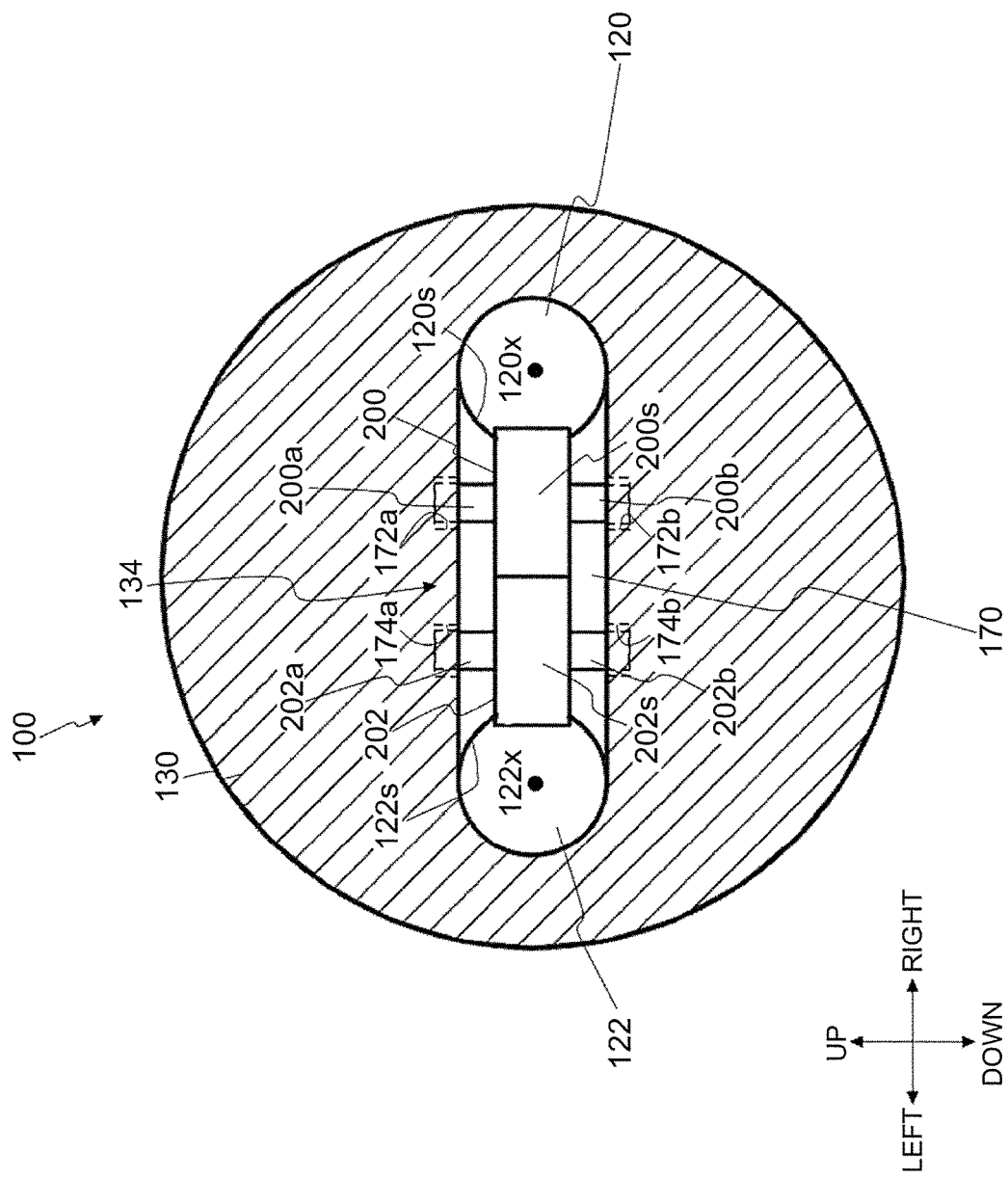
FIG. 13 is a cross-sectional view of arrow 13-13 in FIG. 12.
Figure 14:
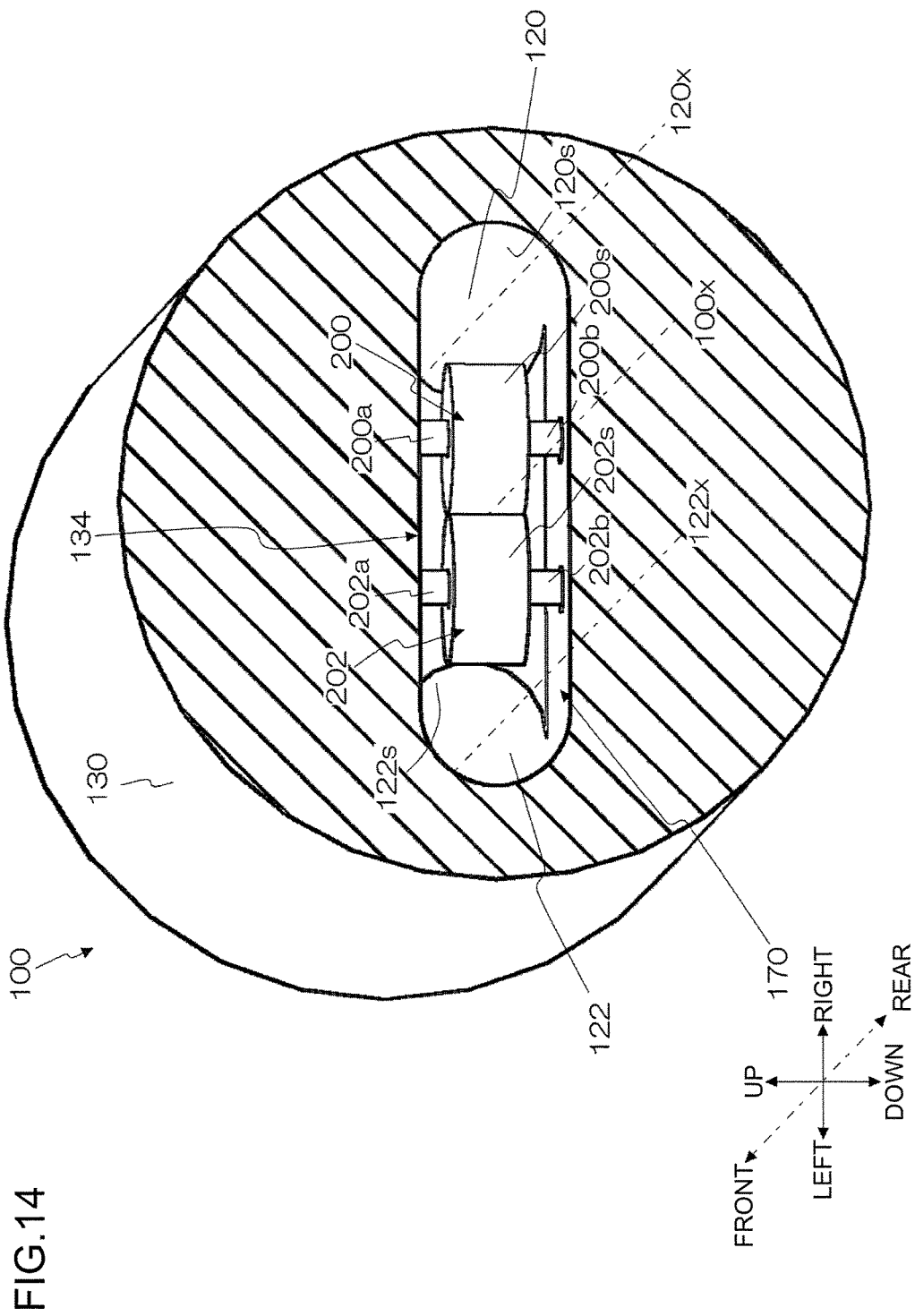
FIG. 14 is a perspective view diagonally illustrating a cross section in FIG. 13.

First, regarding the description of the interlocking mechanism 134 of the first embodiment, FIG. 8 illustrates the configuration of the interlocking mechanism 134 of the first embodiment, FIG. 12 is an enlarged view of the peripheral part of the interlocking mechanism 134 in FIG. 8, and FIG. 13 is a cross-sectional view along arrow 13-13 in FIG. 12. Moreover, FIG. 14 is a perspective view diagonally illustrating the cross section in FIG. 13.

As illustrated in these figures, a cavity part 170 is provided inside the outer tube body 130 in order to dispose the interlocking mechanism 134.

The cavity part 170 is formed so as to penetrate from an inner peripheral surface 120s of the endoscope insertion hole 120 to an inner peripheral surface 122s of the treatment tool insertion hole 122, and, for example, has a shape in which a partition wall portion 130a of the outer tube body 130 included in a predetermined distance range in a direction orthogonal to the plane of a rectangular with the endoscope insertion axis 120x and the treatment tool insertion axis 122x as opposite sides is cut out.

Here, the endoscope insertion axis 120x and the treatment tool insertion axis 122x are disposed in parallel as mentioned above, and it is assumed that a plane including them is a horizontal reference surface (a plane which includes the endoscope insertion axis 120x and is parallel to the treatment tool insertion axis 122x). Then, it is assumed that, while the longitudinal axis 100x is assumed to be the back-and-forth direction, a direction orthogonal to the horizontal reference surface is the up-and-down direction and a direction which is horizontal to the horizontal reference surface and orthogonal to the longitudinal axis 100x is the right-and-left direction. Here, the longitudinal axis 100x is disposed on the same plane as the horizontal reference surface in the present embodiment, but the relationship between the horizontal reference surface and the longitudinal axis 100x is not limited to this.

On the other hand, as illustrated in FIGS. 12 to 14, the interlocking mechanism 134 of the first embodiment includes an endoscope-side roller 200 (endoscope-side rotation member) and a treatment tool-side roller 202 (treatment tool-side rotation member) which and disposed side by side in the right-and-left direction in the cavity part 170. The endoscope-side roller 200 is disposed on the side of the endoscope insertion hole 120 and the treatment tool-side roller 202 is disposed on the side of the treatment tool insertion hole 122.

These endoscope-side roller 200 and treatment tool-side roller 202 are columnar members having cylindrical surfaces (outer peripheral surfaces 200s and 202s) of the same diameter, and their central axes (rotation axes) are disposed so as to be orthogonal to the horizontal reference surface. That is, respective central axes of the endoscope-side roller 200 and the treatment tool-side roller 202 are disposed in a direction orthogonal to a plane parallel to both the endoscope insertion axis 120x and the treatment tool insertion axis 122x.

Axis pins 200a, 200b, 202a and 202b that extend along the central axes (rotation axes) of the endoscope-side roller 200 and the treatment tool-side roller 202 (outer peripheral surfaces 200s and 202s) are provided in each of the end surfaces on both upper and lower sides of the endoscope-side roller 200 and the treatment tool-side roller 202 (see FIGS. 13 and 14).

Meanwhile, a pair of engagement holes 172a and 172b disposed in opposite positions and a pair of engagement holes 174a and 174b are formed on the upper and lower wall surfaces in the cavity part 170 (see FIG. 13). Further, the axis pins 200a and 200b of the endoscope-side roller 200 are stuck in the engagement holes 172a and 172b respectively, and the axis pins 202a and 202b of the treatment tool-side roller 202 are stuck in by the engagement holes 174a and 174b respectively.

By this means, in the cavity part 170, the endoscope-side roller 200 is supported by the axis pins 200a and 200b so as to be rotatable around the central axes thereof, and the treatment tool-side roller 202 is supported by the axis pins 202a and 202b so as to be rotatable around the central axes thereof.

Here, means for supporting the endoscope-side roller 200 and the treatment tool-side roller 202 so as to be rotatable with respect to the cavity part 170 may be in any mode.

Moreover, the endoscope-side roller 200 and the treatment tool-side roller 202 may not be in a mode to perform rotation with an axis pin as mentioned above as long as they are in a mode in which they are rotatably supported. For example, they may be supported so as to be rotatable around axis members inserted in the positions of the central axes of the endoscope-side roller 200 and the treatment tool-side roller 202.

In addition, to form the cavity part 170 inside the outer tube body 130 or arrange the endoscope-side roller 200 and the treatment tool-side roller 202 in the cavity part 170, it is possible to form a partial region member of the outer tube body 130 as separate member that can be separated from the remaining region member. For example, FIG. 8 illustrates the outer tube body 130 as a cross-section cut by a horizontal reference surface, but a mode may be configured to form the outer tube body 13 with two members separated into two upper and lower regions by the horizontal reference surface. In that case, it only has to form concave portions forming the cavity part 170 in respective members, dispose the endoscope-side roller 200 and the treatment tool-side roller 202 in one concave portion and then contact and fix surfaces that are the horizontal reference surfaces of those two members.

Moreover, only a local region of the outer tube body 130 may be formed as a member that can be separated from the remaining region. In this case, a path to insert and install the endoscope-side roller 200 and the treatment tool-side roller 202 in the cavity part 170 from the outside of the outer tube body 130 is provided, and a member separated so as to block the path may be fixed after the endoscope-side roller 200 and the treatment tool-side roller 202 are installed in the cavity part 170.

As means for fixing multiple separated members, it is possible to use arbitrary means such as bonding by a bonding agent and screw lock.

The endoscope-side roller 200 and the treatment tool-side roller 202 which are disposed in the cavity part 170 in this way are disposed in positions in which their outer peripheral surfaces 200s and 202s contact with each other. By this means, it is assumed that the endoscope-side roller 200 and the treatment tool-side roller 202 are coupled by friction force and one roller rotates in interlock with the rotation of the other roller. At this time, the endoscope-side roller 200 and the treatment tool-side roller 202 rotate in opposite directions.

Figure 15:
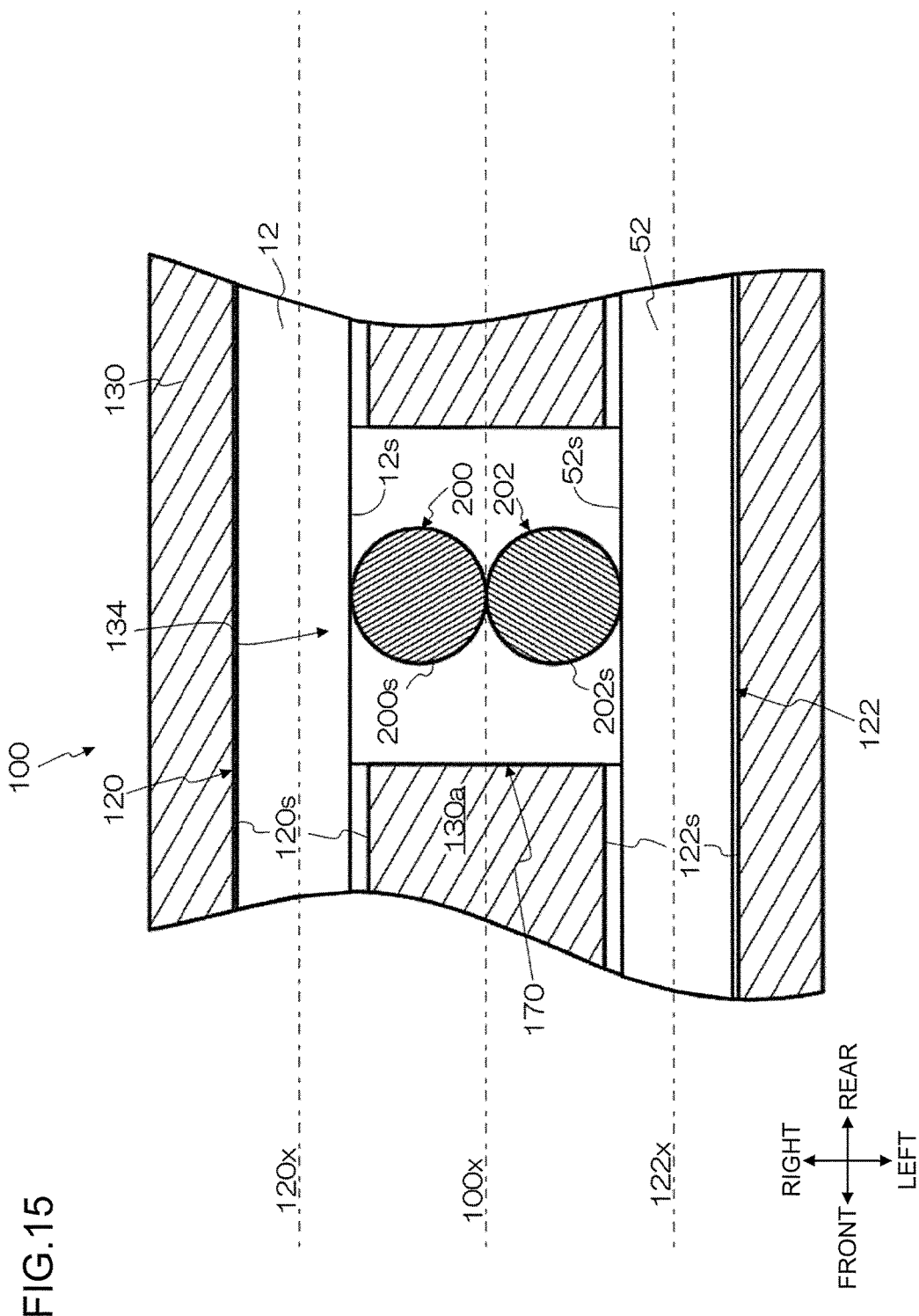
FIG. 15 is a diagram illustrating a state where an endoscope insertion part and a treatment tool insertion part are inserted in an endoscope insertion hole and a treatment tool insertion hole respectively in the enlarged view in FIG. 12.

Moreover, the endoscope-side roller 200 is disposed such that a partial range in the peripheral direction of the outer peripheral surface 200s projects into the endoscope insertion hole 120 rather than a surface position along the inner peripheral surface 120s of the endoscope insertion hole 120. By this means, as illustrated in FIG. 15, the outer peripheral surface 200s of the endoscope-side roller 200 is brought into contact with and coupled with an outer peripheral surface 12s of the endoscope insertion part 12 inserted in the endoscope insertion hole 120. FIG. 15 illustrates a state where the endoscope insertion part 12 and the treatment tool insertion part 52 are inserted in the endoscope insertion hole 120 and the treatment tool insertion hole 122 respectively in the enlarged view in FIG. 12.

Therefore, the endoscope insertion part 12 moves back and forth (back-and-forth movement) in interlock with the rotation of the endoscope-side roller 200, and the endoscope-side roller 200 rotates in interlock with the back-and-forth movement of the endoscope insertion part 12.

Figure 19:
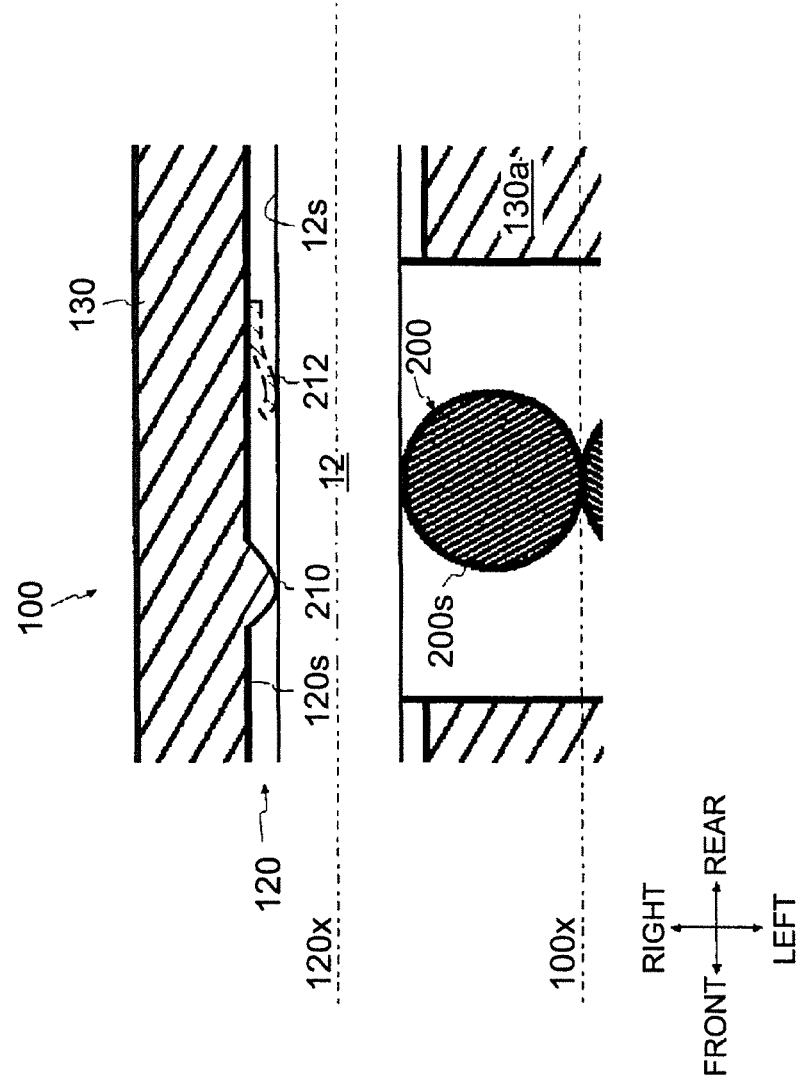
FIG. 19 is a partially enlarged diagram of FIG. 15 and is a diagram illustrating a case where a projection and an urging member are provided in the inner peripheral surface of an endoscope insertion hole.

Here, it is desirable to prevent the outer peripheral surface 12s of the endoscope insertion part 12 from being separated from the outer peripheral surface 200s of the endoscope-side roller 200. To do so, it is possible to prevent a gap from being caused between the outer peripheral surface 12s of the endoscope insertion part 12 and the inner peripheral surface 120s in a position facing the endoscope-side roller 200 of the endoscope insertion hole 120, by design conditions such as the diameter of the endoscope insertion hole 120, the position of the endoscope insertion axis 120x and the projection amount of the outer peripheral surface 200s of the endoscope-side roller 200 toward the endoscope insertion hole 120. Moreover, like FIG. 19, for example, it is possible to provide a projection 210 that prevents the endoscope insertion part 12 from being separated from the endoscope-side roller 200, or an urging member 212 such as flat spring that energizes the endoscope insertion part 12 in a direction to contact with the endoscope-side roller 200, in any position in the inner peripheral surface 120s of the endoscope insertion hole 120 such as a position facing the endoscope-side roller 200 of the inner peripheral surface 120s of the endoscope insertion hole 120 and the periphery part thereof.

On the other hand, the treatment tool-side roller 202 is disposed such that a partial range in the peripheral direction of the outer peripheral surface 202s projects into the treatment tool insertion hole 122 rather than a surface position along the inner peripheral surface 122s of the treatment tool insertion hole 122. By this means, as illustrated in FIG. 15, the outer peripheral surface 202s of the treatment tool-side roller 202 contacts with an outer peripheral surface 52s (the outer peripheral surface 52s of a non-reduced diameter part excluding the range of the reduced diameter part 58) of the treatment tool insertion part 52 inserted in the treatment tool insertion hole 122.

Therefore, the treatment tool-side roller 202 rotates in interlock with the back-and-forth movement of the treatment tool insertion part 52, and the treatment tool insertion part 52 moves back and forth in interlock with the rotation of the treatment tool-side roller 202.

Here, it is desirable to prevent the outer peripheral surface 52s of the treatment tool insertion part 52 from being separated from the outer peripheral surface 202s of the treatment tool-side roller 202. To do so, it is possible to prevent a gap from being caused between the outer peripheral surface 52s of the treatment tool insertion part 52 and the inner peripheral surface 122s in a position facing the treatment tool-side roller 202 of the treatment tool insertion hole 122, by design conditions such as the diameter of the treatment tool insertion hole 122, the position of the treatment tool insertion axis 122x and the projection amount of the outer peripheral surface 202s of the treatment tool-side roller 202 toward the treatment tool insertion hole 122. Moreover, a member that is similar to the projection 210 or the urging member 212 of the endoscope insertion hole 120 illustrated in FIG. 19 may be provided in any position in the inner peripheral surface 122s of the treatment tool insertion hole 122 such as a position facing the treatment tool-side roller 202 of the inner peripheral surface 122s of the treatment tool insertion hole 122 and the peripheral part thereof.

Moreover, the endoscope-side roller 200 and the treatment tool-side roller 202 may be integrally formed as a whole by simply plastic (synthetic resin), and so on, and, to reduce slipping between those outer peripheral surfaces 200s and 202s and a contact object, the outer peripheral surfaces 200s and 202s may be coated with a material having a large friction coefficient such as a rubber member or fine concavity and convexity for anti-slipping may be formed in the outer peripheral surfaces 200s and 202s.

Moreover, the outer peripheral surfaces 200s and 202s may be formed by winding a band member formed with a material having a large friction coefficient around the outer peripheral part of the treatment tool-side roller 202 (a result of fitting a ring-shaped member of a large friction coefficient to the outer peripheral part), or the whole of the endoscope-side roller 200 and the treatment tool-side roller 202 may be formed with a material having a large friction coefficient.

In addition, the endoscope-side roller 200 and the treatment tool-side roller 202 may be interlocked by forming toothed wheels (gears) on the outer peripheral surfaces of the endoscope-side roller 200 and the treatment tool-side roller 202 and making them engage with each other.

Moreover, any of upper and lower end surfaces (plate surfaces of a disc-shaped rotation member) of the treatment tool-side roller 202 may be brought into contact with the outer peripheral surface 52s of the treatment tool insertion part 52 to rotate the treatment tool-side roller 202 in response to the back-and-forth movement of the treatment tool insertion part 52. It is similar to the interlocking between the endoscope-side roller 200 and the endoscope insertion part 12.

According to the interlocking mechanism 134 of the first embodiment configured as above, when the treatment tool insertion part 52 inserted in the treatment tool insertion hole 122 of the outer tube 100 is moved back and forth, the treatment tool-side roller 202 of the interlocking mechanism 134 rotates in interlock with this. For example, in a case where the treatment tool insertion part 52 is moved forward, the treatment tool-side roller 202 rotates in a rotation direction (the clockwise direction in FIG. 15) in which the outer peripheral surface 202s moves forward in the contact position between the outer peripheral surface 202s of the treatment tool-side roller 202 and the outer peripheral surface 52s of the treatment tool insertion part 52.

When the treatment tool-side roller 202 rotates, the endoscope-side roller 200 rotates in a direction opposite to the treatment tool-side roller 202 in interlock with this. For example, in a case where the treatment tool insertion part 52 is moved forward, the endoscope-side roller 200 rotates in a rotation direction (the anti-clockwise direction in FIG. 15) in which the outer peripheral surface 200s moves backward in the contact position between the outer peripheral surface 200s of the endoscope-side roller 200 and the outer peripheral surface 202s of the treatment tool-side roller 202.

Further, when the endoscope-side roller 200 rotates, the endoscope insertion part 12 inserted in the endoscope insertion hole 120 moves back and forth in interlock with this. For example, in a case where the treatment tool insertion part 52 is moved forward, the endoscope insertion part 12 moves forward such that the outer peripheral surface 12s moves forward in the contact position between the outer peripheral surface 12s of the endoscope insertion part 12 and the outer peripheral surface 200s of the endoscope-side roller 200.

Thus, the endoscope insertion part 12 moves back and forth in interlock with the back-and-forth movement of the treatment tool insertion part 52, in a case where the treatment tool insertion part 52 is moved forward, the endoscope insertion part 12 also moves forward only by the same movement amount as the movement amount of the treatment tool insertion part 52. In a case where the treatment tool insertion part 52 is moved backward, the endoscope insertion part 12 also moves backward only by the same movement amount as the movement amount of the treatment tool insertion part 52. Here, in a case where a surgeon moves the endoscope insertion part 12 back and forth, the treatment tool insertion part 52 similarly moves back and forth in interlock with this.

By the way, as illustrated in FIG. 5, the treatment tool insertion part 52 is provided with a reduced diameter part (small diameter part) 58, in which an outer diameter is smaller than the front and rear of that part, in a partial range in the back-and-forth direction along the central axis. Here, in a case where a range excluding the reduced diameter part 58 of the treatment tool insertion part 52 is assumed as a non-reduced diameter part (large diameter part), the outer diameter (second outer diameter) of the reduced diameter part 58 is smaller than the outer diameter (first outer diameter) of the non-reduced diameter part.

Figure 16:
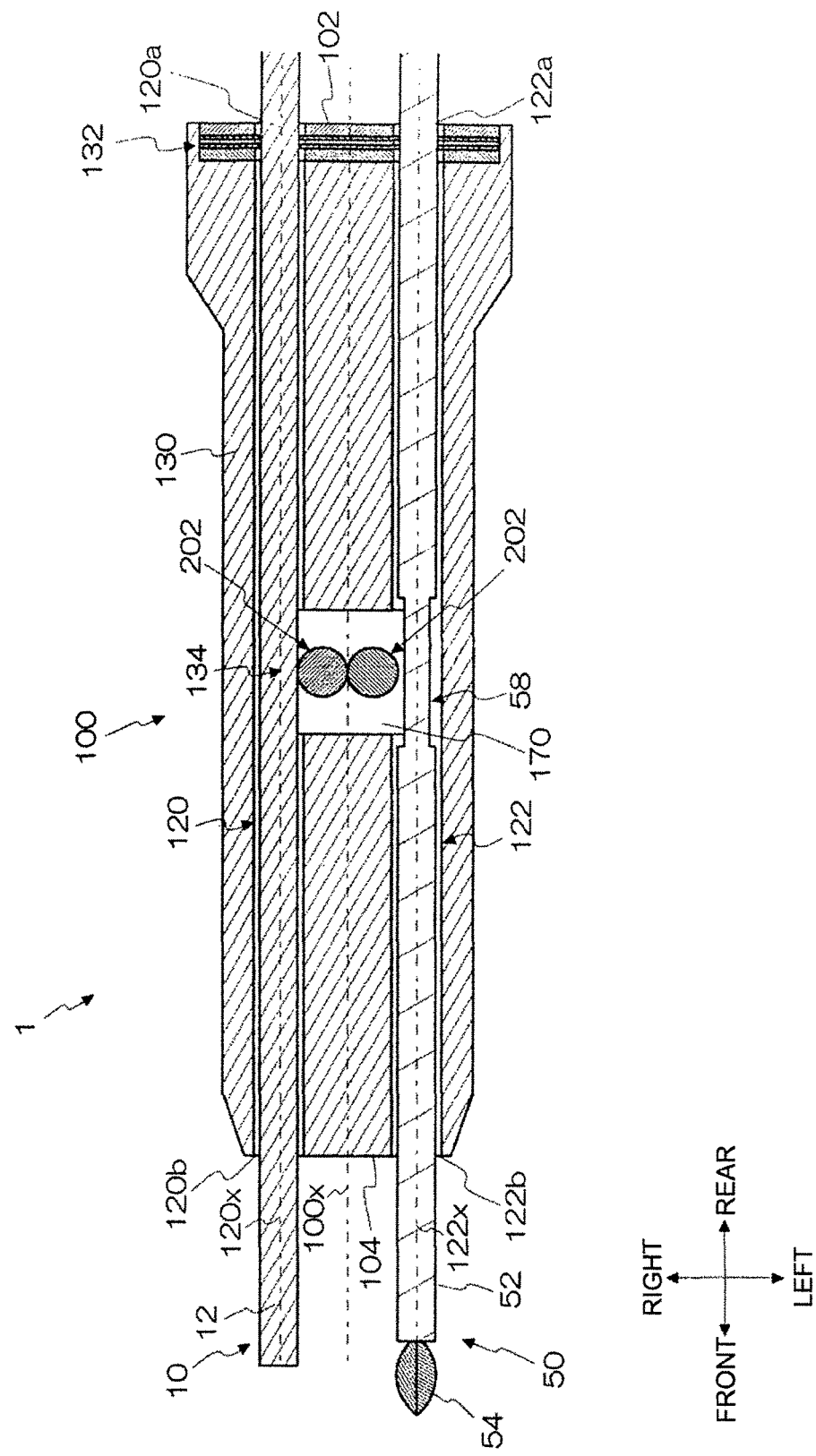
FIG. 16 is a side cross-sectional view illustrating a state where an endoscope insertion part and a treatment tool insertion part are inserted into an endoscope insertion hole and a treatment tool insertion hole respectively in the side cross-sectional view in FIG. 8.

As illustrated in the side cross-sectional view in FIG. 16 illustrating a state where the endoscope insertion part 12 and the treatment tool insertion part 52 are respectively inserted in the endoscope insertion hole 120 and the treatment tool insertion hole 122 in the side cross-sectional view in FIG. 8, the reduced diameter part 58 of the treatment tool insertion part 52 is disposed in a position facing the treatment tool-side roller 202 in a state where the treatment tool insertion part 52 is drawn out by a predetermined amount from the treatment tool exit port 122b of the outer tube 100.

At this time, since the outer peripheral surface 202s of the treatment tool-side roller 202 and the outer peripheral surface 52s of the treatment tool insertion part 52 do not contact with each other, the treatment tool-side roller 202 does not rotate in response to the back-and-forth movement of the treatment tool insertion part 52 so that the endoscope insertion part 12 does not move back and forth in interlock with the movement. That is, the treatment tool insertion part 52 is provided with, as a component of the interlocking mechanism 134, the reduced diameter part 58 to provide an allowance in which the endoscope insertion part 12 does not move back and forth (or is not interlocked) in response to the back-and-forth movement of the treatment tool insertion part 52.

For example, when the length of the reduced diameter part 58 in the back-and-forth direction of the treatment tool insertion part 52 is assumed as L and a state is assumed in which the central point of the reduced diameter part 58 is disposed in a position (the same position in the back-and-forth direction) facing the right-and-left direction with respect to the central axis of the treatment tool-side roller 202, the outer peripheral surface 202s of the treatment tool-side roller 202 does not contact with the outer peripheral surface 52s of the treatment tool insertion part 52 as long as the treatment tool insertion part 52 is moved within the range of a movement amount of L/2 or less in front or rear of that position in this state. Therefore, the endoscope insertion part 12 does not synchronously move in that movement amount range, which is the range of allowance (allowance range) of the interlocking mechanism 134.

Figure 17:
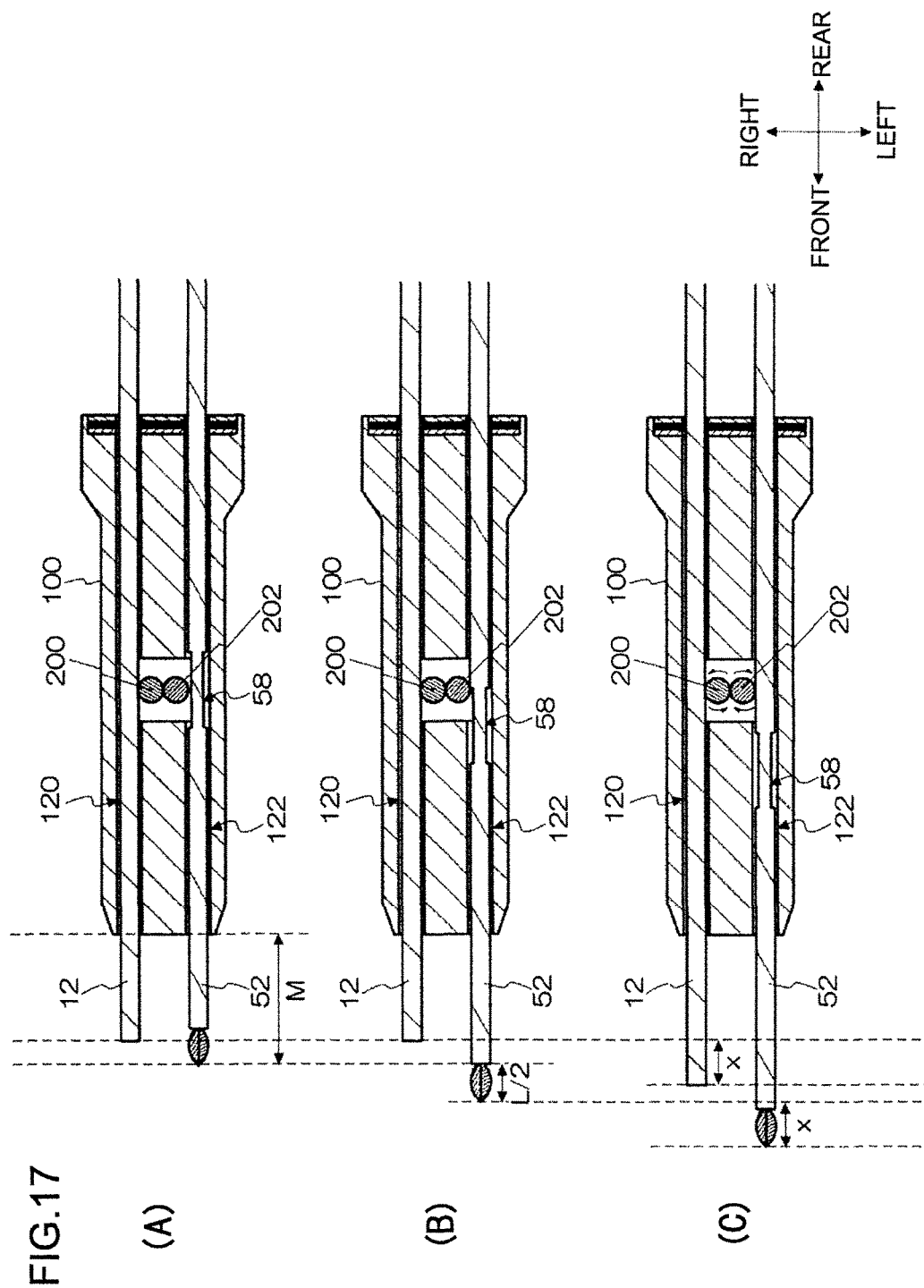
FIG. 17 is an explanatory diagram that describes the range of allowance of an interlocking mechanism.
Figure 18:
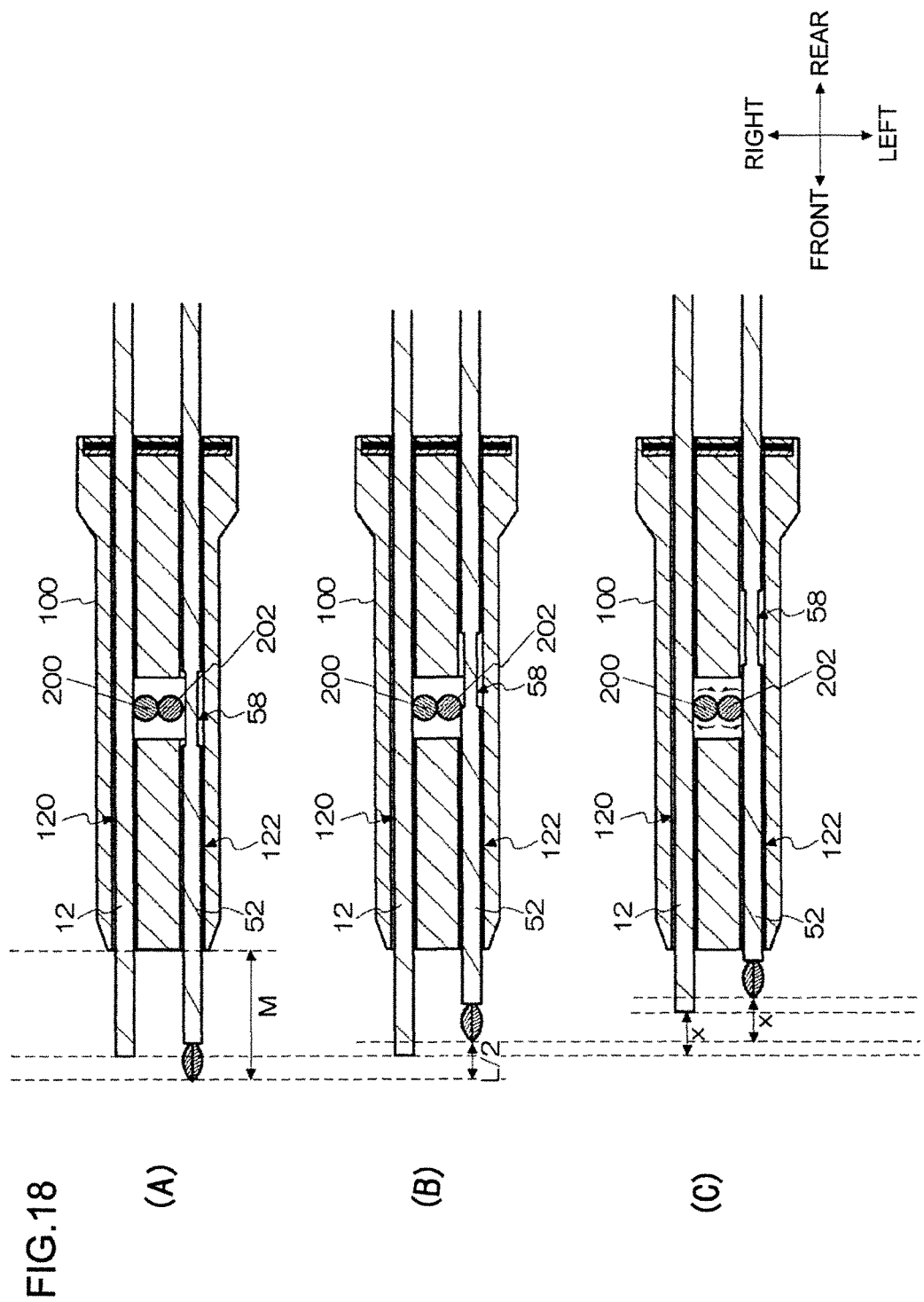
FIG. 18 is an explanatory diagram that describes the range of allowance of an interlocking mechanism.

FIGS. 17 and 18 are diagrams to describe the range of allowance of the interlocking mechanism 134.

(A) portion of FIG. 17 illustrates a state where the central point of the reduced diameter part 58 of the treatment tool insertion part 52 is disposed in the same position in the back-and-forth direction with respect to the central axis of the treatment tool-side roller 202 as mentioned above, and the delivery amount of the treatment part 54 from the distal end surface 104 (treatment tool exit port 122b) of the outer tube 100 is M.

The delivery amount from the distal end surface 104 (endoscope exit port 120b) of the outer tube 100 in the distal end of the endoscope 10 inserted in the endoscope insertion hole 120 is adjusted such that it is possible to obtain an image of a surgeon's desired visual field range, and it can be arbitrarily adjusted (details are described later).

When the treatment tool insertion part 52 in this state is moved forward to a position with a movement amount of L/2 and the treatment part 54 is moved forward only by movement amount L/2, the outer peripheral surface 52s of the treatment tool insertion part 52 does not contact with the outer peripheral surface 202s of the treatment tool-side roller 202 during the time. Therefore, the treatment tool-side roller 202 of the interlocking mechanism 134 does not rotate, and the position of the distal end of the endoscope insertion part 12 does not change as illustrated in the (B) portion of FIG. 17. Moreover, at the timing at which the treatment tool insertion part 52 is moved forward to a position with a movement amount of L/2, the proximal end of the reduced diameter part 58 of the treatment tool insertion part 52, that is, the distal end of a non-reduced diameter part behind the reduced diameter part 58 contacts with the outer peripheral surface 202s of the treatment tool-side roller 202.

Subsequently, when the treatment part 54 is moved forward to move the treatment part 54 forward, that is, when the treatment part 54 is further moved forward from the position with a movement amount of L/2, the outer peripheral surface 52s of the non-reduced diameter part of the treatment tool insertion part 52 contacts with the outer peripheral surface 202s of the treatment tool-side roller 202 and the treatment tool-side roller 202 rotates in the clockwise direction in the figure.

By this means, the endoscope-side roller 200 rotates in the anti-clockwise direction in the figure, and the endoscope insertion part 12 moves forward in interlock with the forward movement of the treatment tool insertion part 52 as illustrated in (C) portion of FIG. 17. At this time, when a movement amount to move the treatment tool insertion part 52 forward is assumed to be x, the distal end of the endoscope insertion part 12 also moves forward only by movement amount x.

Operation similar to this is performed even in a case where the treatment tool insertion part 52 is moved backward. (A) portion of FIG. 18 illustrates a state where the central point of the reduced diameter part 58 of the treatment tool insertion part 52 is disposed in the same position in the back-and-forth direction with respect to the central axis of the treatment tool-side roller 202, which is similar to (A) portion of FIG. 17. When the treatment tool insertion part 52 in this state is moved backward to a position with a movement amount of L/2 and the treatment part 54 is moved backward only by movement amount L/2, the outer peripheral surface 52s of the treatment tool insertion part 52 does not contact with the outer peripheral surface 202s of the treatment tool-side roller 202 during the time. Therefore, the treatment tool-side roller 202 of the interlocking mechanism 134 does not rotate, and the position of the distal end of the endoscope insertion part 12 does not change as illustrated in the (B) portion of FIG. 18. Moreover, at the timing at which the treatment tool insertion part 52 is moved backward to the position with a movement amount of L/2, the distal end of the reduced diameter part 58 of the treatment tool insertion part 52, that is, the proximal end of the non-reduced diameter part before the reduced diameter part 58 contacts with the outer peripheral surface 202s of the treatment tool-side roller 202.

Subsequently, when the treatment tool insertion part 52 is moved backward to move the treatment part 54 backward, that is, when the treatment part 54 is further moved backward from the position with a movement amount of L/2, the outer peripheral surface 52s of the non-reduced diameter part of the treatment tool insertion part 52 contacts with the outer peripheral surface 202s of the treatment tool-side roller 202 and the treatment tool-side roller 202 rotates in the anti-clockwise direction in the figure.

By this means, the endoscope-side roller 200 rotates in the clockwise direction in the figure, and the endoscope insertion part 12 moves backward in interlock with the backward movement of the treatment tool insertion part 52 as illustrated in (C) portion of FIG. 18. At this time, when a movement amount to move the treatment tool insertion part 52 backward is assumed to be x, the distal end of the endoscope insertion part 12 moves backward only by movement amount x.

By providing the allowance of the interlocking mechanism 134 with respect to the back-and-forth movement of the treatment tool insertion part 52 as mentioned above, for example, when a surgeon operates the treatment part 54 of the treatment tool 50 and performs treatment, even in a case where a small amount of back-and-forth movement (variation of a back and forth position) is intentionally or non-intentionally caused in the treatment tool insertion part 52, the visual field range of the endoscope 10 does not vary and a taken image which enables to easily perform operation is obtained.

Here, the size of such the allowance can be changed according to length L of the reduced diameter part 58 of the treatment tool insertion part 52.

Moreover, the allowance is limited to a state where the treatment part 54 of the treatment tool insertion part 52 is drawn out by constant delivery amount M from the outer tube 100 (treatment tool exit port 122b). However, it only has to adjust the insertion amount of the outer tube 100 into a body cavity (body cavity wall) so that such delivery amount M is set in the insertion position of the treatment part 54 in the body cavity in which the surgeon desires to have the allowance. Alternatively, as for the treatment tool 50 of the same kind, multiple treatment tools having different distances (the position of the reduced diameter part 58) from the treatment part 54 to the reduced diameter part 58 in the treatment tool insertion part 52 are prepared, and a surgeon can select and use the one having an optimal delivery amount M of the treatment part 54 from such the treatment tools having the allowance (it is similarly possible to select length L of the reduced diameter part 58 in a case where the size of allowance is varied).

Moreover, the surgeon can arbitrarily adjust the delivery amount of the distal end of the endoscope 10 when the treatment tool 50 has an allowance as mentioned above. For example, in a case where the endoscope insertion part 12 is inserted in the outer tube 100 simultaneously with the treatment tool insertion part 52 or the treatment tool insertion part 52 is inserted in the outer tube 100 first, when the treatment tool insertion part 52 enters a state where it has allowance, that is, when the endoscope insertion part 12 enters a state where it does not move in interlock with the treatment tool insertion part 52, it is possible to move only the endoscope insertion part 12 back and forth in the endoscope insertion hole 120 and adjust the distal end of the endoscope insertion part 12 to a desired delivery amount. On the other hand, in a case where the endoscope insertion part 12 is inserted in the outer tube 100 first, when the treatment tool insertion part 52 is inserted in the treatment tool insertion hole 122 after the endoscope insertion part 12 is adjusted to a desired delivery amount, it has to prevent the endoscope insertion part 12 from moving back and forth in interlock with the treatment tool insertion part 52 by only holding the proximal end side of the endoscope insertion part 12 by hand or the like until the treatment tool insertion part 52 enters a state where it has an allowance.

Modification Example of Interlocking Mechanism of First Embodiment

In the interlocking mechanism 134 of the first embodiment mentioned above, a range where the treatment tool insertion part 52 does not contact with the outer peripheral surface 202s of the treatment tool-side roller 202 is provided by forming the reduced diameter part 58 in the treatment tool insertion part 52. By this means, there is provided a non-interlocking part that releases interlocking between the treatment tool 50 (treatment tool insertion part 52) and the treatment tool-side roller 202. However, the configuration of the non-interlocking part is not limited to this. For example, the outer peripheral surface of a range corresponding to the reduced diameter part 58 may be formed with a material that is slipperier than other range (a range corresponding to the non-reduced diameter part) front and rear of it, instead of forming the reduced diameter part 58 as a non-interlocking part in the treatment tool insertion part 52. Thereby, the treatment tool-side roller 202 may be prevented from rotating even if the treatment tool insertion part 52 is moved back and forth in the range corresponding to the reduced diameter part 58.

Moreover, an allowance may be provided by inserting the treatment tool insertion part 52 so as to be freely movable back and forth in a hollow part of a cylindrical pipe member and inserting the treatment tool insertion part 52 in the treatment tool insertion hole 122 together with the pipe member, instead of providing a non-interlocking part that releases interlocking between the treatment tool 50 and the treatment tool-side roller 202 like the reduced diameter part 58 of the treatment tool insertion part 52.

Figure 20:
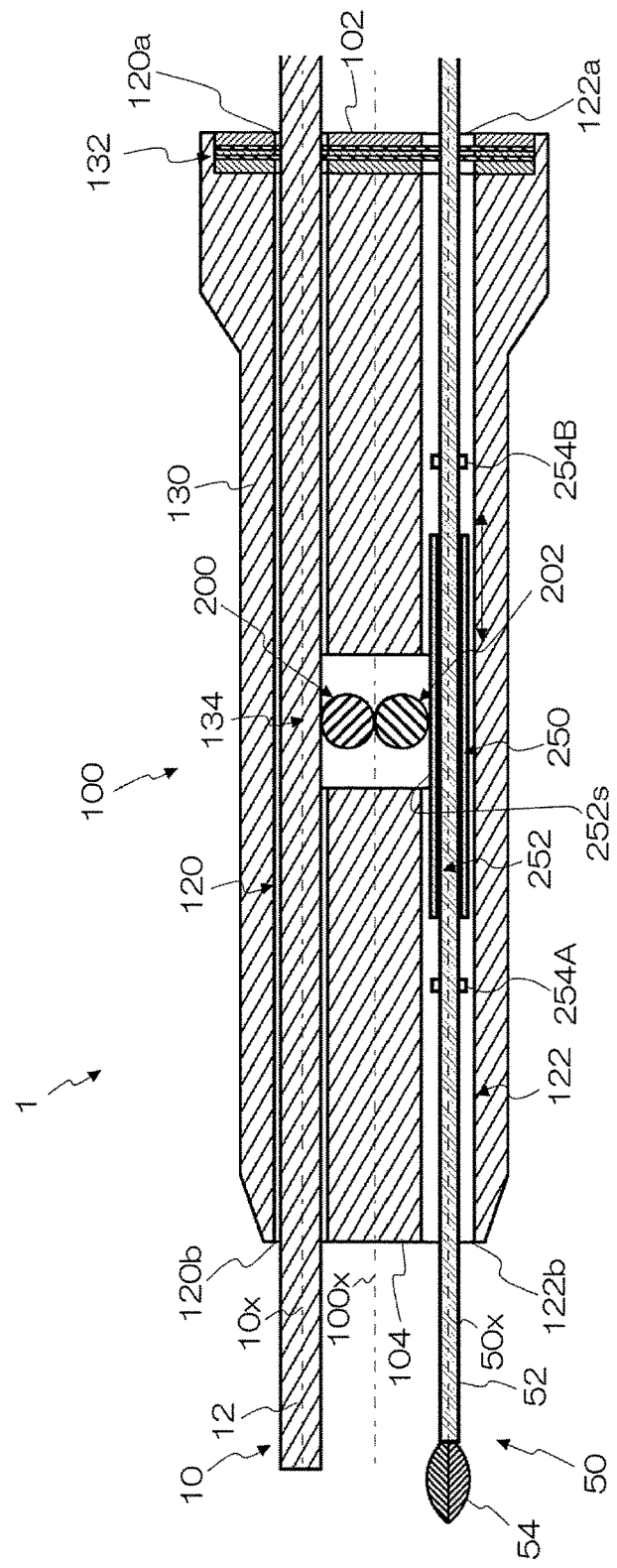
FIG. 20 is a side cross-sectional view of an outer tube, which illustrates a modification example of an interlocking mechanism of the first embodiment.

FIG. 20 is a side cross-sectional view of the outer tube 100, which illustrates a mode in a case where an allowance is provided by such the pipe member as a modification example of the interlocking mechanism 134 of the first embodiment. Here, in the figure, the same reference numerals are assigned to components having function identical or similar to the outer tube 100 including the interlocking mechanism 134 of the first embodiment illustrated in FIGS. 8 and 16, and so on, and the explanation thereof is omitted.

As illustrated in FIG. 20, in the treatment tool insertion hole 122, the treatment tool insertion part 52 is inserted and disposed and a cylindrical pipe member 250 is disposed.

The pipe member 250 is formed into a long cylindrical shape, and the outer diameter thereof substantially matches an inner diameter of the treatment tool insertion hole 122. Therefore, an outer peripheral surface 250s of the pipe member 250 contacts with the outer peripheral surface 202s of the treatment tool-side roller 202, and, when the pipe member 250 moves in the back-and-forth direction, the treatment tool-side roller 202 rotates in interlock with this. Here, in this figure, the outer diameter of the treatment tool insertion part 52 decreases by an extent that the pipe member 250 is provided as compared with FIG. 16. However, the outer diameter of the treatment tool insertion part 52 does not have to be necessarily decreased, and the inner diameter of the treatment tool insertion hole 122 may be increased.

Meanwhile, in the pipe member 250, a through hole 252 is formed so as to penetrate along the central axis of the pipe member 250, and the treatment tool insertion part 52 is inserted in the through hole 252.

The inner diameter of the through hole 252 is slightly larger than the outer diameter of the treatment tool insertion part 52, and the treatment tool insertion part 52 is inserted so as to be able to be movable back and forth relative to the pipe member 250.

Moreover, the reduced diameter part 58 as shown in FIG. 5 is not provided in the treatment tool insertion part 52, and a distal-side engagement part 254A and a proximal-side engagement part 254B which engage with the pipe member 250 are formed before and after a region to which the pipe member 250 is externally fitted.

For example, the distal-side engagement part 254A and the proximal-side engagement part 254B project in a radial direction from the outer peripheral surface 52s of the treatment tool insertion part 52, and they are formed over the whole circumference along the circumferential direction or in a partial range in the circumferential direction.

Further, these distal-side engagement part 254A and proximal-side engagement part 254B are formed in positions in which the intervals in the back-and-forth direction therebetween are wider than the length in the back-and-forth direction of the pipe member 250. By this means, the pipe member 250 can move in the back-and-forth direction between the engagement parts 254A and 254B.

Therefore, the pipe member 250 is externally fitted so as to have an allowance with respect to the treatment tool insertion part 52.

Here, continuous slitting in the back-and-forth direction from the distal end to the proximal end is formed in the pipe member 250, and the pipe member 250 may be externally fitted to the treatment tool insertion part 52 by inserting the space between the distal-side engagement part 254A and the proximal-side engagement part 254B of the treatment tool insertion part 52 in the through hole 252 of the pipe member 250 through the slitting, or it may be externally fitted by other methods.

According to such the pipe member 250, in a case where the treatment tool insertion part 52 is moved forward, the pipe member 250 does not move back and forth until the proximal-side engagement part 254B of the treatment tool insertion part 52 abuts on the proximal end of the pipe member 250, and the treatment tool-side roller 202 does not rotate. That is, there is an allowance in which the endoscope insertion part 12 inserted in the endoscope insertion hole 120 does not move in interlock with the back-and-forth movement of the treatment tool insertion part 52.

On the other hand, when the treatment tool insertion part 52 is further moved forward after the proximal-side engagement part 254B of the treatment tool insertion part 52 abuts on the proximal end of the pipe member 250, the pipe member 250 moves forward together with the treatment tool insertion part 52 and the treatment tool-side roller 202 rotates in interlock with this. Therefore, the endoscope insertion part 12 also moves forward in interlock with the treatment tool insertion part 52.

Even in a case where the treatment tool insertion part 52 is moved backward, similarly, the pipe member 250 does not move back and forth until the distal-side engagement part 254A of the treatment tool insertion part 52 abuts on the distal end of the pipe member 250, and the treatment tool-side roller 202 does not rotate. That is, there is an allowance in which the endoscope insertion part 12 does not move in interlock with the back-and-forth movement of the treatment tool insertion part 52.

On the other hand, when the treatment tool insertion part 52 is further moved backward after the distal-side engagement part 254A of the treatment tool insertion part 52 abuts on the distal end of the pipe member 250, the pipe member 250 moves backward together with the treatment tool insertion part 52 and the treatment tool-side roller 202 rotates in interlock with this. Therefore, the endoscope insertion part 12 also moves backward in interlock with the treatment tool insertion part 52.

By adopting a configuration in which the back-and-forth movement of the treatment tool insertion part 52 (treatment tool 50) is transmitted to the endoscope insertion part 12

(endoscope 10) through an allowance generation member such as the above-mentioned pipe member 250, it is possible to provide an allowance of the interlocking mechanism 134 in which the endoscope insertion part 12 does not move in interlock with the back-and-forth movement of the treatment tool insertion part 52.

Here, the distal-side engagement part 254A and the proximal-side engagement part 254B may be configured as members detachable from the treatment tool insertion part 52 so that their mounting positions can be freely varied to adjust the size of the allowance or the like.

Moreover, as for a configuration to externally fit the pipe member 250 to the treatment tool insertion part 52 with an allowance, an arbitrary configuration can be adopted.

For example, a region which is a partial region in the back-and-forth direction along the central axis of the treatment tool insertion part 52 and which is longer than the pipe member 250 in the back-and-forth direction may have a diameter smaller than the front and rear of that region, and the pipe member 250 may be externally fitted into the region having a smaller diameter so as to be movable back and forth. In this case, by forming the outer diameter of the pipe member 250 so as to substantially match an outer diameter in a region other than that region having a smaller diameter, it is possible to omit expansion of the inner diameter of the treatment tool insertion hole 122 so as to make it match with the outer diameter of the pipe member 250.

Figure 21:
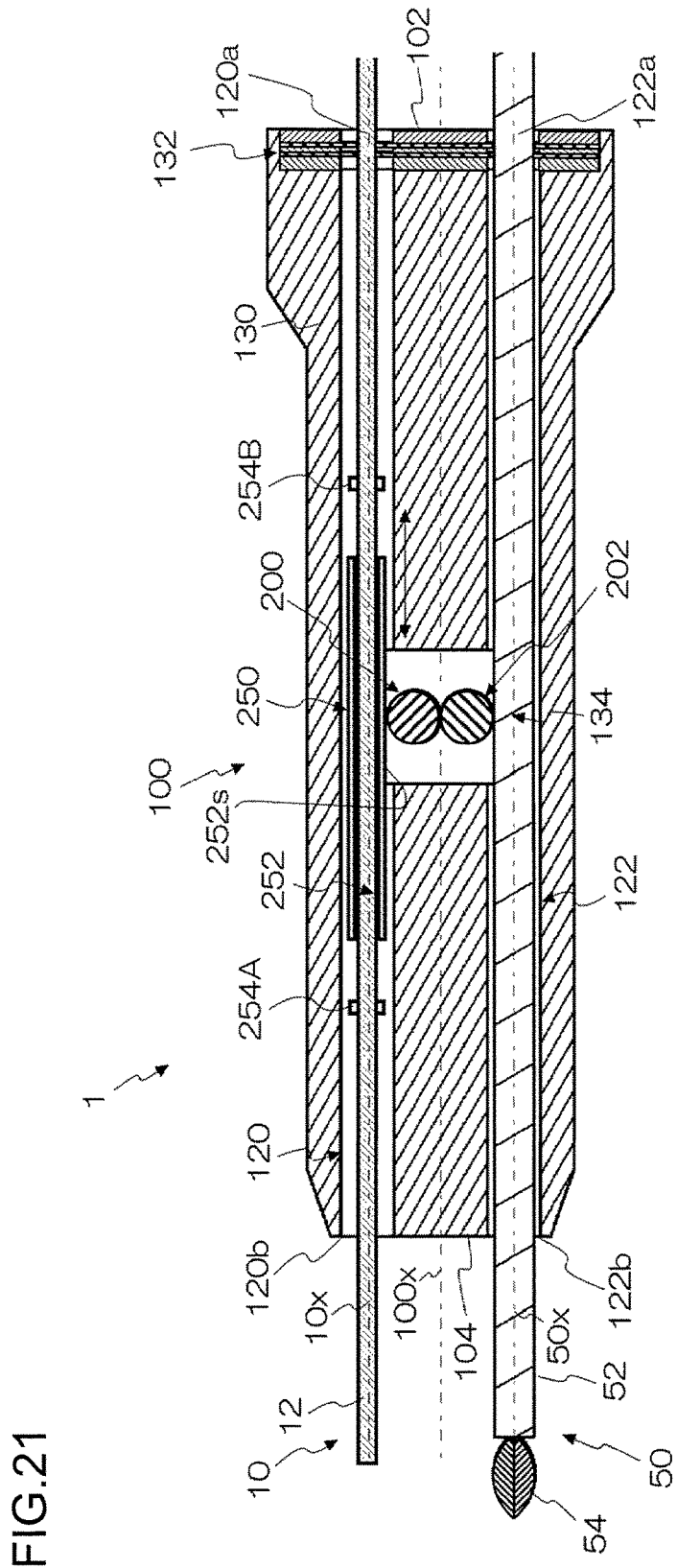
FIG. 21 is a side cross-sectional view of an outer tube, which illustrates a modification example of an interlocking mechanism of the first embodiment.

Moreover, the allowance generation member may be disposed in the endoscope insertion hole 120 instead of being disposed in the treatment tool insertion hole 122, and a configuration in the case is illustrated in FIG. 21. In the figure, the same reference numerals are assigned to components having function identical or similar to FIG. 20, the pipe member 250 is externally fitted to the endoscope insertion part 12 inserted in the endoscope insertion hole 120 so as to be movable back and forth, and the distal-side engagement part 254A and the proximal-side engagement part 254B which engage with the pipe member 250 are provided in the endoscope insertion part 12.

According to this, in a case where the treatment tool insertion part 52 is moved forward, the treatment tool-side roller 202 rotates and the endoscope-side roller 200 rotates in interlock with this, and the pipe member 250 moves forward. Further, the endoscope insertion part 12 does not move back and forth until the distal end of the pipe member 250 abuts on the distal-side engagement part 254A of the endoscope insertion part 12. That is, there is an allowance in which the endoscope insertion part 12 does not move in interlock with the back-and-forth movement of the treatment tool insertion part 52.

On the other hand, when the treatment tool insertion part 52 is further moved forward after the distal end of the pipe member 250 abuts on the distal-side engagement part 254A of the endoscope insertion part 12, the endoscope insertion part 12 moves forward together with the pipe member 250. Therefore, the endoscope insertion part 12 also moves forward in interlock with the treatment tool insertion part 52.

Even in a case where the treatment tool insertion part 52 is moved backward, similarly, the pipe member 250 moves backward in interlock with this. Further, the endoscope insertion part 12 does not move back and forth until the proximal end of the pipe member 250 abuts on the proximal-side engagement part 254B of the endoscope insertion part 12. That is, there is an allowance in which the endoscope insertion part 12 does not move in interlock with the back-and-forth movement of the treatment tool insertion part 52.

On the other hand, when the treatment tool insertion part 52 is further moved backward after the proximal end of the pipe member 250 abuts on the proximal-side engagement part 254B of the endoscope insertion part 12, the endoscope insertion part 12 moves backward together with the pipe member 250. Therefore, the endoscope insertion part 12 also moves backward in interlock with the treatment tool insertion part 52.

An allowance of the interlocking mechanism 134 may be provided to a modification example of the interlocking mechanism 134 of the first embodiment and the interlocking mechanism 134 of the second embodiment, which are described next, by using an allowance generation member like the pipe member 250, instead of the reduced diameter part 58 of the above-mentioned treatment tool insertion part 52.

Moreover, the interlocking mechanism 134 of the first embodiment shows a mode in which the endoscope-side roller 200 and the treatment tool-side roller 202 are arranged side by side in the right-and-left direction in the same positions in a direction (back-and-forth direction) along the longitudinal axis 100x of the outer tube 100. However, the endoscope-side roller 200 and the treatment tool-side roller 202 may not be necessarily disposed in the same positions in the back-and-forth direction of the outer tube 100.

Figure 22:
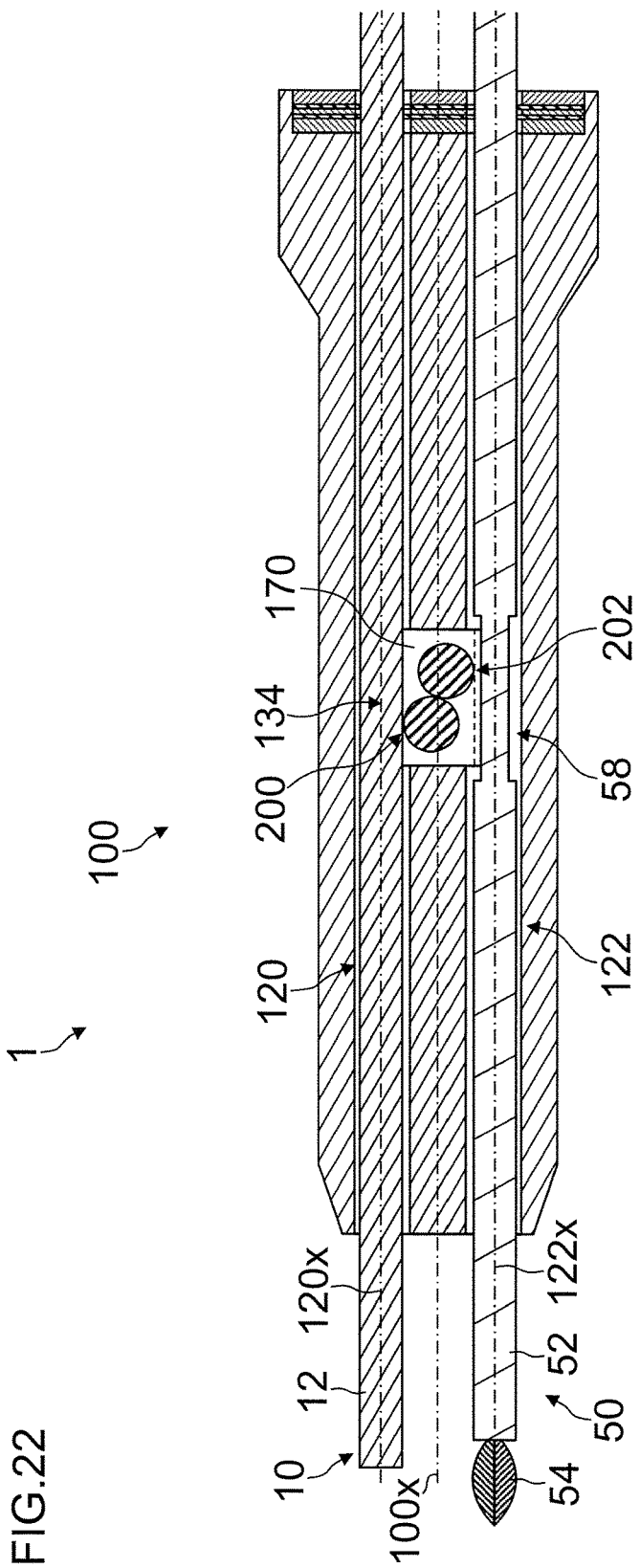
FIG. 22 is a side cross-sectional view of an outer tube, which illustrates a modification example of an interlocking mechanism of the first embodiment.

FIG. 22 is a side cross-sectional view of the outer tube 100, which illustrates a mode in that case as a modification example of the interlocking mechanism 134 of the first embodiment. In the figure, the same reference numerals are assigned to components having function identical or similar to the components of the outer tube 100 including the interlocking mechanism 134 of the first embodiment illustrated in FIGS. 8, 16, and so on, and the explanation thereof is omitted.

As illustrated in FIG. 22, in the cavity part 170 of the outer tube 100, the endoscope-side roller 200 is disposed forward of the treatment tool-side roller 202, and the outer peripheral surface 200s of the endoscope-side roller 200. The outer peripheral surface 202s of the treatment tool-side roller 202 contact with each other on a segment that connects the center of the endoscope-side roller 200 and the center of the treatment tool-side roller 202. By this means, the endoscope-side roller 200 and the treatment tool-side roller 202 rotate in interlock with each other.

Moreover, the endoscope-side roller 200 is disposed such that a partial range in the peripheral direction of the outer peripheral surface 200s projects into the endoscope insertion hole 120 and contacts with the outer peripheral surface 12s of the endoscope insertion part 12 inserted in the endoscope insertion hole 120.

The treatment tool-side roller 202 is disposed such that a partial range in the peripheral direction of the outer peripheral surface 202s projects into the treatment tool insertion hole 122 and contacts with the outer peripheral surface 52s of the non-reduced diameter part of the treatment tool insertion part 52 inserted in the treatment tool insertion hole 122.

By this means, in the same way as the first embodiment, the endoscope insertion part 12 moves back and forth in interlock with the back-and-forth movement of the treatment tool insertion part 52 via the interlocking mechanism 134, and there is provided an allowance of the interlocking mechanism 134 in which they are not interlocked in a state where the reduced diameter part 58 of the treatment tool insertion part 52 faces the treatment tool-side roller 202.

According to this modification example, it is possible to achieve diameter reduction of the outer tube 100 (insertion part 110). That is, when the outer tube 100 including the interlocking mechanism 134 of the first embodiment like FIGS. 8, 16, and so on, and the outer tube 100 including the interlocking mechanism 134 of a modification example like FIG. 22 are compared, it is assumed that the endoscope-side roller 200 and the treatment tool-side roller 202 are the same (the diameters of the outer peripheral surfaces are matched), since the outer tube 100 including the interlocking mechanism 134 of the modification example in FIG. 22 can make the endoscope insertion axis 120x and the treatment tool insertion axis 122x mutually close to each other, it is accordingly possible to reduce the outer diameter of the outer tube body 130 (the insertion part 110 of the outer tube 100).

Here, the endoscope-side roller 200 may be disposed on the proximal side of the treatment tool-side roller 202.

In the above, the interlocking mechanism 134 of the above-mentioned first embodiment (including the modification example) is a mode in which it has a rotation axis orthogonal to both the endoscope insertion axis 120x and the treatment tool insertion axis 122x (a rotation axis in a direction orthogonal to a plane parallel to both the endoscope insertion axis 120x and the treatment tool insertion axis 122x) and two rollers that synchronously rotate in the anti-clockwise direction are contacted (or coupled through an allowance generation member) with the endoscope insertion part 12 and the treatment tool insertion part 52 respectively. However, the configuration of the interlocking mechanism 134 is not limited to this.

For example, the rotation axes of two rollers may not be necessarily orthogonal to both the endoscope insertion axis 120x and the treatment tool insertion axis 122x, and they may three-dimensionally intersect. Moreover, instead of interlocking two rollers by making their outer peripheral surfaces directly contact with each other, it is possible to interlock them through a power transmission mechanism including a gear, a belt, other rollers, and so on. In addition, in the case of a mode in which two rollers are interlocked through the power transmission mechanism, two rollers may be disposed in any positions and the rotation axis direction is not limited to a specific direction.

Here, even in the interlocking mechanism 134 of the second and third embodiments described below, a transformable and additional configuration that is applicable to the interlocking mechanism 134 of the above-mentioned first embodiment can be arbitrarily adopted.

Interlocking Mechanism of Second Embodiment

Next, the interlocking mechanism 134 of the second embodiment is described.

The interlocking mechanism 134 of the second embodiment is a mode in which one roller (a roller that rotates around one rotation axis) having a rotation axis orthogonal to both the endoscope insertion axis 120x and the treatment tool insertion axis 122x is contacted (or coupled through an allowance generation member) with both the endoscope insertion part 12 and the treatment tool insertion part 52. That is, it is a mode in which the endoscope 10 is moved in interlock with the back-and-forth movement of the treatment tool 50 by a roller having a rotation axis parallel to a plane that contacts with the outer peripheral surface 12s of the endoscope insertion part 12 and the outer peripheral surface 52s of the treatment tool insertion part 52 from the same direction.

Figure 23:
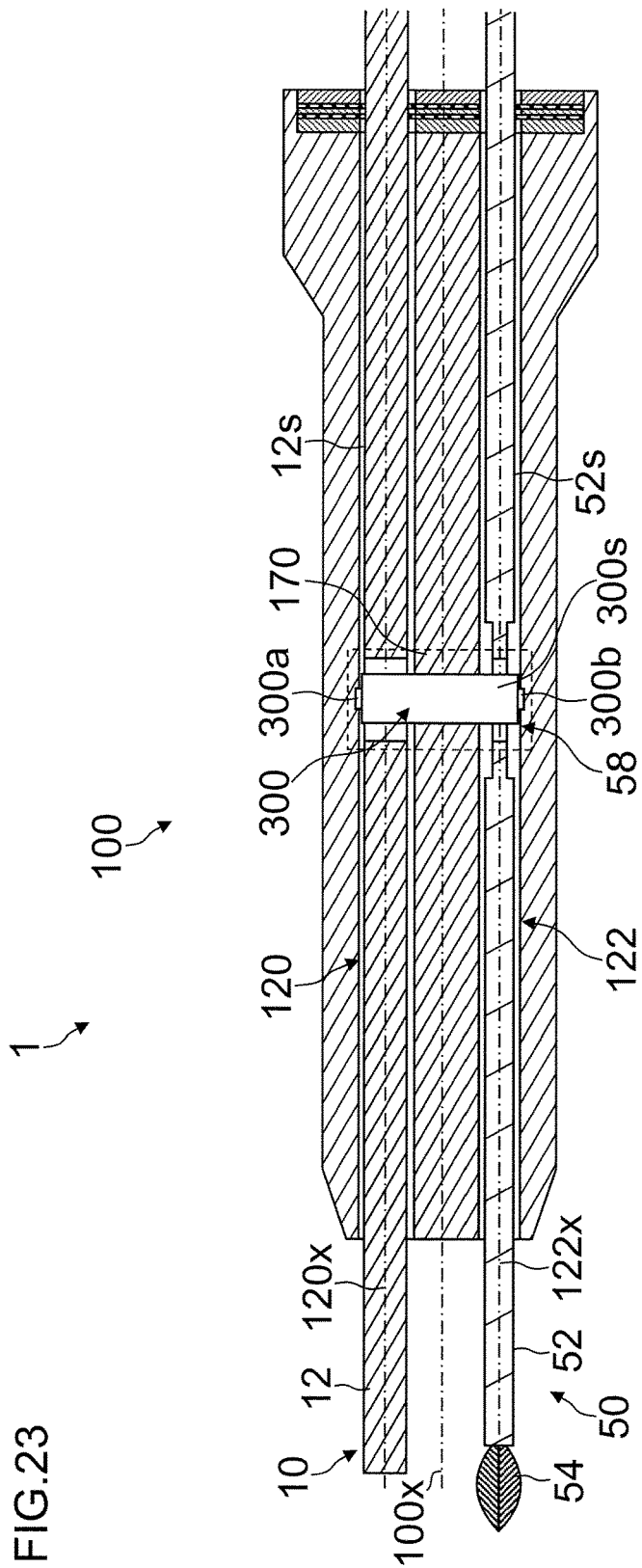
FIG. 23 is a schematic diagram illustrating an outer tube including an interlocking mechanism of the second embodiment from the side surface side.
Figure 24:
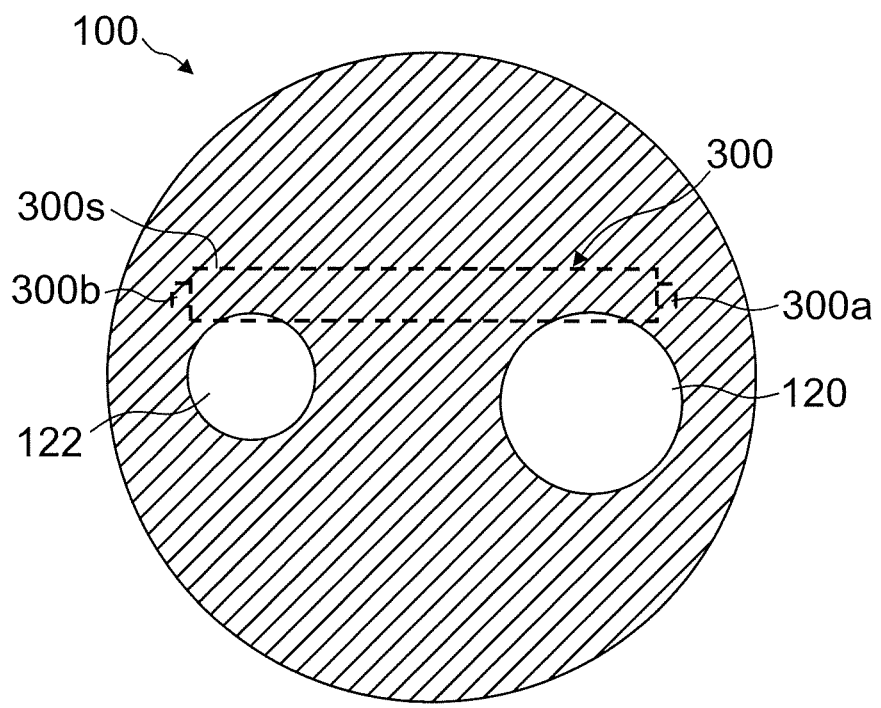
FIG. 24 is a schematic diagram illustrating the outer tube including the interlocking mechanism of the second embodiment from the rear surface side.

FIGS. 23 and 24 are schematic diagrams illustrating the outer tube 100 including the interlocking mechanism 134 of the second embodiment from the side surface side and the rear surface side respectively. Here, since components except for the configuration of the interlocking mechanism 134 are formed in the same way as the outer tube 100 including the interlocking mechanism 134 of the first embodiment illustrated in FIG. 8 or the like, components having function identical or similar to the outer tube 100 illustrated in FIG. 8 or the like are shown using the same reference numerals, and the explanation thereof is omitted. Only characteristic components of the interlocking mechanism 134 of the second embodiment are described. Moreover, FIGS. 23 and 24 illustrate that the diameter of the treatment tool insertion hole 122 is assumed to be smaller than the endoscope insertion hole 120.

As illustrated in these figures, the interlocking mechanism 134 of the second embodiment includes one roller 300 disposed in the cavity part 170 formed inside the outer tube 100 (outer tube body 130).

The roller 300 is a columnar member having a cylindrical surface (outer peripheral surface 300s), and whose central axis (rotation axis) is disposed in a direction which is orthogonal to both the endoscope insertion axis 120x and the treatment tool insertion axis 122x, and is parallel to a plane that contacts with the inner peripheral surface 120s of the endoscope insertion hole 120 and the inner peripheral surface 122s of the treatment tool insertion hole 122.

Axis pins 300a and 300b that extend along the central axis are provided in each of the end surfaces on both sides of the roller 300. Those axis pins 300a and 300b are internally fitted to a pair of unillustrated engagement holes provided on the wall surface of the cavity part 170, and the roller 300 is supported so as to be rotatable around the central axis thereof. Here, the roller 300 may be supported so as to be rotatable around the axis member inserted in the position of the central axis of the roller 300.

Moreover, the roller 300 is disposed such that a partial range on one end part side of the central axis direction of the roller 300 projects into the endoscope insertion hole 120 and a partial range on the other end part side projects into the treatment tool insertion hole 122. By this means, the outer peripheral surface 300s of the roller 300 contacts with the outer peripheral surface 12s of the endoscope insertion part 12 inserted in the endoscope insertion hole 120 and the outer peripheral surface 52s (excluding the range of the reduced diameter part 58) of the treatment tool insertion part 52 inserted in the treatment tool insertion hole 122.

Therefore, the roller 300 rotates by the back-and-forth movement of the treatment tool insertion part 52, and the endoscope insertion part 12 moves back and forth in interlock with the rotation of the roller 300. Moreover, since the outer peripheral surface 52s of the treatment tool insertion part 52 does not contact with the outer peripheral surface 300s of the roller 300 when the reduced diameter part 58 of the treatment tool insertion part 52 faces the outer peripheral surface 300s of the roller 300, an allowance of the interlocking mechanism 134 is provided with respect to the back-and-forth movement of the treatment tool insertion part 52.

Here, the allowance of the interlocking mechanism 134 may be provided by the allowance generation member (pipe member 250) as illustrated in FIGS. 20 and 21.

Interlocking Mechanism of Third Embodiment

Next, the interlocking mechanism 134 of the third embodiment is described.

In the interlocking mechanism 134 of the first and second embodiments, the allowance of the interlocking mechanism 134 with respect to the back-and-forth movement of the treatment tool insertion part 52 is provided by processing (machining) the treatment tool insertion part 52 like the reduced diameter part 58 or providing an allowance generation member disposed in the treatment tool insertion hole 122 or the endoscope insertion hole 120 like the pipe member 250 in FIGS. 20 and 21. On the other hand, the interlocking mechanism 134 of the third embodiment is a mode in which the allowance of the interlocking mechanism 134 is provided without processing the treatment tool insertion part 52 or using the allowance generation member disposed in the treatment tool insertion hole 122 or the endoscope insertion hole 120.

Figure 25:
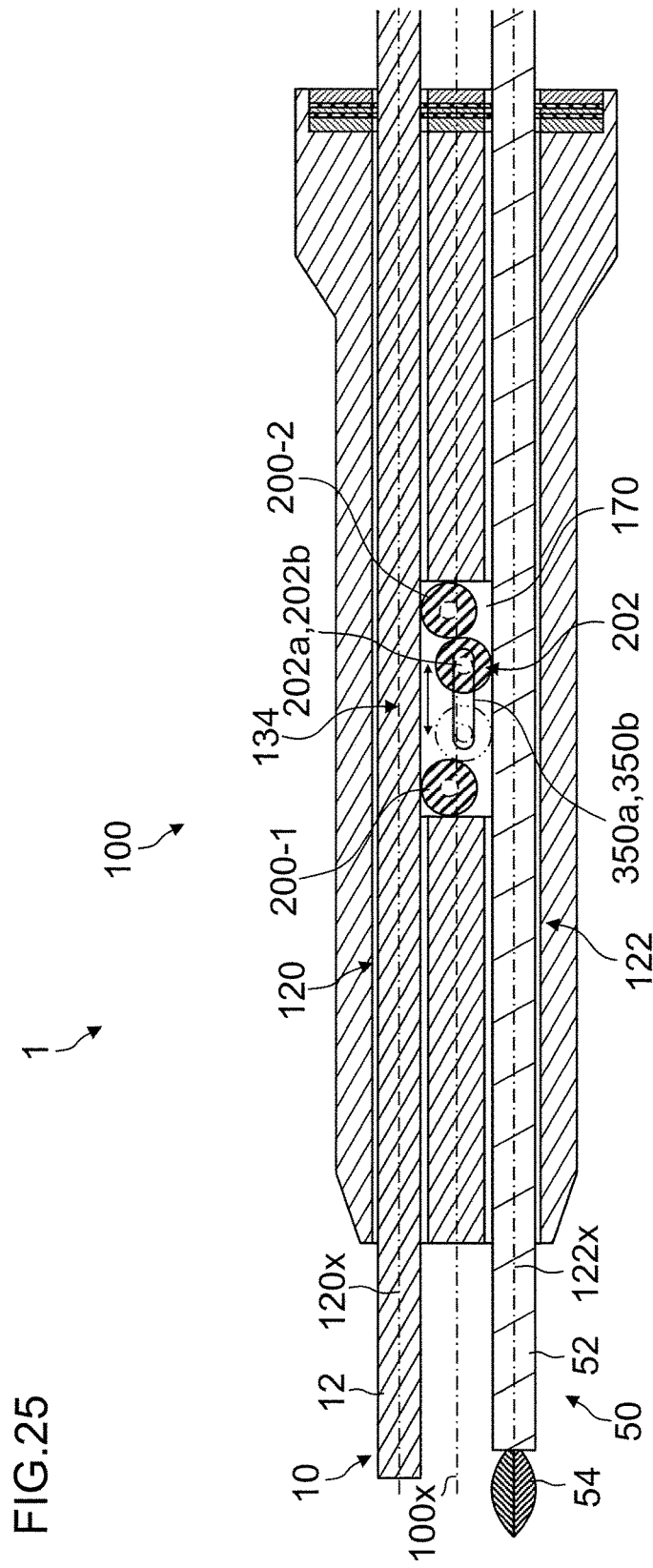
FIG. 25 is a schematic diagram illustrating an outer tube including an interlocking mechanism of the third embodiment from the side surface side.

FIG. 25 is a schematic diagram illustrating the outer tube 100 including the interlocking mechanism 134 of the third embodiment from the side surface side. Here, since components except for the configuration of the interlocking mechanism 134 are formed in the same way as the outer tube 100 including the interlocking mechanism 134 of the first embodiment illustrated in FIG. 8 or the like, components having function identical or similar to the outer tube 100 illustrated in FIG. 8 or the like are shown using the same reference numerals, the explanation thereof is omitted. Only characteristic components of the interlocking mechanism 134 of the third embodiment are described.

As illustrated in the figure, the interlocking mechanism 134 of the third embodiment includes two endoscope-side rollers 200-1 and 200-2 and a treatment tool-side roller 202 which are disposed in the cavity part 170 formed in the same position as the first embodiment in the outer tube body 130. The endoscope-side roller 200-1 and the endoscope-side roller 200-2 are disposed in two positions at a predetermined interval from each other in the back-and-forth direction along the longitudinal axis 100x.

The endoscope-side rollers 200-1 and 200-2 and the treatment tool-side roller 202 are columnar members having cylindrical surfaces (outer peripheral surfaces 200s-1, 200s-2 and 202s), and, similar to the first embodiment, their central axes (rotation axes) are disposed so as to be orthogonal to a horizontal reference surface (a plane which includes the endoscope insertion axis 120x and is parallel to the treatment tool insertion axis 122x). That is, respective central axes of the endoscope-side rollers 200-1 and 200-2 and the treatment tool-side roller 202 are disposed in a direction orthogonal to both the endoscope insertion axis 120x and the treatment tool insertion axis 122x.

In each of the end surfaces on both upper and lower sides of the endoscope-side rollers 200-1 and 200-2, axis pins are provided along their central axes in the same way as the first embodiment and the endoscope-side roller 200. The axis pins are internally fitted to two pairs of engagement holes formed in different positions in the back-and-forth direction of the wall surface of the cavity part 170, and are rotatably supported.

Moreover, the outer peripheral surfaces of the endoscope-side rollers 200-1 and 200-2 are disposed to project into the endoscope insertion hole 120. The endoscope insertion part 12 in the endoscope insertion hole 120 moves back and forth in interlock with the rotation of the endoscope-side rollers 200-1 and 200-2, and the endoscope-side rollers 200-1 and 200-2 rotate in interlock with the back-and-forth movement of the endoscope insertion part 12 in the endoscope insertion hole 120.

On the other hand, also in the end surfaces on both the upper and lower sides of the treatment tool-side roller 202, the axis pins 202a and 202b are provided along the central axis of the treatment tool-side roller 202 in the completely same way as the first embodiment. However, those axis pins 202a and 202b are internally fitted to a pair of engagement grooves 350a and 350b that are provided so as to extend in the back-and-forth direction along the longitudinal axis 100x (treatment tool insertion axis 122x) in the upper and lower wall surfaces of the cavity part 170. By this means, the treatment tool-side roller 202 is supported so as to be rotatable around the central axis, and is supported so as to be able to move back and forth in a direction along the longitudinal axis 100x.

Moreover, the outer peripheral surface of the treatment tool-side roller 202 is disposed to project into the treatment tool insertion hole 122, and rotates and moves back and forth in interlock with the back-and-forth movement of the treatment tool insertion part 52 in the treatment tool insertion hole 122.

In addition, in a predetermined position (distal side restriction position) when the treatment tool-side roller 202 is guided by the engagement grooves 350a and 350b to move toward the distal side, its outer peripheral surface abuts on the outer peripheral surface of the endoscope-side roller 200-1 and movement toward the distal side is restricted. In a predetermined position (proximal side restriction position) when the treatment tool-side roller 202 moves toward the proximal side, the outer peripheral surface abuts on the outer peripheral surface of the endoscope-side roller 200-2 and movement toward the proximal side is restricted. In a position that is neither the distal side restriction position nor the proximal side restriction position, the outer peripheral surface of the treatment tool-side roller 202 is separated from both the outer peripheral surfaces of the endoscope-side rollers 200-1 and 200-2.

According to the interlocking mechanism 134 of the third embodiment configured as above, it is possible to provide an allowance of the interlocking mechanism 134 with respect to the back-and-forth movement of the treatment tool insertion part 52 in the same way as the interlocking mechanism 134 of the first embodiment. For example, a state is assumed in which the endoscope insertion part 12 is inserted in the endoscope insertion hole 120, the treatment tool insertion part 52 is inserted in the treatment tool insertion hole 122 and the treatment tool-side roller 202 is disposed in the intermediate point between the distal side restriction position and the proximal side restriction position.

When the treatment tool insertion part 52 in the state is moved forward to the distal side restriction position and the treatment part 54 is moved forward, the treatment tool-side roller 202 moves forward together with the treatment tool insertion part 52 during that time while rotating in the clockwise direction, but the outer peripheral surface of the treatment tool-side roller 202 does not contact with any of the outer peripheral surfaces of the endoscope-side rollers 200-1 and 200-2. Therefore, the position of the distal end of the endoscope insertion part 12 does not vary. At the timing the treatment tool insertion part 52 is moved forward to the distal side restriction position, the outer peripheral surface of the treatment tool-side roller 202 contacts with the outer peripheral surface of the endoscope-side roller 200-1.

Subsequently, when the treatment tool insertion part 52 is moved forward and the treatment part 54 is moved forward, the treatment tool-side roller 202 rotates in the distal side restriction position, and the endoscope-side roller 200-1 rotates in the anti-clockwise direction in the figure in interlock with this. By this means, the endoscope insertion part 12 moves forward in interlock with the forward movement of the treatment tool insertion part 52.

Even in a case where the treatment tool insertion part 52 is moved backward, operation similar to this is performed.

As mentioned above, in the interlocking mechanism 134 of the third embodiment, the treatment tool-side roller 202 functions as an allowance generation member between the treatment tool-side roller 202 and the endoscope-side rollers 200-1 and 200-2, and there is provided an allowance of the interlocking mechanism 134 with respect to the back-and-forth movement of the treatment tool insertion part 52.

Moreover, when the direction of the back-and-forth movement of the treatment tool insertion part 52 is varied, there is provided an allowance in which the endoscope insertion part 12 does not move in interlock with the back-and-forth movement of the treatment tool insertion part 52.

<Outer Tube for Side-Viewing Type Endoscope>

The interlocking mechanism 134 of the above-mentioned first to third embodiments shows a configuration in a case where the interlocking mechanism 134 is provided in the outer tube 100 in which the endoscope insertion axis 120x of the endoscope insertion hole 120 and the treatment tool insertion axis 122x of the treatment tool insertion hole 122 are provided in parallel to each other. However, the interlocking mechanism 134 in a similar mode can also be provided in an outer tube in which the endoscope insertion axis 120x of the endoscope insertion hole 120 and the treatment tool insertion axis 122x of the treatment tool insertion hole 122 are non-parallel.

For example, the outer tube 100 including the interlocking mechanism 134 of the above-mentioned first to third embodiments is used as an outer tube for the endoscopic surgical device 1 (see FIG. 1) using a forward-viewing type endoscope that mainly performs imaging while setting a direction (forward direction) along the central axis of the endoscope insertion part 12, as a visual direction.

On the other hand, in the case of an outer tube for an endoscopic surgical device using a side-viewing type endoscope that performs imaging while setting a direction (for example, an orthogonal direction) that is not parallel to the central axis of an endoscope insertion part as a visual direction, there is a case where the axis of an endoscope insertion hole and the axis of a treatment tool insertion hole are not parallel. Even in such the outer tube, it is possible to provide an interlocking mechanism similar to the interlocking mechanism 134 in the above-mentioned mode.

In the following, with an outer tube of an endoscopic surgical device using a side-viewing type endoscope as an example, an interlocking mechanism in the outer tube in which the endoscope insertion axis of an endoscope insertion hole and the treatment tool insertion axis of a treatment tool insertion hole are non-parallel (a twisted positional relationship is provided) is described.

Figure 26:
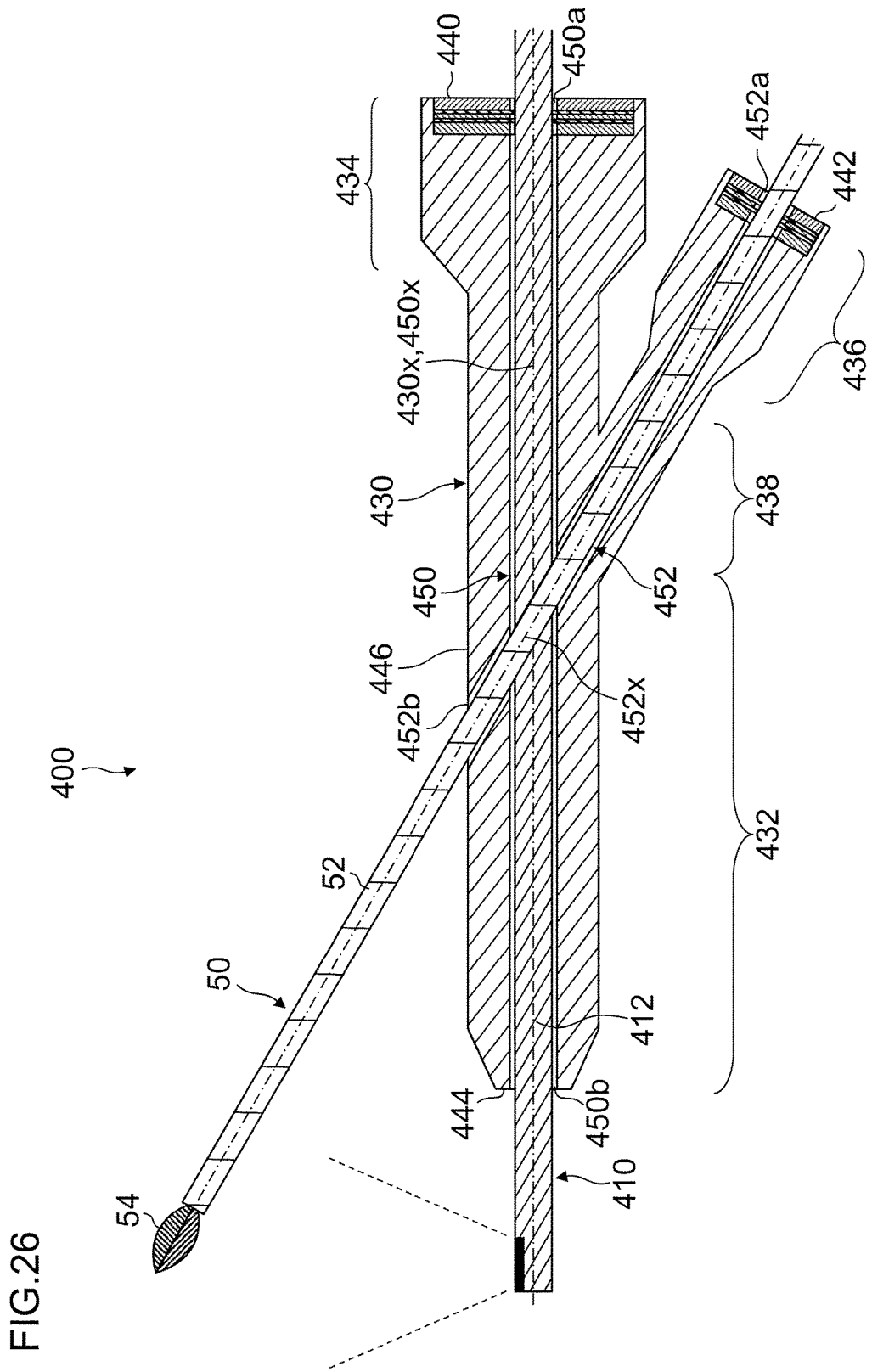
FIG. 26 is a schematic configuration diagram of an endoscopic surgical device using a side view endoscope.

First, it is shown in the schematic diagram in FIG. 26 illustrating an endoscopic surgical device using a side-viewing type endoscope from the side surface side.

An endoscopic surgical device 400 illustrated in the figure includes a side-viewing type endoscope 410 which is to be inserted in patient's body cavity to observe the inside of the body cavity, the treatment tool 50 which is to be inserted in patient's body cavity to perform necessary treatment, and an outer tube 430 which guides the side-viewing type endoscope 410 and the treatment tool 50 into patient's body cavity.

The side-viewing type endoscope 410 (which is simply called an endoscope 410 below) includes an imaging device that takes an image observed from an observation window in the same way as the endoscope 10 in FIG. 1 in the distal end, but it differs from the endoscope 10 in that the observation window is disposed toward the side direction instead of the front direction of an insertion part (endoscope insertion part) 412 and the side direction is observed. Moreover, regarding other points, it has substantially the same configuration as the endoscope 10, and the explanation is omitted for well-known components of the components of the side-viewing type endoscope.

The treatment tool 50 is the same as the one described using FIGS. 1 and 5. Here, the reduced diameter part 58 is omitted in the figure.

Figure 27:
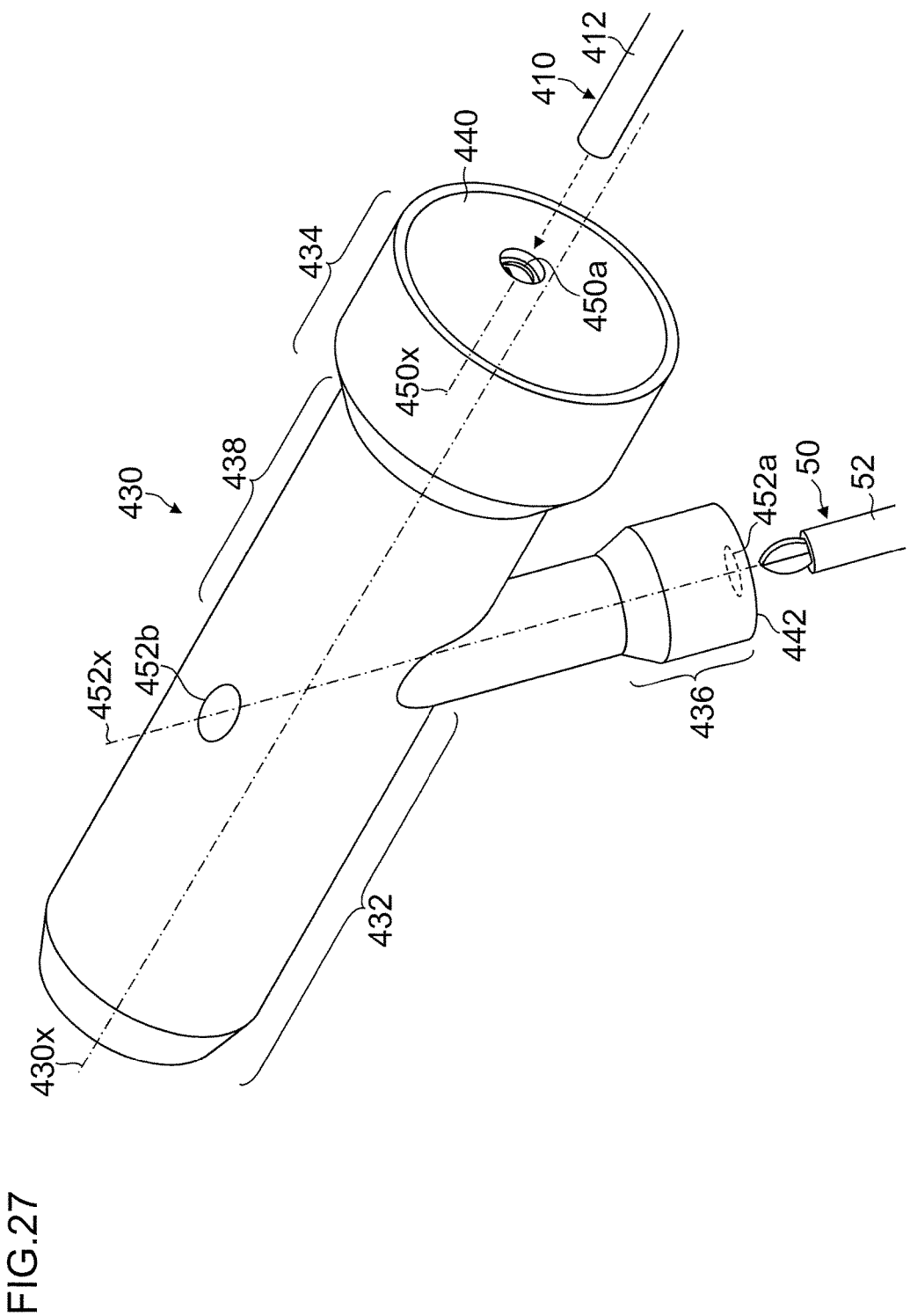
FIG. 27 is a rear perspective view of the outer tube in FIG. 25.

The outer tube 430 is formed into a columnar shape having a longitudinal axis 430x which becomes an insertion direction into a body cavity as a central axis, and includes a distal-side insertion part 432 that can be inserted in a body cavity wall and the body cavity, two proximal-side head parts 434 and 436 to be disposed outside the body, and a middle part 438 in which the insertion part 432 and two head parts 434 and 436 are coupled. FIG. 27 is a rear perspective view illustrating the outer tube 430 from the proximal side, and FIG. 28 is a front perspective view illustrating the outer tube 430 from the distal side.

Figure 28:
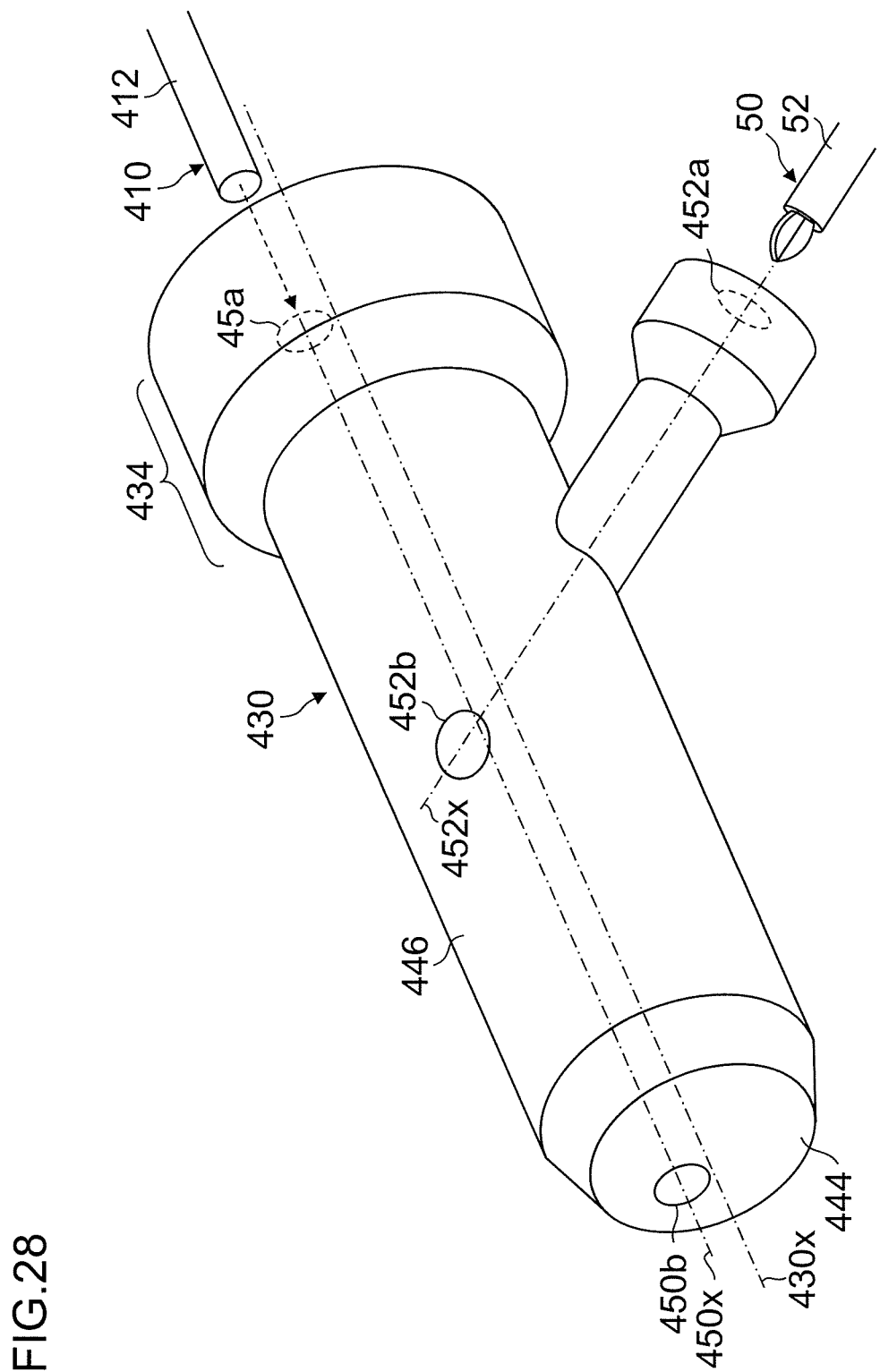
FIG. 28 is a front perspective view of the outer tube in FIG. 25.

As illustrated in FIGS. 26 to 28, the head part 434 is formed into a columnar shape having the longitudinal axis 430x as a central axis, and the distal end side is coupled with the insertion part 432 via the middle part 438. An endoscope entry port 450a through which the endoscope insertion part 412 of the endoscope 410 is inserted in the outer tube 430 is provided in a circular proximal end surface 440 of the head part 434.

The head part 436 is formed into a columnar shape having an axis inclined at a predetermined angle (for example, about 30 degrees) with respect to the direction of the longitudinal axis 430x, and the distal end side is coupled with the insertion part 432 via the middle part 438 of the outer tube 430. A treatment tool entry port 452a through which the treatment tool insertion part 52 of the treatment tool 50 is inserted in the outer tube 430 is provided in a circular proximal end surface 442 of the head part 436.

Meanwhile, in a circular distal end surface 444 of the insertion part 432, there is provided an endoscope exit port 450b to draw out the endoscope insertion part 412, which is inserted from the endoscope entry port 450a of the head part 434 and inserted in an endoscope insertion hole 450 in the outer tube 430, to the outside of the outer tube 430.

Moreover, in a side surface (outer peripheral surface) 446 of the insertion part 432, there is provided a treatment tool exit port 452b to draw out the treatment tool insertion part 52, which is inserted from the treatment tool entry port 452a of the head part 436 and inserted in a treatment tool insertion hole 452 in the outer tube 430, to the outside of the outer tube 430.

As illustrated in FIG. 26, the endoscope insertion hole 450 having an endoscope insertion axis 450x parallel to the longitudinal axis 430x as a central axis is provided inside the outer tube 430, its proximal end forms the endoscope entry port 450a on the proximal end surface 440 of the head part 434 and its distal end forms the endoscope exit port 450b on the distal end surface 444 of the insertion part 432.

Moreover, the treatment tool insertion hole 452 with a treatment tool insertion axis 452x non-parallel to the longitudinal axis 430x and the endoscope insertion axis 450x (a twisted positional relationship is provided) as a central axis is provided inside the outer tube 430, its proximal end forms the treatment tool entry port 452a on the proximal end surface 442 of the head part 436 and its distal end forms the treatment tool exit port 452b on the side surface 446 of the insertion part 432.

Here, the outer tube 430 includes; an outer tube body corresponding to the outer tube body 130 of the outer tube 100 illustrated in FIG. 8 or the like; and a valve member corresponding to the valve member 132 of the outer tube 100, and the valve member is provided in the proximal ends of the head parts 434 and 436, but the explanation is omitted.

As mentioned above, in the outer tube 430 in which the endoscope insertion hole 450 and the treatment tool insertion hole 452 are non-parallel (three-dimensionally intersect), an interlocking mechanism (referred to as an interlocking mechanism 500) which moves the endoscope insertion part 412 back and forth in interlock with the back-and-forth movement of the treatment tool insertion part 52 can be provided with a configuration similar to the interlocking mechanism 134 of the above-mentioned outer tube 100.

Figure 29:
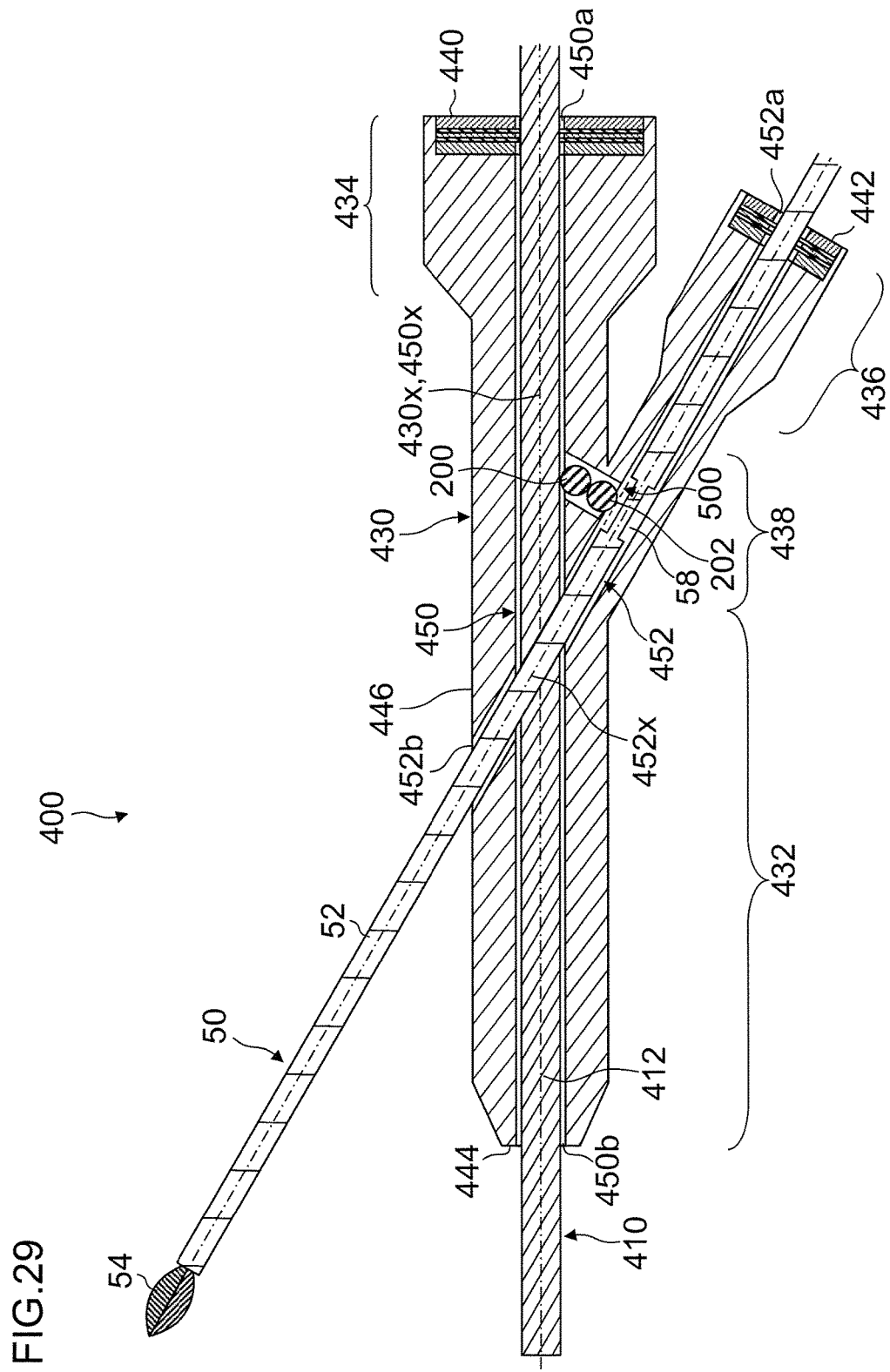
FIG. 29 is a schematic diagram illustrating the outer tube in FIG. 26 having the configuration of the interlocking mechanism of the first embodiment from the side surface side.

Application Example of Interlocking Mechanism of First Embodiment to Outer Tube for Side-Viewing Type Endoscope FIG. 29 is a schematic diagram illustrating the outer tube 430 including the interlocking mechanism 500 having a configuration similar to the interlocking mechanism 134 of the above-mentioned first embodiment illustrated in FIG. 8 or the like from the side surface side, as the interlocking mechanism 500 of the outer tube 430. Moreover, the same reference numerals are assigned to the same components as the interlocking mechanism 134 of the first embodiment, and only the outline of the interlocking mechanism 500 is described here.

As illustrated in the figure, the interlocking mechanism 500 configured in the same way as the interlocking mechanism 134 of the first embodiment is disposed in a cavity part of a region sandwiched by a part on the proximal end side of the endoscope insertion hole 450 and a part on the proximal end side of the treatment tool insertion hole 452, with respect to a position in which the endoscope insertion hole 450 and the treatment tool insertion hole 452 intersect in the figure.

The interlocking mechanism 500 includes the endoscope-side roller 200 and the treatment tool-side roller 202, and their central axes (rotation axes) are disposed so as to be orthogonal to a horizontal reference surface (a plane which includes the endoscope insertion axis 450x and is parallel to the treatment tool insertion axis 452x). That is, respective central axes of the endoscope-side roller 200 and the treatment tool-side roller 202 are disposed so as to be orthogonal to a plane parallel to both the endoscope insertion axis 450x and the treatment tool insertion axis 452x.

Further, the outer peripheral surface of the endoscope-side roller 200 and the outer peripheral surface of the treatment tool-side roller 202 contact with each other. By this means, the endoscope-side roller 200 and the treatment tool-side roller 202 rotate in interlock with each other.

The outer peripheral surface of the endoscope-side roller 200 is disposed so as to project into the endoscope insertion hole 450 and contact with the outer peripheral surface of the endoscope insertion part 412 inserted in the endoscope insertion hole 450.

On the other hand, the outer peripheral surface of the treatment tool-side roller 202 is disposed so as to project into the treatment tool insertion hole 452 and contact with the outer peripheral surface of the non-reduced diameter part of the treatment tool insertion part 52 inserted in the treatment tool insertion hole 452.

By this means, the endoscope insertion part 12 moves back and forth through the interlocking mechanism 500 in interlock with the back-and-forth movement of the treatment tool insertion part 52, and there is provided an allowance of the interlocking mechanism 500 in which the treatment tool insertion part 52 and the endoscope insertion part 12 are not interlocked in a state where the reduced diameter part 58 of the treatment tool insertion part 52 faces the treatment tool-side roller 202.

Figure 30:
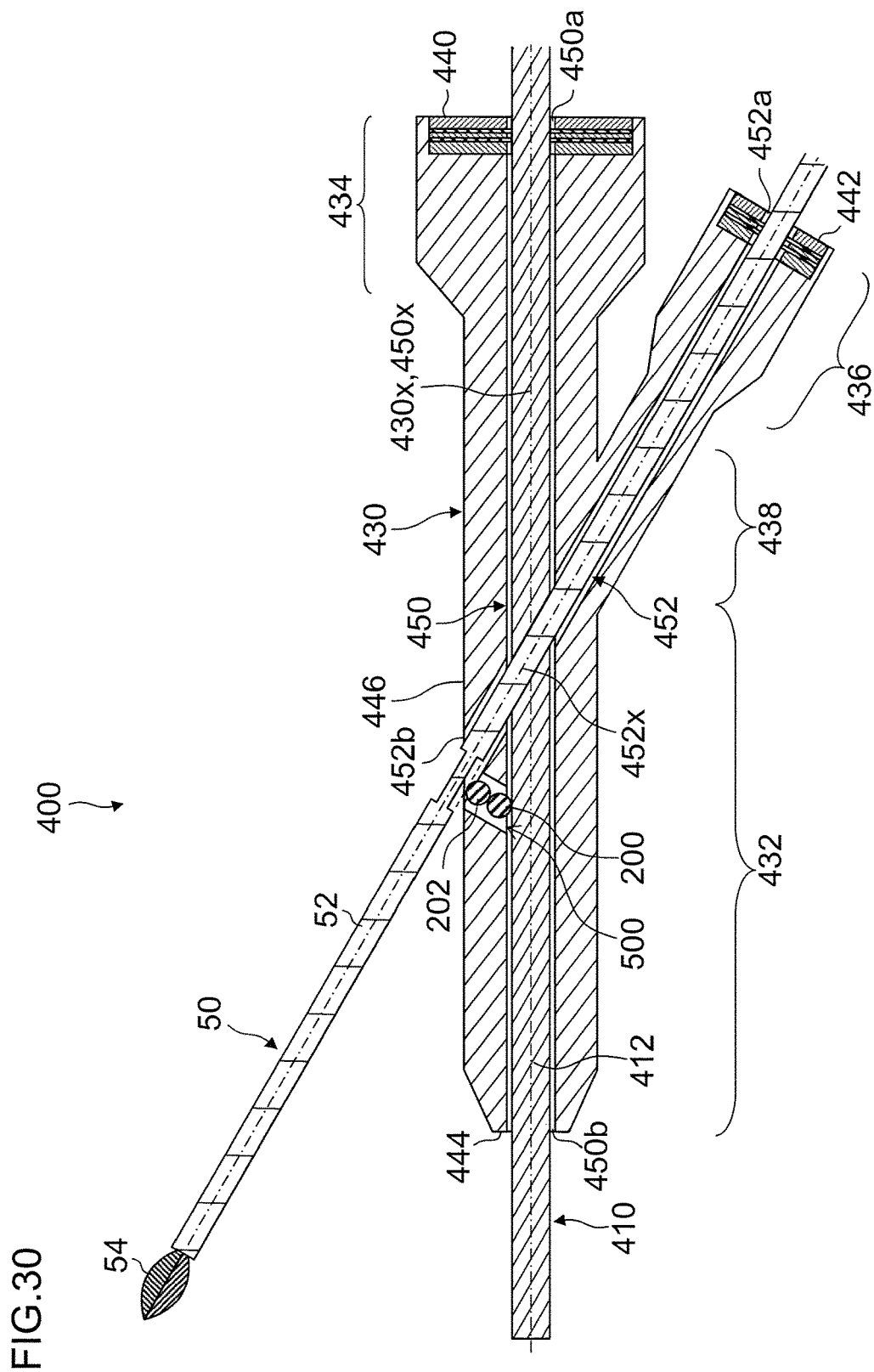
FIG. 30 is a schematic diagram illustrating the outer tube in FIG. 26 in a case where an interlocking mechanism of the first embodiment is disposed in a position different from FIG. 29, from the side surface side.

Here, the interlocking mechanism 500 in this mode may be disposed in an unillustrated cavity part formed in a region sandwiched by a part on the distal end side of the endoscope insertion hole 450 and a part on the distal end side of the treatment tool insertion hole 452, with respect to a position in which the endoscope insertion hole 450 and the treatment tool insertion hole 452 intersect in the figure as illustrated in FIG. 30.

Moreover, the allowance of the interlocking mechanism 500 may be provided by an allowance generation member (pipe member 250) as illustrated in FIGS. 20 and 21 instead of the reduced diameter part 58 of the treatment tool insertion part 52.

Figure 31:
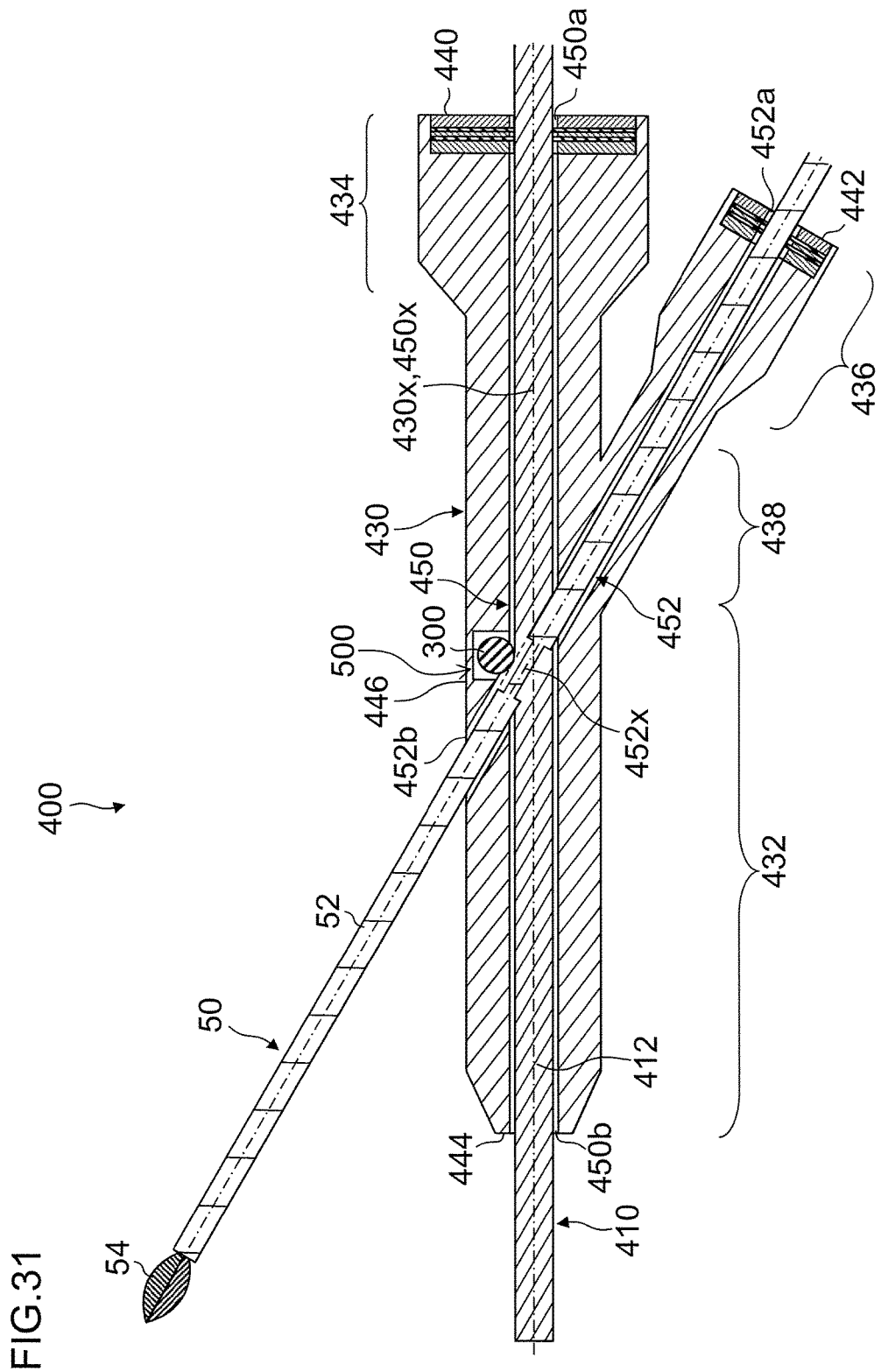
FIG. 31 is a schematic diagram illustrating the outer tube in FIG. 26 having the configuration of an interlocking mechanism of the second embodiment from the side surface side.

Application Example of Interlocking Mechanism of Second Embodiment to Outer Tube for Side-Viewing Type Endoscope FIG. 31 is a schematic diagram illustrating the outer tube 430 having the interlocking mechanism 500 of a configuration similar to the interlocking mechanism 134 of the above-mentioned second embodiment illustrated in FIG. 23 or the like from the side surface side. Moreover, the same reference numerals are given to the same components as the interlocking mechanism 134 of the second embodiment, the detailed explanation is omitted, and only the outline of the interlocking mechanism 500 is described here.

As illustrated in the figure, the interlocking mechanism 500 configured in the same way as the interlocking mechanism 134 of the second embodiment is disposed in a cavity part of a region sandwiched by a part on the proximal end side of the endoscope insertion hole 450 and a part on the distal end side of the treatment tool insertion hole 452, with respect to a position in which the endoscope insertion hole 450 and the treatment tool insertion hole 452 intersect in the figure.

The interlocking mechanism 500 includes one roller 300, and its central axis (rotation axis) is disposed so as to be orthogonal to the horizontal reference surface. That is, the central axis of the roller 300 is disposed in a direction orthogonal to a plane parallel to both the endoscope insertion axis 450x and the treatment tool insertion axis 452x.

Further, the outer peripheral surface of the roller 300 projects into the endoscope insertion hole 450 and projects into the treatment tool insertion hole 452. Further, the roller 300 is disposed such that the outer peripheral surface of the roller 300 contacts with the outer peripheral surface of the endoscope insertion part 412 inserted in the endoscope insertion hole 450 and the outer peripheral surface of the non-reduced diameter part of the treatment tool insertion part 52 inserted in the treatment tool insertion hole 452.

By this means, the endoscope insertion part 12 moves back and forth in interlock with the back-and-forth movement of the treatment tool insertion part 52 through the interlocking mechanism 500, and there is provided an allowance of the interlocking mechanism 500 in which they are not interlocked in a state that the reduced diameter part 58 of the treatment tool insertion part 52 faces the treatment tool-side roller 202.

Figure 32:
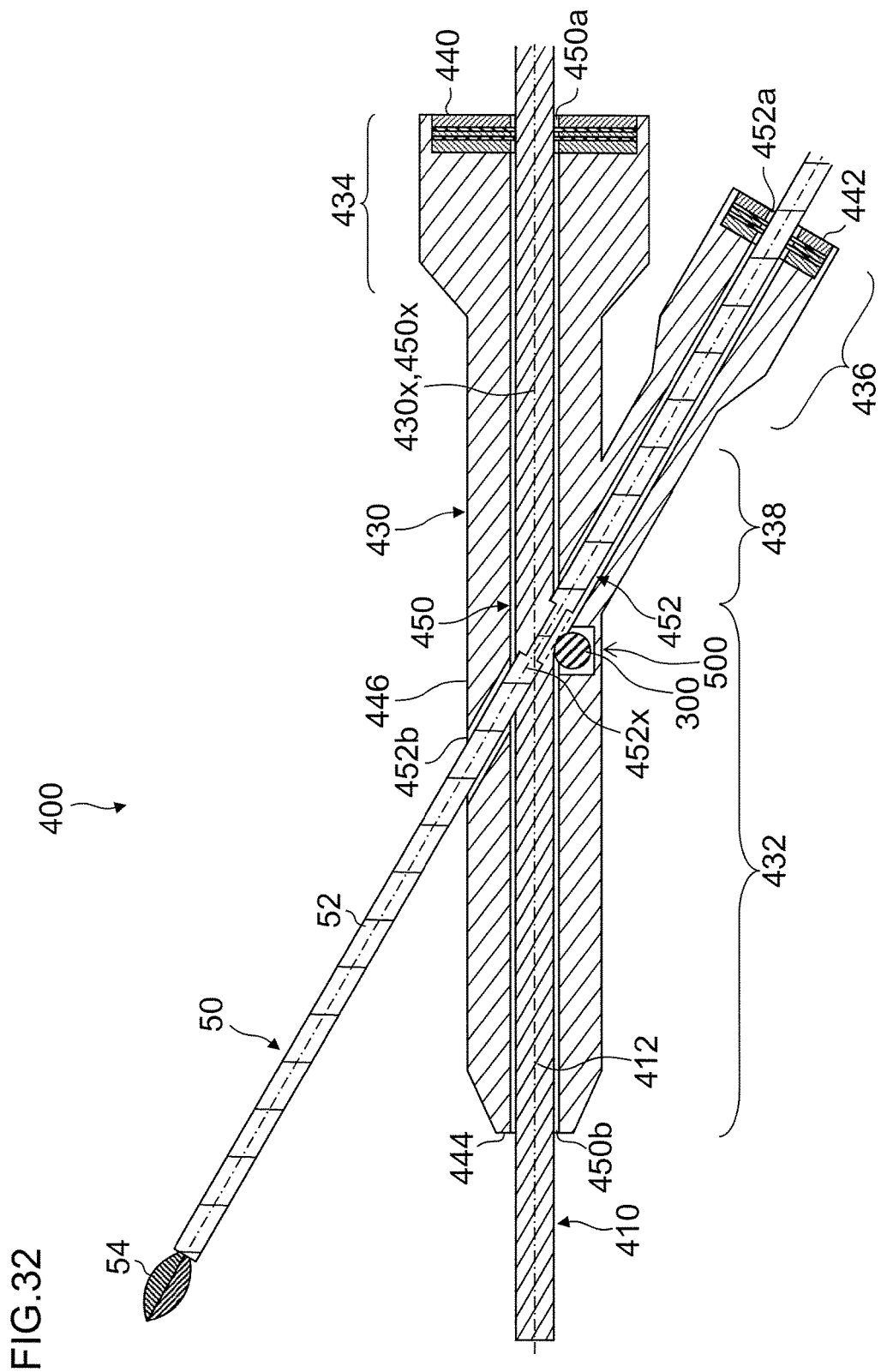
FIG. 32 is a schematic diagram illustrating the outer tube in FIG. 26 in a case where the interlocking mechanism of the second embodiment is disposed in a position different from FIG. 31, from the side surface side.

Here, the interlocking mechanism 500 of the second embodiment may be disposed in a region sandwiched by a part on the distal end side of the endoscope insertion hole 450 and a part on the proximal end side of the treatment tool insertion hole 452, with respect to a position in which the endoscope insertion hole 450 and the treatment tool insertion hole 452 intersect in the figure as illustrated in FIG. 32.

Moreover, the allowance of the interlocking mechanism 500 may be provided by an allowance generation member (pipe member 250) as illustrated in FIGS. 20 and 21 instead of the reduced diameter part 58 of the treatment tool insertion part 52.

Figure 33:
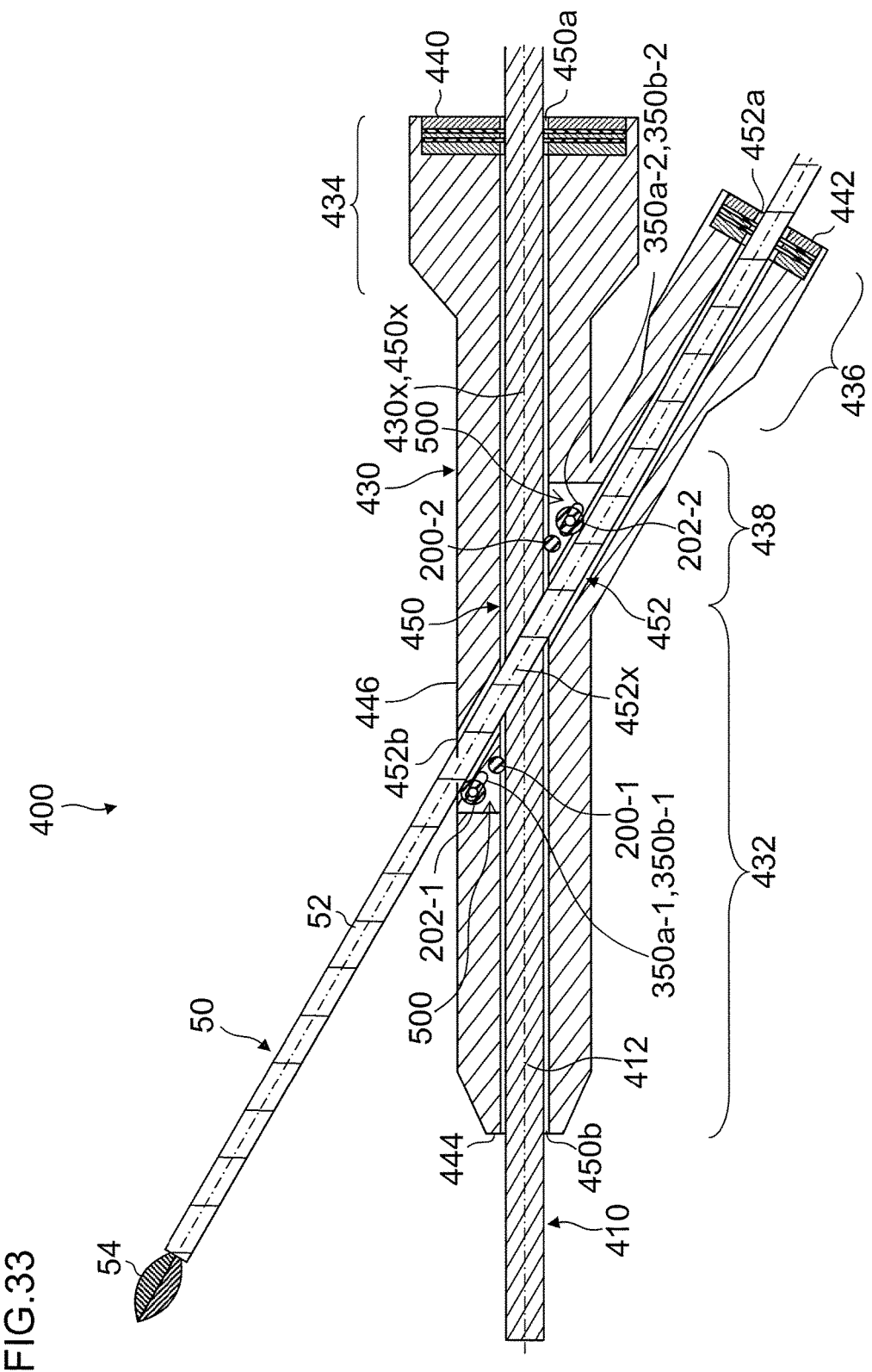
FIG. 33 is a schematic diagram illustrating the outer tube in FIG. 26 having the configuration of an interlocking mechanism of the third embodiment from the side surface side.

Application Example of Interlocking Mechanism of Third Embodiment to Outer Tube for Side-Viewing Type Endoscope FIG. 33 is a schematic diagram illustrating the outer tube 430 having the interlocking mechanism 500 of a configuration to which the interlocking mechanism 134 of the above-mentioned third embodiment illustrated in FIG. 25 is applied, from the side surface side. Moreover, the same reference numerals are assigned to components having function identical or similar to the interlocking mechanism 134 of the third embodiment, and only the outline of the interlocking mechanism 500 is described here.

As illustrated in the figure, the interlocking mechanism 500 of a configuration to which the interlocking mechanism 134 of the third embodiment is applied is disposed in a cavity part of a region sandwiched by a part on the distal end side of the endoscope insertion hole 450 and a part on the distal end side of the treatment tool insertion hole 452 and in a cavity part of a region sandwiched by a part on the proximal end side of the endoscope insertion hole 450 and a part on the proximal end side of the treatment tool insertion hole 452, with respect to a position in which the endoscope insertion hole 450 and the treatment tool insertion hole 452 intersect in the figure.

The interlocking mechanism 500 includes the endoscope-side rollers 200-1 and 200-2 and treatment tool-side rollers 202-1 and 202-2, and their central axes (rotation axes) are disposed so as to be orthogonal to the horizontal reference surface. That is, respective central axes of the endoscope-side rollers 200-1 and 200-2 and the treatment tool-side rollers 202-1 and 202-2 are disposed in a direction orthogonal to a plane parallel to both the endoscope insertion axis 450x and the treatment tool insertion axis 452x.

Further, the central axis (rotation axis) of the treatment tool-side roller 202-1 is internally fitted into a pair of engagement grooves 350a-1 and 350b-1 that are provided so as to extend in the back-and-forth direction along the treatment tool insertion axis 452x. Therefore, the treatment tool-side roller 202-1 is supported so as to be rotatable around the central axis and is supported so as to be movable in a direction along the treatment tool insertion axis 452x. By this means, the treatment tool-side roller 202-1 is supported so as to be movable between a position in which the outer peripheral surface thereof contacts with the outer peripheral surface of the endoscope-side roller 200-1 and a position in which they are separated.

The central axis (rotation axis) of the treatment tool-side roller 202-2 is internally fitted into a pair of engagement grooves 350a-2 and 350b-2 that are extended and provided in the back-and-forth direction along the treatment tool insertion axis 452x. Therefore, the treatment tool-side roller 202-2 is supported so as to be rotatable around the central axis thereof and is supported so as to be movable in a direction along the treatment tool insertion axis 452x. By this means, the treatment tool-side roller 202-2 is supported so as to be movable between a position in which the outer peripheral surface thereof contacts with the outer peripheral surface of the endoscope-side roller 200-2 and a position in which they are separated.

Moreover, the endoscope-side rollers 200-1 and 200-2 are supported so as to be rotatable around the central axes thereof in the same way as the endoscope-side rollers 200-1 and 200-2 in FIG. 25, and each of the outer peripheral surfaces of the endoscope-side rollers 200-1 and 200-2 is disposed so as to project into the endoscope insertion hole 450 and contact with the outer peripheral surface of the endoscope insertion part 412 inserted in the endoscope insertion hole 450.

Meanwhile, the outer peripheral surfaces of the treatment tool-side rollers 202-1 and 202-2 are disposed so as to project into the treatment tool insertion hole 452 and contact with the outer peripheral surface of the treatment tool insertion part 52 inserted in the treatment tool insertion hole 452. Here, processing (machining) like the above-mentioned reduced diameter part 58 is not performed on the treatment tool insertion part 52.

According to this, when the treatment tool insertion part 52 is moved forward, in interlock with this movement, the treatment tool-side roller 202-2 moves in a direction to contact with the endoscope-side roller 200-2 and the treatment tool-side roller 202-1 moves in a direction to separate from the endoscope-side roller 200-1. Further, when the treatment tool-side roller 202-2 and the endoscope-side roller 200-2 contact with each other, they rotate in interlock with the forward movement of the treatment tool insertion part 52 and the endoscope insertion part 412 moves forward.

By contrast, when the treatment tool insertion part 52 is moved backward, in interlock with this movement, the treatment tool-side roller 202-1 moves in a direction to contact with the endoscope-side roller 200-1 and the treatment tool-side roller 202-2 moves in a direction to separate from the endoscope-side roller 200-2. Further, when the treatment tool-side roller 202-1 and the endoscope-side roller 200-1 contact with each other, they rotate in interlock with the backward movement of the treatment tool insertion part 52 and the endoscope insertion part 412 moves backward. Moreover, when the treatment tool insertion part 52 is moved forward or moved backward, there exists a state where the treatment tool-side roller 202-1 does not contact with the endoscope-side roller 200-1 and the treatment tool-side roller 202-2 does not contact with the endoscope-side roller 200-2, until the time the treatment tool-side roller 202-2 and the endoscope-side roller 200-2 contact with each other or the treatment tool-side roller 202-1 and the endoscope-side roller 200-1 contact with each other. Such the state is provided as an allowance of the interlocking mechanism 500.

What is claimed is:

1. A medical instrument guiding device comprising:
   an outer tube comprising a proximal end surface and a distal end surface with a central longitudinal axis extending from the proximal end surface to the distal end surface, the outer tube configured to penetrate a body wall and to be inserted in a body cavity;
   an endoscope channel formed in the outer tube extending from the proximal end surface to the distal end surface and an endoscope that performs observation in the body cavity is configured for axial movement along a longitudinal axis of the endoscope channel;

a treatment tool channel formed in the outer tube extending from the proximal end surface to the distal end surface and a treatment tool that inspects or treats a disease site in the body cavity is configured for axial movement along a longitudinal axis of the treatment tool channel;

a back-and-forth movement transmission mechanism comprising:

a treatment tool-side roller having a first rotation axis provided within an intermediate area of the outer tube between the endoscope channel and the treatment tool channel, the first rotation axis of the treatment tool-side roller disposed between the longitudinal axis of the treatment tool channel and the central longitudinal axis of the outer tube, the treatment tool-side roller configured to contact the treatment tool and rotate in response to axial movement of the treatment tool along the longitudinal axis of the treatment tool channel;

an endoscope-side roller having a second rotation axis provided within the intermediate area of the outer tube between the endoscope channel and the treatment tool channel, the second rotation axis of the endoscope-side roller disposed between the longitudinal axis of the endoscope channel and the central longitudinal axis of the outer tube; the endoscope-side roller confi red to contact the treatment tool-side roller and the endoscope and rotate in response to rotation of the treatment tool-side roller to transmit axial movement to the endoscope along the longitudinal axis of the endoscope channel, the endoscope-side roller and treatment tool-side roller configured to rotate in interlock with each other.

2. The medical instrument guiding device according to claim 1, wherein the endoscope-side roller is directly in contact and coupled with the treatment tool-side roller and rotates in interlock with the rotation of the treatment tool-side roller.

3. The medical instrument guiding device according to claim 1, wherein the first rotation axis of the treatment tool-side roller and the second rotation axis of the endoscope-side roller are disposed in a direction orthogonal to a plane parallel to the longitudinal axis of the treatment tool channel and the longitudinal axis of the endoscope channel.

4. The medical instrument guiding device according to claim 1, wherein the first rotation axis of the treatment tool-side roller and the second rotation axis of the endoscope-side roller three-dimensionally intersect with each other.

5. The medical instrument guiding device according to claim 1, wherein the first rotation axis of the treatment tool-side roller and the second rotation axis of the endoscope-side roller are disposed in parallel to a plane which contacts with an outer peripheral surface of the treatment tool and an outer peripheral surface of the endoscope from one identical direction.

6. The medical instrument guiding device according to claim 1, wherein:

the longitudinal axis of the treatment tool channel and the longitudinal axis of the endoscope channel are disposed in nonparallel with each other; and the first rotation axis of the treatment tool-side roller and the second rotation axis of the endoscope-side roller are disposed in a direction orthogonal to a plane which is parallel to the longitudinal axis of the treatment tool channel and the longitudinal axis of the endoscope channel.

7. The medical instrument guiding device according to claim 1, wherein:

the treatment tool includes an operation part, an insertion part and a treatment part;

the insertion part includes a large diameter part having a first outer diameter and a small diameter part having a second outer diameter which is smaller than the first outer diameter; and the treatment tool-side roller contacts with the large diameter part and rotates according to a back-and-forth movement of the treatment tool, and does not contact with the small diameter part nor rotate according to the back-and-forth movement of the treatment tool.

8. The medical instrument guiding device according to claim 1, wherein the treatment tool channel further includes an allowance generation member, and the treatment tool-side roller and the endoscope-side roller transmit a back-and-forth movement of the treatment tool to the endoscope through the allowance generation member.

9. The medical instrument guiding device according to claim 1, wherein the endoscope channel further includes an allowance generation member, and the treatment tool-side roller and the endoscope-side roller transmit a back-and-forth movement of the treatment tool to the endoscope through the allowance generation member.

10. The medical instrument guiding device according to claim 1, further comprising an allowance generation member provided between the treatment tool-side roller and the endoscope side-roller.

11. The medical instrument guiding device according to claim 1, wherein the treatment tool-side roller and the endoscope-side roller have an anti-slipping portion, and the anti-slipping portion is disposed on surfaces of the treatment tool-side roller and the endoscope-side roller.

12. The medical instrument guiding device according to claim 11, wherein the anti-slipping portion is a concavity and convexity.

13. The medical instrument guiding device according to claim 12, wherein the concavity and convexity is a tooth of a toothed wheel.

14. The medical instrument guiding device according to claim 11, wherein the anti-slipping portion includes a material having a larger friction coefficient than a material of the treatment tool-side roller and the endoscope-side roller.

* * * * *